(12) United States Patent
Ichikawa et al.

(10) Patent No.: US 8,921,029 B2
(45) Date of Patent: *Dec. 30, 2014

(54) RESIST COMPOSITION AND METHOD FOR PRODUCING RESIST PATTERN

(75) Inventors: Koji Ichikawa, Osaka (JP); Yukako Anryu, Osaka (JP); Shingo Fujita, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,807

(22) Filed: Jul. 18, 2012

(65) Prior Publication Data

US 2013/0022917 A1    Jan. 24, 2013

(30) Foreign Application Priority Data

Jul. 19, 2011    (JP) ................................. 2011-157525

(51) Int. Cl.
| | | |
|---|---|---|
| G03F 7/004 | (2006.01) | |
| G03F 7/38 | (2006.01) | |
| C07C 303/32 | (2006.01) | |
| C07C 309/06 | (2006.01) | |
| C07C 309/12 | (2006.01) | |
| C07D 333/46 | (2006.01) | |
| C07D 335/02 | (2006.01) | |
| G03F 7/039 | (2006.01) | |
| G03F 7/20 | (2006.01) | |

(52) U.S. Cl.
CPC ............... *G03F 7/0045* (2013.01); *G03F 7/38* (2013.01); *C07C 303/32* (2013.01); *C07D 335/02* (2013.01); *C07D 333/46* (2013.01); *C07C 309/06* (2013.01); *C07C 309/12* (2013.01); *G03F 7/0046* (2013.01); *G03F 7/0397* (2013.01); *G03F 7/2041* (2013.01); *Y10S 430/108* (2013.01); *Y10S 430/111* (2013.01); *Y10S 430/122* (2013.01); *Y10S 430/123* (2013.01)
USPC ........ 430/270.1; 430/326; 430/330; 430/907; 430/910; 430/921; 430/922; 549/13; 549/29; 549/79; 562/100; 562/109; 562/113

(58) Field of Classification Search
CPC ....... G03F 7/0045; G03F 7/0397; G03F 7/38; C07C 303/32; C07C 309/06; C07C 309/12; C07D 333/46; C07D 335/02
USPC .............. 430/270.1, 910, 921, 922, 326, 330, 430/907; 549/13, 29, 79; 562/100, 109, 113
See application file for complete search history.

(56) References Cited

U.S. PATENT DOCUMENTS

| | | |
|---|---|---|
| 3,779,778 A | 12/1973 | Smith et al. |
| 3,849,137 A | 11/1974 | Barzynski et al. |
| 4,576,902 A | 3/1986 | Saenger et al. |
| 4,822,716 A | 4/1989 | Onishi et al. |
| 4,857,437 A | 8/1989 | Banks et al. |
| 5,017,453 A | 5/1991 | Onishi et al. |
| 5,073,476 A | 12/1991 | Meier et al. |
| 5,198,520 A | 3/1993 | Onishi et al. |

(Continued)

FOREIGN PATENT DOCUMENTS

| | | |
|---|---|---|
| DE | 3914407 A1 | 10/1990 |
| EP | 0126712 A1 | 11/1984 |

(Continued)

OTHER PUBLICATIONS

United States Office Action for copending U.S. Appl. No. 13/295,943 dated Jul. 3, 2013.

(Continued)

*Primary Examiner* — John Chu
(74) *Attorney, Agent, or Firm* — Birch, Stewart, Kolasch & Birch, LLP

(57) ABSTRACT

A resist composition having a resin having a structural unit represented by the formula (I), a resin being insoluble or poorly soluble in alkali aqueous solution, but becoming soluble in an alkali aqueous solution by the action of an acid and not including the structural unit represented by the formula (I), and an acid generator represented by the formula (II),

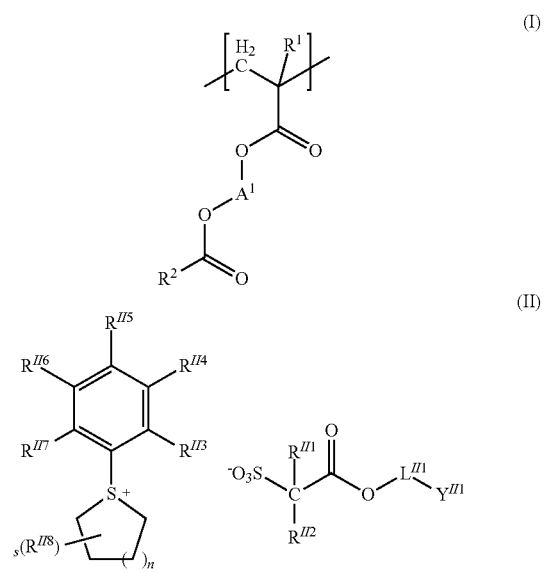

wherein $R^1$, $A^1$, $R^2$, $R^{II1}$, $R^{II2}$, $L^{II1}$, $Y^{II1}$, $R^{II3}$, $R^{II4}$, $R^{II5}$, $R^{II6}$, $R^{II7}$, n, s and $R^{II8}$ are defined in the specification.

7 Claims, No Drawings

(56) References Cited

U.S. PATENT DOCUMENTS

| | | | |
|---|---|---|---|
| 5,260,410 A | 11/1993 | Schwalm | |
| 5,453,341 A | 9/1995 | Schwalm | |
| 5,663,035 A | 9/1997 | Masuda et al. | |
| 7,304,175 B2 | 12/2007 | Harada et al. | |
| 7,439,006 B2 | 10/2008 | Yoshida et al. | |
| 7,575,850 B2 | 8/2009 | Takata et al. | |
| 7,579,132 B2 | 8/2009 | Harada et al. | |
| 7,612,217 B2 | 11/2009 | Sakamoto et al. | |
| 7,927,780 B2* | 4/2011 | Kawaue et al. | 430/270.1 |
| 8,039,200 B2 | 10/2011 | Kodama | |
| 8,124,803 B2 | 2/2012 | Yoshida et al. | |
| 8,206,886 B2 | 6/2012 | Kodama | |
| 2005/0209224 A1 | 9/2005 | Singh et al. | |
| 2005/0266336 A1 | 12/2005 | Kodama | |
| 2006/0193874 A1 | 8/2006 | Jones | |
| 2006/0194982 A1 | 8/2006 | Harada et al. | |
| 2007/0027336 A1 | 2/2007 | Yoshida et al. | |
| 2008/0044738 A1 | 2/2008 | Harada et al. | |
| 2008/0076063 A1 | 3/2008 | Yoshida et al. | |
| 2008/0081925 A1 | 4/2008 | Sakamoto et al. | |
| 2008/0090171 A1 | 4/2008 | Irie et al. | |
| 2009/0023095 A1 | 1/2009 | Hada et al. | |
| 2009/0068591 A1 | 3/2009 | Kawaue et al. | |
| 2009/0197204 A1 | 8/2009 | Shiono et al. | |
| 2009/0202945 A1 | 8/2009 | Nakagawa et al. | |
| 2009/0317745 A1 | 12/2009 | Mimura et al. | |
| 2010/0035185 A1 | 2/2010 | Hagiwara et al. | |
| 2010/0081088 A1 | 4/2010 | Kawaue et al. | |
| 2010/0203446 A1 | 8/2010 | Ichikawa et al. | |
| 2010/0304300 A1 | 12/2010 | Kodama | |
| 2011/0020749 A1 | 1/2011 | Ichikawa et al. | |
| 2011/0053082 A1 | 3/2011 | Ichikawa et al. | |
| 2011/0111343 A1 | 5/2011 | Hirano et al. | |
| 2011/0171576 A1 | 7/2011 | Yamaguchi et al. | |
| 2011/0200935 A1 | 8/2011 | Masuyama et al. | |
| 2011/0201823 A1 | 8/2011 | Yoshida et al. | |
| 2012/0015297 A1 | 1/2012 | Komuro et al. | |
| 2012/0028188 A1 | 2/2012 | Ichikawa et al. | |
| 2012/0052443 A1 | 3/2012 | Masuyama et al. | |
| 2012/0088190 A1 | 4/2012 | Ichikawa et al. | |
| 2012/0100483 A1 | 4/2012 | Masuyama et al. | |
| 2012/0100487 A1 | 4/2012 | Hirano et al. | |
| 2012/0122032 A1* | 5/2012 | Anryu et al. | 430/281.1 |
| 2012/0135350 A1 | 5/2012 | Kobayashi et al. | |
| 2012/0156620 A1 | 6/2012 | Ichikawa et al. | |
| 2012/0237875 A1 | 9/2012 | Asano et al. | |
| 2013/0022912 A1* | 1/2013 | Sato et al. | 430/270.1 |

FOREIGN PATENT DOCUMENTS

| | | |
|---|---|---|
| JP | 55-164824 A | 12/1980 |
| JP | 62-69263 A | 3/1987 |
| JP | 62-153853 A | 7/1987 |
| JP | 63-26653 A | 2/1988 |
| JP | 63-146029 A | 6/1988 |
| JP | 63-146038 A | 6/1988 |
| JP | 63-163452 A | 7/1988 |
| JP | 11-52575 A | 2/1999 |
| JP | 2005-221721 A | 8/2005 |
| JP | 2006-257078 A | 9/2006 |
| JP | 2007-57670 A | 3/2007 |
| JP | 2007-514775 A | 6/2007 |
| JP | 2007-224008 A | 9/2007 |
| JP | 2008-13551 A | 1/2008 |
| JP | 2008-69146 A | 3/2008 |
| JP | 2008-127387 A | 6/2008 |
| JP | 2008-209917 A | 9/2008 |
| JP | 2009-145408 A | 7/2009 |
| JP | 2009-229603 A | 10/2009 |
| JP | 2010-26478 A | 2/2010 |
| JP | 2010-61018 A | 3/2010 |
| JP | 2010-111660 A | 5/2010 |
| JP | 2010-152341 A | 7/2010 |
| JP | 2010-197413 A | 9/2010 |
| JP | 2010-204646 A | 9/2010 |
| JP | 2011-128226 A | 6/2011 |
| WO | WO 2008/099869 A1 | 8/2008 |
| WO | WO 2011/034176 A1 | 3/2011 |

OTHER PUBLICATIONS

United States Office Action for copending U.S. Appl. No. 13/295,943 dated Mar. 15, 2013.

Luis et al., "Non Concerted Pathways in the Generation of Dehydroarenes by Thermal Decomposition of Diaryliodonium Carboxylates", Tetrahedron, vol. 45, No. 19, 1989, pp. 6281-6296.

Machine English translation of JP-2010-197413-A dated Sep. 9, 2010.

United States Office Action for copending U.S. Appl. No. 13/551,724 dated May 10, 2013.

United States Office Action for copending U.S. Appl. No. 13/551,855 dated Apr. 25, 2013.

United States Office Action for copending U.S. Appl. No. 13/551,860 dated Mar. 21, 2013.

United States Office Action for copending U.S. Appl. No. 13/551,864 dated Apr. 11, 2013.

United States Office Action for copending U.S. Appl. No. 13/551,874 dated May 9, 2013.

United States Office Action for copending U.S. Appl. No. 13/551,906 dated Apr. 26, 2013.

United States Office Action for copending U.S. Appl. No. 13/551,980 dated May 9, 2013.

United States Office Action for copending U.S. Appl. No. 13/552,044 dated May 9, 2013.

United States Office Action for copending U.S. Appl. No. 13/552,242 dated May 14, 2013.

United States Office Action for copending U.S. Appl. No. 13/552,273 dated Apr. 23, 2013.

United States Office Action for copending U.S. Appl. No. 13/552,278 dated Apr. 25, 2013.

United States Office Action for copending U.S. Appl. No. 13/552,281 dated Feb. 22, 2013.

United States Office Action for copending U.S. Appl. No. 13/552,315 dated Feb. 25, 2013.

* cited by examiner

RESIST COMPOSITION AND METHOD FOR PRODUCING RESIST PATTERN

CROSS-REFERENCE TO RELATED APPLICATIONS

This application claims priority to Japanese Application No. 2011-157525 filed on Jul. 19, 2011. The entire disclosures of Japanese Application No. 2011-157525 is incorporated hereinto by reference.

BACKGROUND OF THE INVENTION

1. Field of the Invention

The present invention relates to a resist composition and a method for producing a resist pattern.

2. Background Information

A resist composition which contains a resin including a polymer having a structural unit (u-A) and a structural unit (u-B), and a polymer having a structural unit (u-B), a structural unit (u-C) and a structural unit (u-D), and an acid generator, is described in Patent document of JP-2010-197413A.

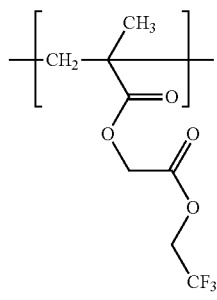
(u-A)

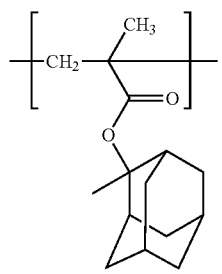
(u-B)

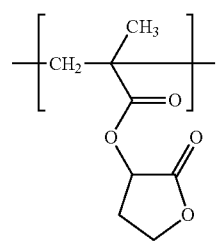
(u-C)

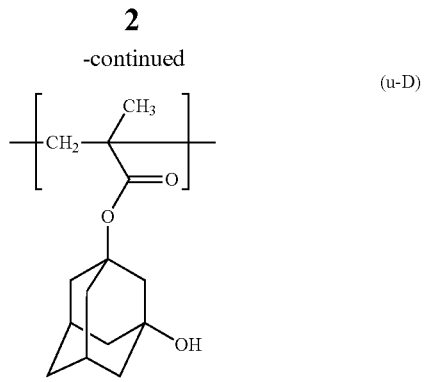
(u-D)

However, with the conventional resist composition containing the above resin, the critical dimension uniformity (CDU) of the obtained resist pattern may be not always satisfied with.

SUMMARY OF THE INVENTION

The present invention provides following inventions of <1> to <8>.

<1> A resist composition having
a resin having a structural unit represented by the formula (I),
a resin being insoluble or poorly soluble in alkali aqueous solution, but becoming soluble in an alkali aqueous solution by the action of an acid and not including the structural unit represented by the formula (I), and
an acid generator represented by the formula (II),

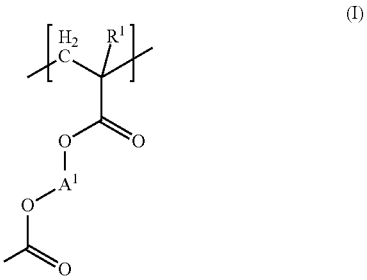
(I)

wherein $R^1$ represents a hydrogen atom or a methyl group;
$A^1$ represents a $C_1$ to $C_6$ alkanediyl group;
$R^2$ represents a $C_1$ to $C_{10}$ hydrocarbon group having a fluorine atom;

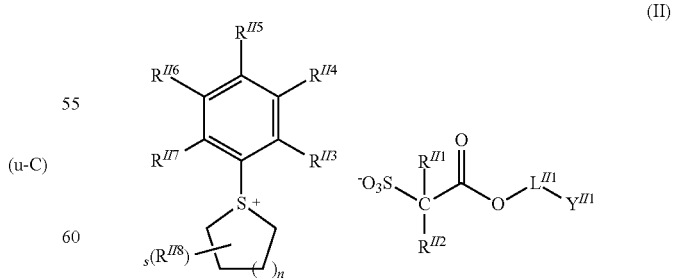
(II)

wherein $R^{II1}$ and $R^{II2}$ independently represent a fluorine atom or a $C_1$ to $C_6$ perfluoroalkyl group;
$L^{II1}$ represents a single bond, a $C_1$ to $C_6$ alkanediyl, a $C_4$ to $C_8$ divalent alicyclic hydrocarbon group, —(CH$_2$)$_t$—CO—

O—* or —(CH$_2$)$_t$—CO—O—CH$_2$—(CH$_2$)$_u$—*, one or more —CH$_2$— contained in the alkanediyl, —(CH$_2$)$_t$—CO—O—* or —(CH$_2$)$_t$—CO—O—CH$_2$—(CH$_2$)$_u$—* may be replaced by —O—, t represents an integer of 1 to 12, u represents an integer of 0 to 12, * represents a bond to Y$^{II1}$;

Y$^{II1}$ represents an optionally substituted C$_3$ to C$_{18}$ alicyclic hydrocarbon group, and one or more —CH$_2$— contained in the alicyclic hydrocarbon group may be replaced by —O—, —CO— or —SO$_2$—;

R$^{II3}$, R$^{II4}$, R$^{II5}$, R$^{II6}$ and R$^{II7}$ independently represent a hydrogen atom, a hydroxy group, a C$_1$ to C$_6$ alkyl group, a C$_1$ to C$_6$ alkoxy group, a C$_2$ to C$_7$ alkoxycarbonyl group or a C$_2$ to C$_{12}$ acyloxy group, one or more —CH$_2$— contained in sulfur-containing ring of cation may be replaced by —O— or —CO—;

n represents an integer of 1 to 3;

s represents an integer of 0 to 3; and

R$^{II8}$ in each occurrence independently represent a C$_1$ to C$_6$ alkyl group.

<2> The resist composition according to <1>, which further comprises an acid generator represented by the formula (III);

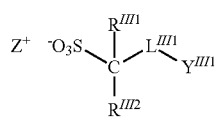

(III)

wherein R$^{III1}$ and R$^{III2}$ independently represent a fluorine atom or a C$_1$ to C$_6$ perfluoroalkyl group;

L$^{III1}$ represents a single bond or a C$_1$ to C$_{17}$ divalent saturated hydrocarbon group, one or more hydrogen atom in the saturated hydrocarbon group may be replaced by a fluorine atom or a hydroxy group, and one or more —CH$_2$— contained in the saturated hydrocarbon group may be replaced by —O— or —CO—;

Y$^{III1}$ represents an optionally substituted C$_1$ to C$_{18}$ alkyl group or an optionally substituted C$_3$ to C$_{18}$ alicyclic hydrocarbon group, and one or more —CH$_2$— contained in the alkyl group and alicyclic hydrocarbon group may be replaced by —O—, —CO— or —SO$_2$—; and Z$^+$ represents an organic cation.

<3> The resist composition according to <2>, wherein Z$^+$ in the formula (III) is a triaryl sulfonium cation.

<4> The resist composition according to any one of <1> to <3>, wherein A$^1$ in the formula (I) is an ethylene group.

<5> The resist composition according to any one of <1> to <4>, wherein R$^2$ in the formula (I) is a C$_1$ to C$_6$ fluorinated alkyl group.

<6> The resist composition according to any one of <1> to <5>, wherein L$^{II1}$ in the formula (II) is a bond or methylene group.

<7> The resist composition according to any one of <1> to <6>, which further comprises a solvent.

<8> A method for producing a resist pattern comprising steps of;

(1) applying the resist composition of any one of <1> to <7> onto a substrate;

(2) drying the applied composition to form a composition layer;

(3) exposing the composition layer;

(4) heating the exposed composition layer, and (5) developing the heated composition layer.

DETAILED DESCRIPTION OF THE PREFERRED EMBODIMENTS

In the chemical structure formulas of the present specification, unless otherwise specified, the suitable choice of carbon number made for the exemplified substituent groups are applicable in all of the chemical structure formulas that have those same substituent groups. Unless otherwise specified, these can include any of straight-chain, branched chain, cyclic structure and a combination thereof. When there is a stereoisomeric form, all stereoisomeric forms included.

"(Meth)acrylic monomer" means at least one monomer having a structure of "CH$_2$=CH—CO—" or "CH$_2$=C(CH$_3$)—CO—", as well as "(meth)acrylate" and "(meth)acrylic acid" mean "at least one acrylate or methacrylate" and "at least one acrylic acid or methacrylic acid," respectively.

<Resist Composition>

The resist composition of the present invention contains;

a resin (hereinafter may be referred to as "resin (A)"), and an acid generator represented by the formula (II) (hereinafter may be referred to as "acid generator (II)").

Also, present resist composition preferably contains an acid generator represented by the formula (III) (hereinafter may be referred to as "acid generator (III)").

Further, the present resist composition may contain a solvent (hereinafter may be referred to as "solvent (E)") and/or an additive such as a basic compound (hereinafter may be referred to as "basic compound (C)") which is known as a quencher in this technical field, as needed.

<Resin (A)>

The resin (A) includes;

a resin having a structural unit represented by the formula (I) (hereinafter is sometimes referred to as "resin (A1)"), and a resin being insoluble or poorly soluble in alkali aqueous solution, but becoming soluble in an alkali aqueous solution by the action of an acid and not including the structural unit represented by the formula (I) (hereinafter is sometimes referred to as "resin (A2)").

Also, the resin (A) may contain a structural unit other than the resin (A1) and resin (A2).

<Resin (A1)>

The resin (A1) has a structural unit represented by the formula (I) (hereinafter may be referred to as "structural unit (I)").

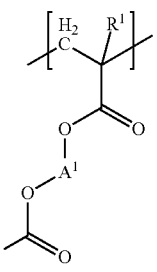

(I)

wherein R$^1$ represents a hydrogen atom or a methyl group;

A$^1$ represents a C$_1$ to C$_6$ alkanediyl group;

R$^2$ represents a C$_1$ to C$_{10}$ hydrocarbon group having a fluorine atom;

In the formula (I), examples of the alkanediyl group of A$^1$ include a chain alkanediyl group such as methylene, ethylene, propane-1,3-diyl, propane-1,2-diyl, butane-1,4-diyl, pentane-1,5-diyl, hexane-1,6-diyl; a branched alkanediyl group such as 1-methylpropane-1,3-diyl, 2-methylpropane-1,3-diyl, 2-methylpropane-1,2-diyl, 1-methylbutane-1,4-diyl, 2-methylbutane-1,4-diyl groups.

The hydrocarbon group of $R^2$ may be any of an aliphatic hydrocarbon group, an aromatic hydrocarbon group and a combination of two or more such groups. The aliphatic hydrocarbon group may be any of a chain and cyclic aliphatic hydrocarbon group, and a combination of two or more such groups. The aliphatic hydrocarbon group may include a carbon-carbon double bond, and is preferably a saturated aliphatic hydrocarbon group, i.e., an alkyl group and an alicyclic hydrocarbon group.

Examples of the alkyl group include methyl, ethyl, n-propyl, iso-propyl, n-butyl, sec-butyl, tert-butyl, iso-butyl, n-pentyl, iso-pentyl, tert-pentyl, neo-pentyl, hexyl, octyl and 2-ethylhexyl groups.

The alicyclic hydrocarbon group may be either monocyclic or polycyclic hydrocarbon group. Examples of the monocyclic alicyclic hydrocarbon group include cyclopropyl, cyclobutyl, cyclopentyl, cyclohexyl, cycloheptyl, cyclooctyl and cyclodecyl groups. Examples of the polycyclic alicyclic hydrocarbon group include decahydronaphtyl, adamantyl, 2-alkyladamantane-2-yl, 1-(adamantane-1-yl)alkane-1-yl, norbornyl, methylnorbornyl and isobornyl groups.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

The hydrocarbon group having a fluorine atom of $R^2$ is preferably an alkyl group having a fluorine atom and an alicyclic hydrocarbon group having a fluorine atom.

Examples of the alkyl group having a fluorine atom include a fluorinated alkyl group such as difluoromethyl, trifluoromethyl, 1,1-difluoroethyl, 2,2-difluoroethyl, 1,1,1-trifluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetratrifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)-2,2,3,3,3-pentafluoropropyl, perfluoropentyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl, perfluorohexyl, perfluoroheptyl and perfluorooctyl groups.

Examples of the alicyclic hydrocarbon group having a fluorine atom include a fluorinated cycloalkyl group such as perfluocyclohexyl and perfluoroadamantyl groups.

$A^1$ in the formula (I) is preferably a $C_2$ to $C_4$ alkanediyl group, and more preferably an ethylene group.

$R^2$ is preferably a fluorinated alkyl group, and more preferably a $C_1$ to $C_6$ fluorinated alkyl group.

Specific examples of the structural units (I) include as follows.

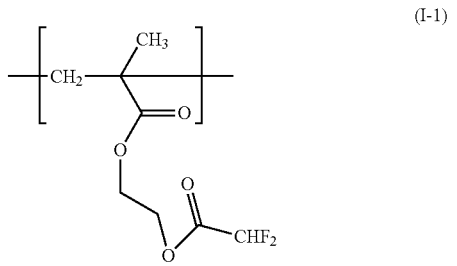

(I-1)

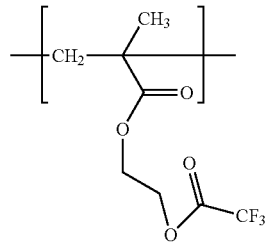

(I-2)

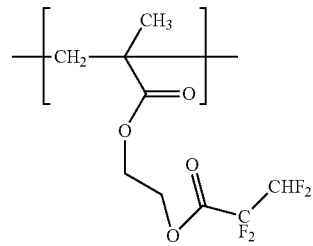

(I-3)

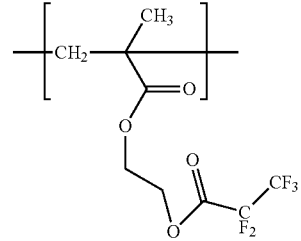

(I-4)

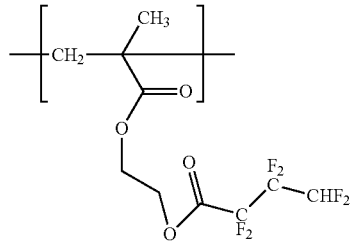

(I-5)

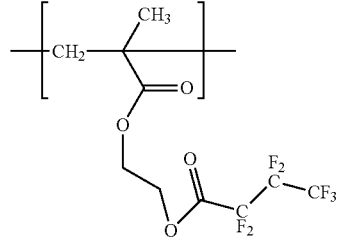

(I-6)

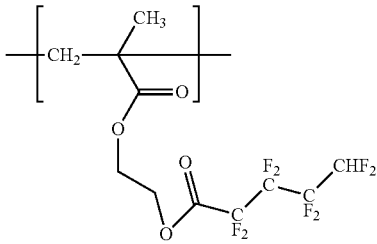

(I-7)

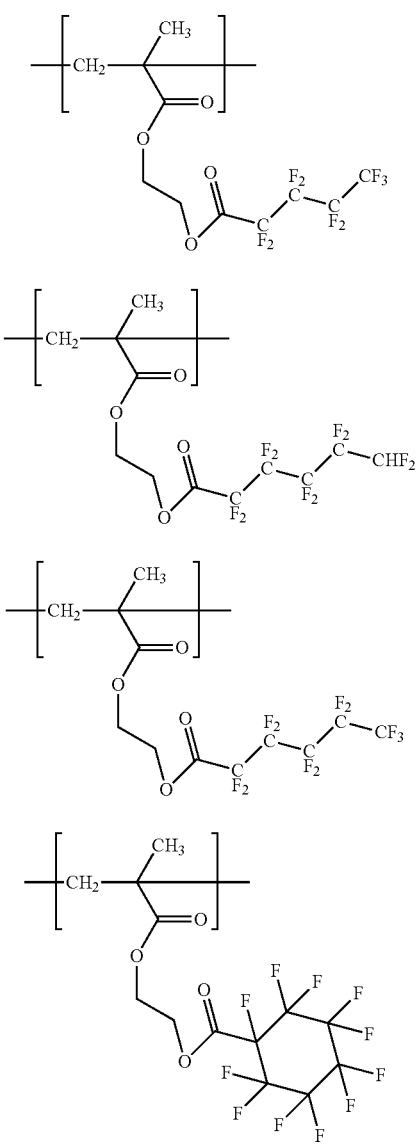

Also, examples of the structural units (I) include structural units in which a methyl group corresponding to $R^1$ in the structural units represented by the above is replaced by a hydrogen atom.

The structural unit (I) is derived from a compound represented by the formula (I'), hereinafter may be referred to as "compound (I')".

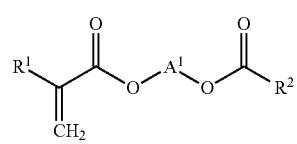

wherein $A^1$, $R^1$ and $R^2$ have the same definition of the above.

The compound (I') can be produced by a method below.

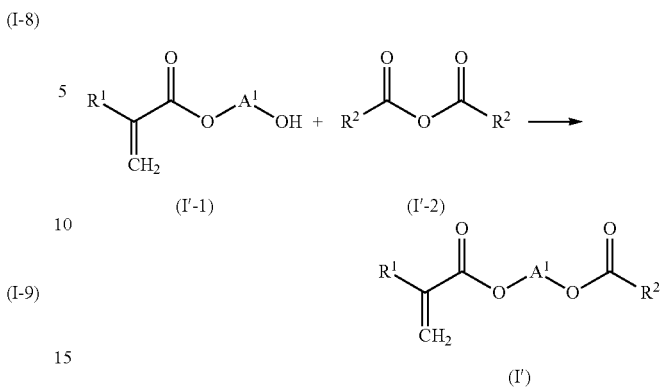

wherein $A^1$, $R^1$ and $R^2$ have the same definition of the above.

The compound (I') can be obtained by reacting a compound represented by the formula (I'-1) with a compound represented by the formula (I'-2) in presence of a basic catalyst in a solvent. Preferred examples of the basic catalyst include pyridine. Preferred examples of the solvent include tetrahydrofuran.

As the compound represented by the formula (I'-1), a marketed product may be used. The hydroxyethyl methacrylate can be used as a marketed product.

The compound represented by the formula (I'-2) can be obtained by converting corresponding carboxylic acid, depending on the kinds of $R^2$, into an anhydride. The heptafluoro butyric anhydride can be used as a marketed product.

The resin (A1) may include a structural unit other than the structural unit (I).

Examples of the structural unit other than the structural unit (I) include a structural unit derived from a monomer having an acid labile group described below (hereinafter may be referred to as "acid labile monomer (a1)"), a structural unit derived from a monomer not having an acid labile group described below (hereinafter may be referred to as "acid stable monomer"), a structural unit derived from a known monomer in this field, a structural unit represented by the formula (IIIA) described below (hereinafter is sometimes referred to as "structural unit (IIIA)"). Among these, the structural unit (IIIA) is preferable.

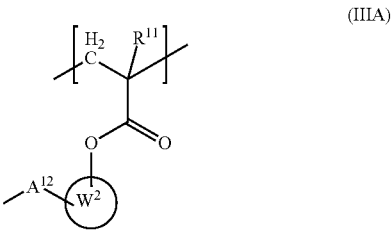

wherein $R^{11}$ represents a hydrogen atom or a methyl group; ring $W^2$ represents a $C_6$ to $C_{10}$ hydrocarbon ring;
$A^{12}$ represents —O—, *—CO—O— or *—O—CO—, * represents a bond to ring $W^2$;
$R^{12}$ represents a $C_1$ to $C_6$ alkyl group having a fluorine atom.

The hydrocarbon ring of the ring $W^2$ may be an alicyclic hydrocarbon ring, and preferably a saturated alicyclic hydrocarbon ring.

Examples of the saturated aliphatic hydrocarbon ring include a ring below.

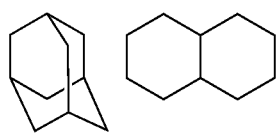

As the ring $W^2$, an adamantane ring and cyclohexane ring are preferable, and an adamantane ring is more preferable.

Examples of the alkyl group having a fluorine atom of the $R^{12}$ include a fluorinated alkyl group such as, groups described below, difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)-2,2,3,3,3-pentafluoropropyl, perfluoropentyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

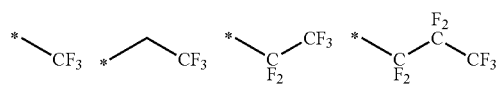
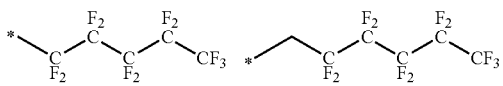

Examples of the structural unit represented by the formula (IIIA) include structural units below.

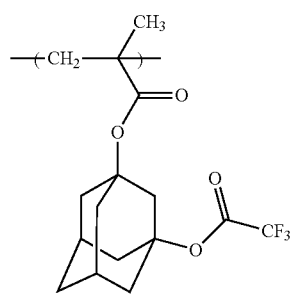
(IIIA-1)

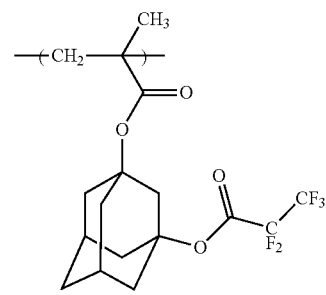
(IIIA-2)

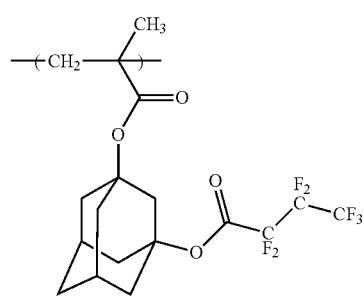
(IIIA-3)

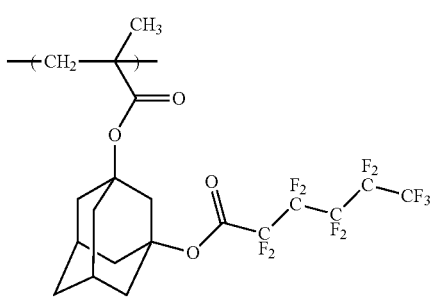
(IIIA-4)

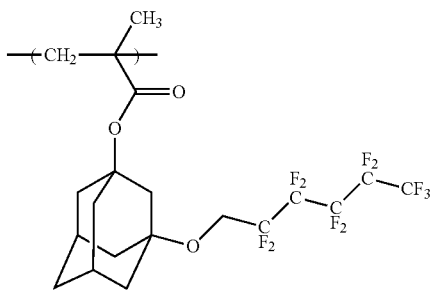
(IIIA-5)

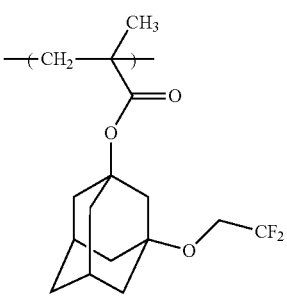
(IIIA-6)

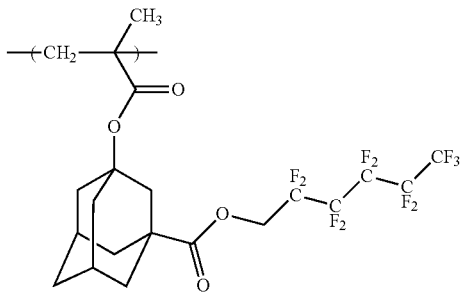

(IIIA-7)

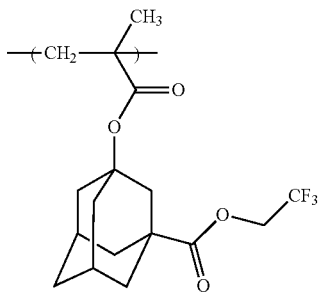

(III-8)

Also, examples of the structural units (IIIA) include structural units in which a methyl group corresponding to $R^{11}$ in the structural units represented by the above is replaced by a hydrogen atom.

Among these, the structural unit (IIIA-1) and the structural unit (IIIA-1) in which a methyl group corresponding to $R^{11}$ in the structural unit (IIIA-1) represented by the above is replaced by a hydrogen atom are preferable.

The proportion of the structural unit (I) in the resin (A1) is generally 5 to 100 mol %, preferably 10 to 100 mol %, more preferably 50 to 100 mol %, still more preferably 80 to 100 mol %, and, in particular, preferably almost 100 mol %, with respect to the total structural units (100 mol %) constituting the resin (A1).

Within the proportion of the structural unit (I), it is possible to produce a resist pattern with defect-free.

When the resin (A1) contains the structural unit (IIIA), the proportion thereof in the resin (A1) is generally 1 to 95 mol %, preferably 2 to 80 mol %, more preferably 5 to 70 mol %, still more preferably 5 to 50 mol % and in particular preferably 5 to 30 mol %, with respect to the total structural units (100 mol %) constituting the resin (A1).

For achieving the proportion of the structural unit (I) and/or the structural unit (IIIA) in the resin (A1) within the above range, the amount of the compound (I') and/or a monomer giving the structural unit (IIIA) to be used can be adjusted with respect to the total amount of the monomer to be used when the resin (A1) is produced (the same shall apply hereinafter for corresponding adjustment of the proportion).

The resin (A1) can be produced by a known polymerization method, for example, radical polymerization method, using at least one of the compound (I') and/or at least one of the monomer giving the structural unit (IIIA), and optionally at least one of the acid labile monomer (a1), at least one of the acid stable monomer and/or at least one of a known compound.

The weight average molecular weight of the resin (A) is preferably 5,000 or more (more preferably 7,000 or more, and still more preferably 10,000 or more), and 80,000 or less (more preferably 50,000 or less, and still more preferably 30,000 or less).

The weight average molecular weight is a value determined by gel permeation chromatography using polystyrene as the standard product. The detailed condition of this analysis is described in Examples.

<Resin (A2)>

The resin (A2) is a resin having properties which is insoluble or poorly soluble in alkali aqueous solution, but becomes soluble in an alkali aqueous solution by the action of an acid. Here "a resin becoming soluble in an alkali aqueous solution by the action of an acid" means a resin that has an acid labile group and is insoluble or poorly soluble in aqueous alkali solution before contact with the acid, and becomes soluble in aqueous alkali solution after contact with an acid.

Therefore, the resin (A2) is preferably a resin having at least one structural unit derived from an acid labile monomer (a1).

Also, the resin (A2) may include a structural unit other than the structural unit having the acid labile group as long as the resin (A2) has above properties and does not have the structural unit (I).

Examples of the structural unit other than the structural unit having the acid labile group include a structural unit derived from the acid stable monomer, the structural unit derived from a known monomer in this field, the structural units represented by the formula (IIIA) described above.

<Acid Labile Monomer (a1)>

The "acid labile group" means a group which has an elimination group and in which the elimination group is detached by contacting with an acid resulting in forming a hydrophilic group such as a hydroxy or carboxy group. Examples of the acid labile group include a group represented by the formula (1) and a group represented by the formula (2). Hereinafter a group represented by the formula (1) may refer to as an "acid labile group (1)", and a group represented by the formula (2) may refer to as an "acid labile group (2)".

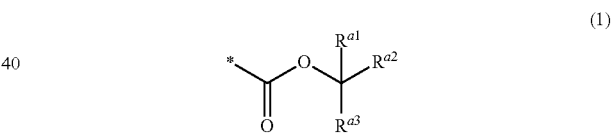

(1)

wherein $R^{a1}$ to $R^{a3}$ independently represent a $C_1$ to $C_8$ alkyl group or a $C_3$ to $C_{20}$ alicyclic hydrocarbon group, or $R^{a1}$ and $R^{a2}$ may be bonded together to form a $C_2$ to $C_{20}$ divalent hydrocarbon group, * represents a bond. In particular, the bond here represents a bonding site (the similar shall apply hereinafter for "bond").

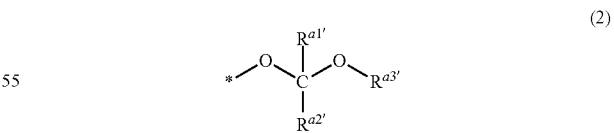

(2)

wherein $R^{a1'}$ and $R^{a2'}$ independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a3'}$ may be bonded together to form a divalent $C_2$ to $C_{20}$ hydrocarbon group, and one or more —$CH_2$— contained in the hydrocarbon group or the divalent hydrocarbon group may be replaced by —O— or —S—, * represents a bond.

Examples of the alkyl group of $R^{a1}$ to $R^{a3}$ include methyl, ethyl, propyl, butyl, pentyl and hexyl groups.

Examples of the alkyl group of $R^{a1}$ to $R^{a3}$ include methyl, ethyl, propyl, butyl, pentyl and hexyl groups.

Examples of the alicyclic hydrocarbon group of $R^{a1}$ to $R^{a3}$ include monocyclic hydrocarbon groups such as a cycloalkyl group, i.e., cyclopentyl, cyclohexyl, methylcyclohexyl, dimethylcyclohexyl, cycloheptyl, cyclooctyl groups; and polycyclic hydrocarbon groups such as decahydronaphtyl, adamantyl, norbornyl (i.e., bicyclo[2.2.1]heptyl), and methyl norbornyl groups as well as groups below.

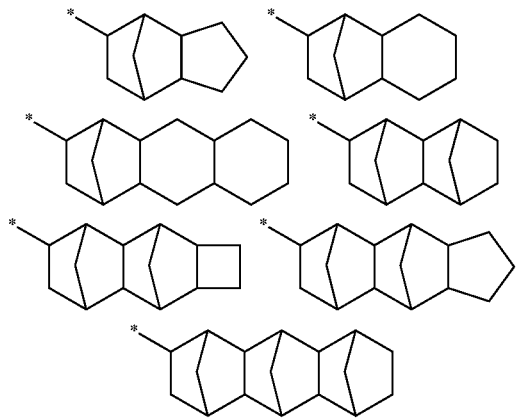

The hydrogen atom contained in the alicyclic hydrocarbon group of $R^{a1}$ to $R^{a3}$ may be replaced an alkyl group. In this case, the carbon number of the alicyclic hydrocarbon group is comparable to the total carbon number of the alkyl group and the alicyclic hydrocarbon group.

The alicyclic hydrocarbon group of $R^{a1}$ to $R^{a3}$ preferably has 3 to 16 carbon atoms, and more preferably has 4 to 16 carbon atoms.

When $R^{a1}$ and $R^{a2}$ is bonded together to form a $C_2$ to $C_{20}$ hydrocarbon group, examples of the group-$C(R^{a1})(R^{a2})(R^{a3})$ include groups below. The divalent hydrocarbon group preferably has 3 to 12 carbon atoms. * represents a bond to —O—.

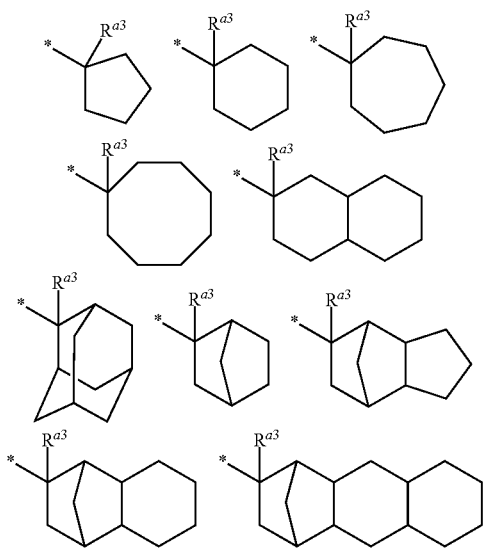

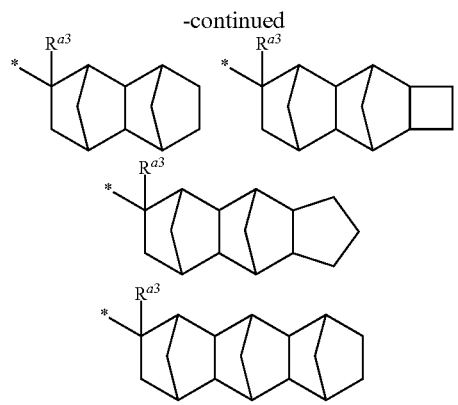

Specific examples of the acid labile group (1) include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$, $R^{a2}$ and a carbon atom form adamantyl group, and $R^{a3}$ is alkyl group, in the formula (1)), and 1-(adamantane-1-yl)-1-alkylalkoxycarbonyl group (a group in which $R^{a1}$ and $R^{a2}$ are alkyl group, and $R^{a3}$ is adamantyl group, in the formula (1)).

The hydrocarbon group of $R^{a1'}$ to $R^{a3'}$ includes any of an alkyl group, an alicyclic hydrocarbon group and an aromatic hydrocarbon group.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the divalent hydrocarbon group which is formed by bonding with $R^{a2'}$ and $R^{a3'}$ include a divalent aliphatic hydrocarbon group.

At least one of $R^{a1'}$ and $R^{a2'}$ is preferably a hydrogen atom.

Specific examples of the acid labile group (2) include a group below.

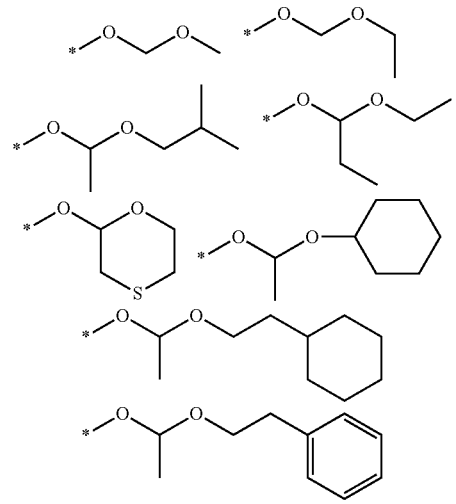

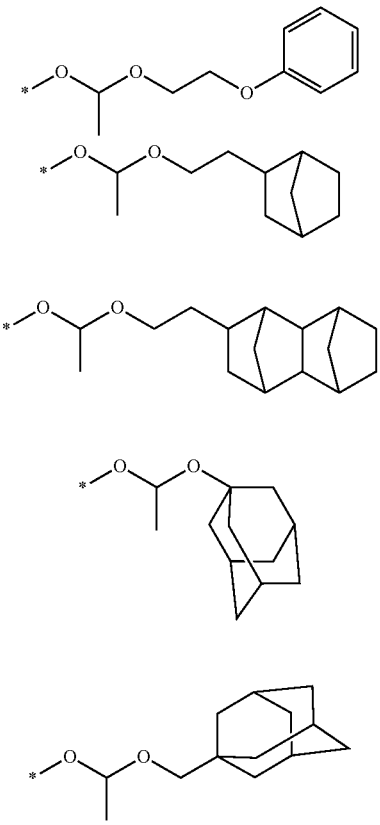

The acid labile monomer (a1) is preferably a monomer having an acid labile group and a carbon-carbon double bond, and more preferably a (meth)acrylic monomer having the acid labile group.

Among the (meth)acrylic monomer having an acid labile group, it is preferably a monomer having a $C_5$ to $C_{20}$ alicyclic hydrocarbon group. When a resin which can be obtained by polymerizing monomers having bulky structure such as the alicyclic hydrocarbon group is used, the resist composition having excellent resolution tends to be obtained during the production of a resist pattern.

Examples of the (meth)acrylic monomer having the acid labile group (1) and a carbon-carbon double bond preferably include a monomer represented by the formula (a1-1) and a monomer represented by the formula (a1-2), below (hereinafter are sometimes referred to as a "monomer (a1-1)" and a "monomer (a1-2)"). These may be used as a single monomer or as a combination of two or more monomers.

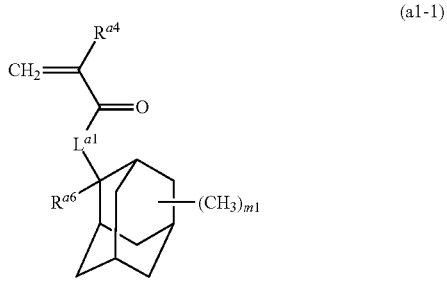
(a1-1)

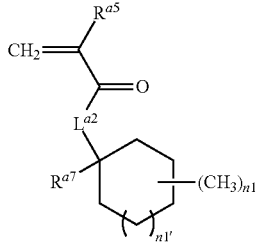
(a1-2)

wherein $L^{a1}$ and $L^{a2}$ independently represent *—O— or *—O—$(CH_2)_{k1}$—CO—O—, k1 represents an integer of 1 to 7, * represents a bond to the carbonyl group;

$R^{a4}$ and $R^{a5}$ independently represent a hydrogen atom or a methyl group;

$R^{a6}$ and $R^{a7}$ independently represent a $C_1$ to $C_8$ alkyl group or a $C_3$ to $C_{10}$ alicyclic hydrocarbon group;

m1 represents an integer 0 to 14;

n1 represents an integer 0 to 10; and n1' represents an integer 0 to 3.

In the formula (a1-1) and the formula (a1-2), $L^{a1}$ and $L^{a2}$ are preferably *—O— or *—O—$(CH_2)_{k1'}$—CO—O—, here k1' represents an integer of 1 to 4 and more preferably 1, and more preferably *—O.

$R^{a4}$ and $R^{a5}$ are preferably a methyl group.

Examples of the alkyl group of $R^{a6}$ and $R^{a7}$ include methyl, ethyl, propyl, butyl, pentyl, hexyl and octyl groups. Among these, the alkyl group of $R^{a6}$ and $R^{a7}$ is preferably a $C_1$ to $C_6$ alkyl group.

Examples of the alicyclic hydrocarbon group of $R^{a6}$ and $R^{a7}$ include monocyclic hydrocarbon groups such as cyclopentyl, cyclohexyl, methylcyclohexyl, dimethylcyclohexyl, cycloheptyl, cyclooctyl groups; and polycyclic hydrocarbon groups such as decahydronaphtyl, adamantyl, norbornyl (i.e., bicyclo[2.2.1]heptyl), and methyl norbornyl groups as well as groups above. Among these, the alicyclic hydrocarbon group of $R^{a6}$ and $R^{a7}$ is preferably a $C_3$ to $C_8$ alicyclic hydrocarbon group, and more preferably a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1, and more preferably 1.

Examples of the monomer (a1-1) include monomers described in JP 2010-204646A. Among these, the monomers are preferably monomers represented by the formula (a1-1-1) to the formula (a1-1-8), and more preferably monomers represented by the formula (a1-1-1) to the formula (a1-1-4) below.

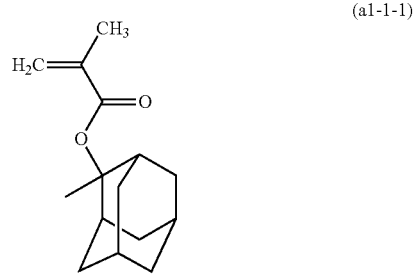
(a1-1-1)

(a1-1-2) 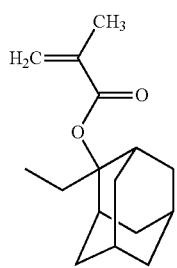

(a1-1-3) 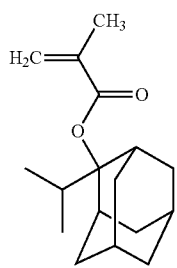

(a1-1-4) 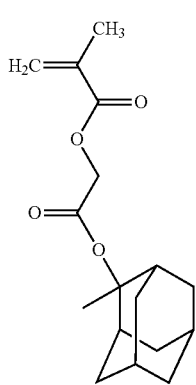

(a1-1-5) 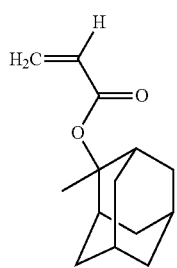

(a1-1-6) 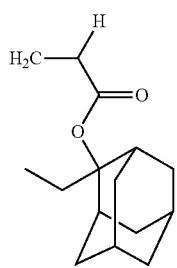

(a1-1-7) 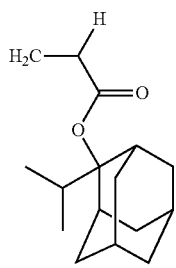

(a1-1-8) 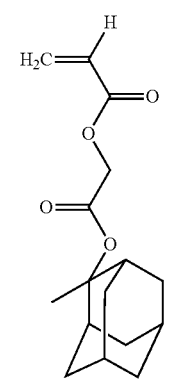

Examples of the monomer (a1-2) include 1-ethyl-1-cyclopentane-1-yl(meth)acrylate, 1-ethyl-1-cyclohexane-1-yl(meth)acrylate, 1-ethyl-1-cycloheptane-1-yl(meth)acrylate, 1-methyl-1-cyclopentane-1-yl(meth)acrylate and 1-isopropyl-1-cyclopentane-1-yl(meth)acrylate. Among these, the monomers are preferably monomers represented by the formula (a1-2-1) to the formula (a1-2-12), and more preferably monomers represented by the formula (a1-2-3), the formula (a1-2-4), the formula (a1-2-9) and the formula (a1-2-10), and still more preferably monomers represented by the formula (a1-2-3) and the formula (a1-2-9) below.

(a1-2-1) 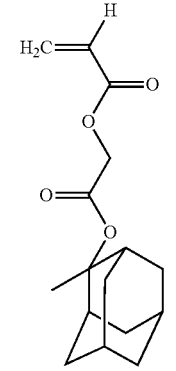

(a1-2-2) 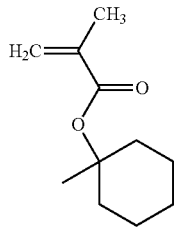

(a1-2-3)
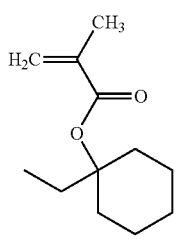

(a1-2-4)
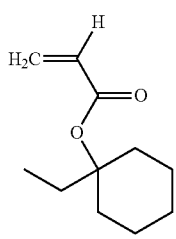

(a1-2-5)
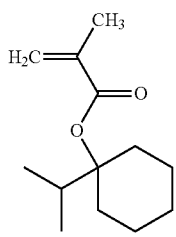

(a1-2-6)
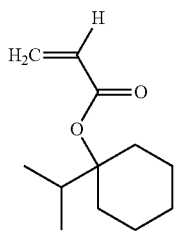

(a1-2-7)
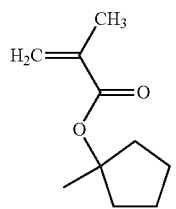

(a1-2-8)
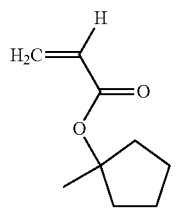

(a1-2-9)
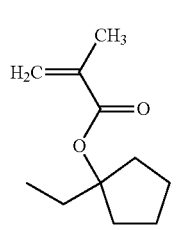

(a1-2-10)
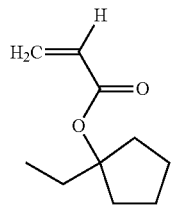

(a1-2-11)
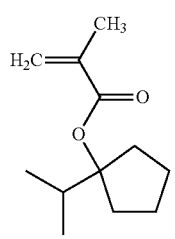

(a1-2-12)
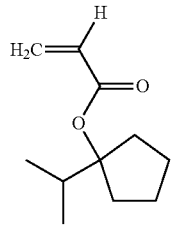

When the resin (A2) contains the structural unit (a1-1) and/or the structural unit (a1-2), the total proportion thereof is generally to 95 mol %, preferably 15 to 90 mol %, more preferably 20 to 85 mol %, with respect to the total structural units (100 mol %) of the resin (A2).

Examples of a monomer having an acid-labile group (2) and a carbon-carbon double bond include a monomer represented by the formula (a1-5). Such monomer is sometimes hereinafter referred to as "monomer (a1-5)". When the resin (A2) has the structural unit derived from the monomer (a1-5), a resist pattern tends to be obtained with less defects.

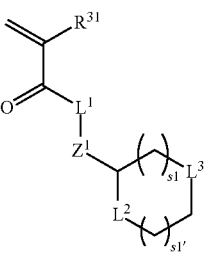
(a1-5)

wherein $R^{31}$ represents a hydrogen atom, a halogen atom or a $C_1$ to $C_6$ alkyl group that optionally has a halogen atom;

$Z^1$ represents a single bond or *—O—(CH$_2$)$_{k4}$—CO-L$^4$-, k4 represents an integer of 1 to 4, * represents a bond to $L^1$;

$L^1$, $L^2$, $L^3$ and $L^4$ independently represent *—O— or *—S—.

s1 represents an integer of 1 to 3;

s1' represents an integer of 0 to 3.

In the formula (a1-5), $R^{31}$ is preferably a hydrogen atom, a methyl group or trifluoromethyl group;

$L^1$ is preferably —O—;

$L^2$ and $L^3$ are independently preferably *—O— or *—S—, and more preferably —O— for one and —S— for another;

s1 is preferably 1;
s1' is preferably an integer of 0 to 2;
$Z^1$ is preferably a single bond or —$CH_2$—CO—O—.
Examples of the monomer (a1-5) include monomers below.
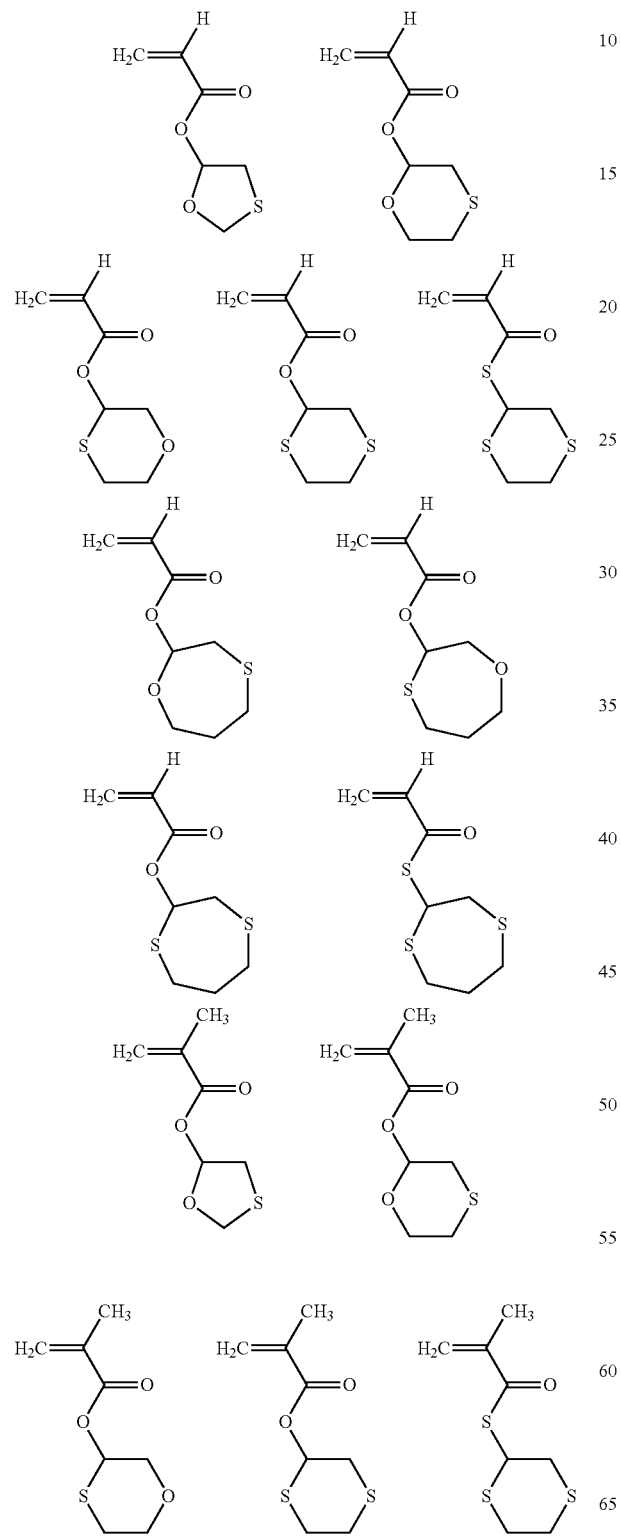
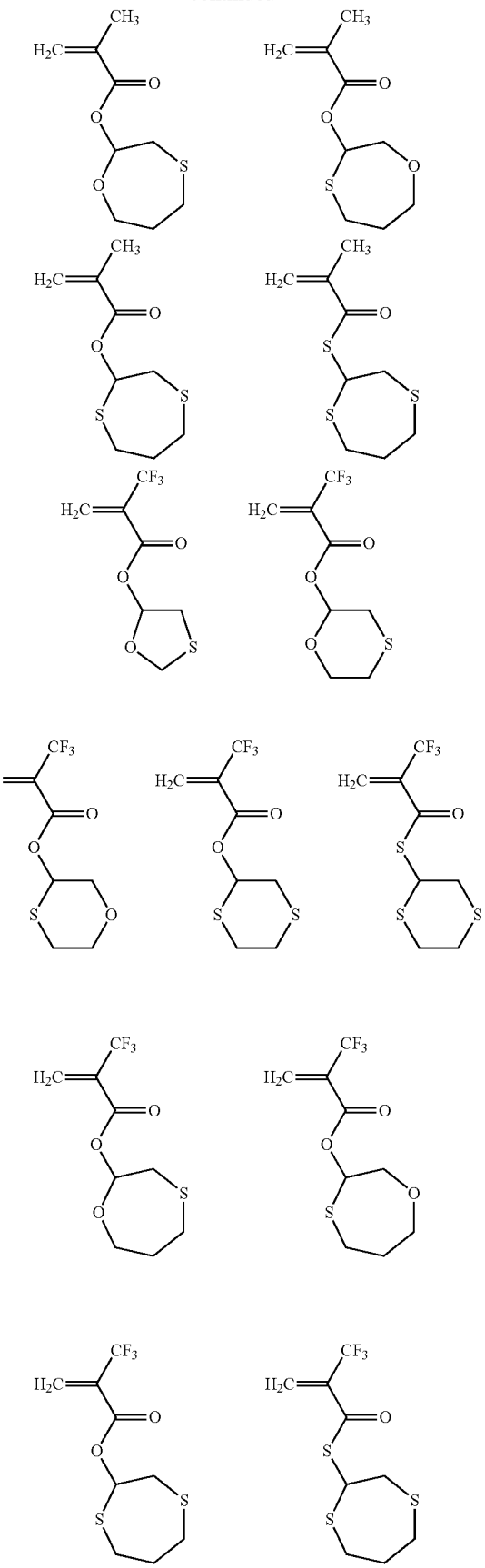

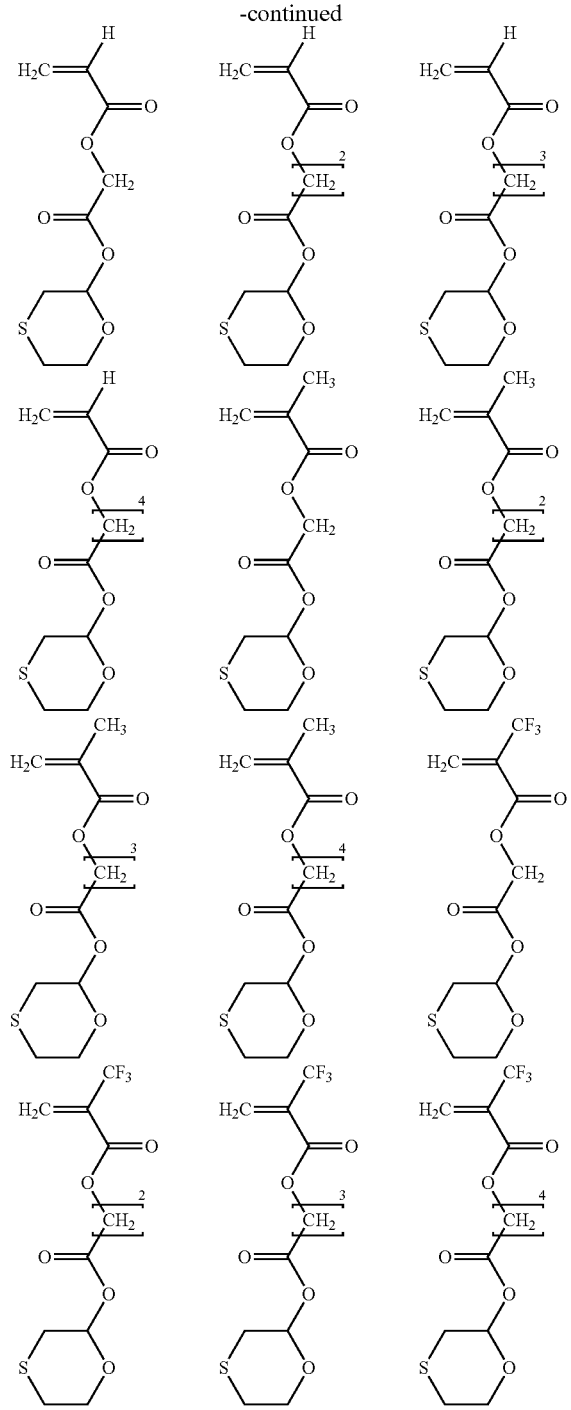

When the resin (A2) contains the structural unit derived from the monomer (a1-5), the proportion thereof is generally 1 to 50 mol %, preferably 3 to 45 mol %, and more preferably 5 to 40 mol %, with respect to the total structural units (100 mol %) constituting the resin (A2).

<Acid Stable Monomer>

As the acid stable monomer, a monomer having a hydroxy group or a lactone ring is preferable. When a resin containing the structural unit derived from a monomer having hydroxy group (hereinafter such acid stable monomer is sometimes referred to as "acid stable monomer (a2)") or a acid stable monomer having a lactone ring (hereinafter such acid stable monomer is sometimes referred to as "acid stable monomer (a3)") is used, the adhesiveness of resist pattern to a substrate and resolution of resist pattern tend to be improved.

<Acid Stable Monomer (a2)>

The acid stable monomer (a2), which has a hydroxy group, is preferably selected depending on the kinds of an exposure light source at producing the resist pattern.

When KrF excimer laser lithography (248 nm), or high-energy irradiation such as electron beam or EUV light is used for the resist composition, using the acid stable monomer having a phenolic hydroxy group such as hydroxystyrene as the acid stable monomer (a2) is preferable.

When ArF excimer laser lithography (193 nm), i.e., short wavelength excimer laser lithography is used, using the acid stable monomer having a hydroxy adamantyl group represented by the formula (a2-1) as the acid stable monomer (a2) is preferable.

The acid stable monomer (a2) having the hydroxy group may be used as a single monomer or as a combination of two or more monomers.

Examples of the acid stable monomer having hydroxy adamantyl include the monomer represented by the formula (a2-1).

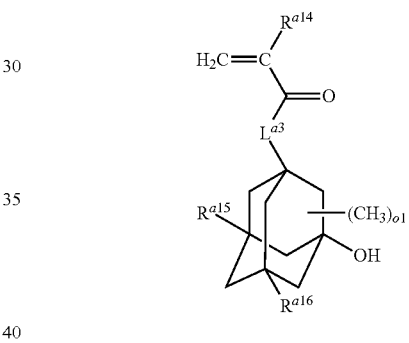

(a2-1)

wherein $L^{a3}$ represents —O— or *—O—$(CH_2)_{k2}$—CO—O—;

k2 represents an integer of 1 to 7;

* represents a bind to —CO—;

$R^{a14}$ represents a hydrogen atom or a methyl group;

$R^{a15}$ and $R^{a16}$ independently represent a hydrogen atom, a methyl group or a hydroxy group;

o1 represents an integer of 0 to 10.

In the formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$R^{a16}$ is preferably a hydrogen atom or a hydroxy group.

o1 is preferably an integer of 0 to 3, and more preferably an integer of 0 or 1.

Examples of the acid stable monomer (a2-1) include monomers described in JP 2010-204646A. Among these, the monomers are preferably monomers represented by the formula (a2-1-1) to the formula (a2-1-6), more preferably monomers represented by the formula (a2-1-1) to the formula (a2-1-4), and still more preferably monomers represented by the formula (a2-1-1) and the formula (a2-1-3) below.

(a2-1-1) 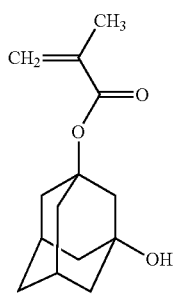

(a2-1-2) 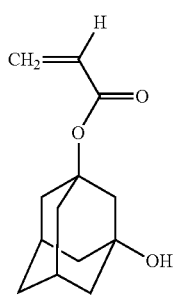

(a2-1-3) 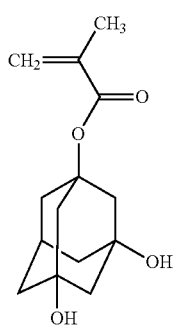

(a2-1-4) 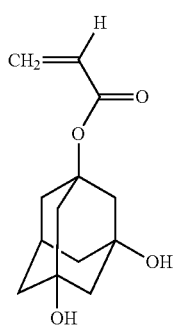

(a2-1-5) 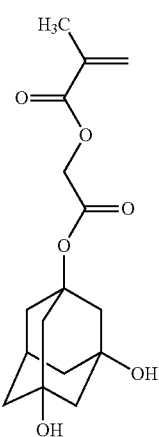

(a2-1-6) 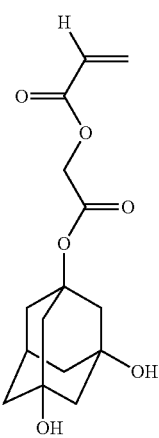

When the resin (A2) contains the acid stable structural unit derived from the monomer represented by the formula (a2-1), the proportion thereof is generally 3 to 45 mol %, preferably 5 to 40 mol %, more preferably 5 to 35 mol %, and still more preferably 5 to 30 mol %, with respect to the total structural units (100 mol %) constituting the resin (A2).

<Acid Stable Monomer (a3)>

The lactone ring included in the acid stable monomer (a3) may be a monocyclic compound such as β-propiolactone ring, γ-butyrolactone, δ-valerolactone, or a condensed ring with monocyclic lactone ring and other ring. Among these, γ-butyrolactone and condensed ring with γ-butyrolactone and other ring are preferable.

Examples of the acid stable monomer (a3) having the lactone ring include monomers represented by the formula (a3-1), the formula (a3-2) and the formula (a3-3). These monomers may be used as a single monomer or as a combination of two or more monomers.

(a3-1) 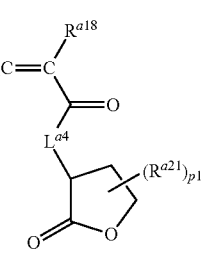

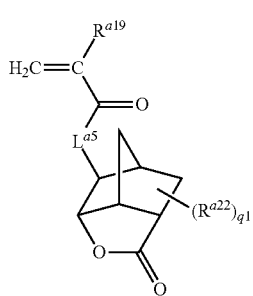

(a3-2)

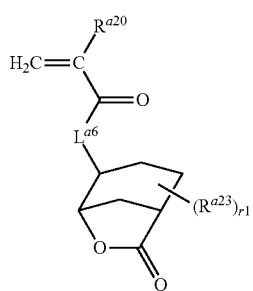

(a3-3)

wherein $L^{a4}$ to $L^{a6}$ independently represent —O— or *—O—$(CH_2)_{k3}$—CO—O—;

k3 represents an integer of 1 to 7, * represents a bind to —CO—;

$R^{a18}$ to $R^{a20}$ independently represent a hydrogen atom or a methyl group;

$R^{a21}$ in each occurrence represents a $C_1$ to $C_4$ alkyl group;

p1 represents an integer of 0 to 5;

$R^{a22}$ to $R^{a23}$ in each occurrence independently represent a carboxyl group, cyano group, and a $C_1$ to $C_4$ alkyl group;

q1 and r1 independently represent an integer of 0 to 3.

In the formulae (a3-1) to (a3-3), $L^{a4}$ to $L^{a6}$ include the same group as described in $L^{a3}$ above, and are independently preferably —O—, *—O—$(CH_2)_{k3'}$—CO—O—, here k3' represents an integer of 1 to 4 (preferably 1), and more preferably —O—;

$R^{a18}$ to $R^{a21}$ are independently preferably a methyl group.

$R^{a22}$ and $R^{a23}$ are independently preferably a carboxyl group, cyano group or methyl group;

p1 to r1 are independently preferably an integer of 0 to 2, and more preferably an integer of 0 or 1.

Examples of the monomer (a3) include monomers described in JP 2010-204646A. Among these, the monomers are preferably monomers represented by the formula (a3-1-1) to the formula (a3-1-4), the formula (a3-2-1) to the formula (a3-2-4), the formula (a3-3-1) to the formula (a3-3-4), more preferably monomers represented by the formula (a3-1-1) to the formula (a3-1-2), the formula (a3-2-3) to the formula (a3-2-4), and still more preferably monomers represented by the formula (a3-1-1) and the formula (a3-2-3) below.

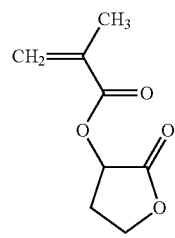

(a3-1-1)

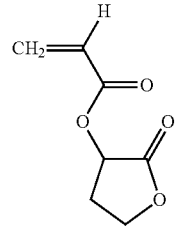

(a3-1-2)

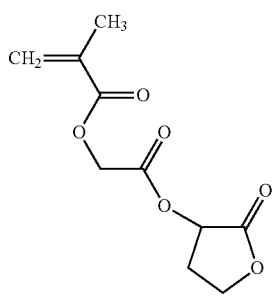

(a3-1-3)

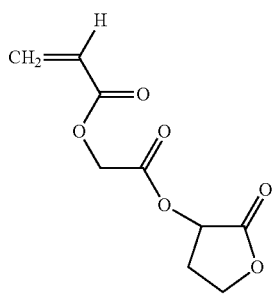

(a3-1-4)

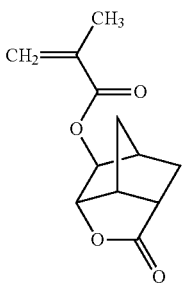

(a3-2-1)

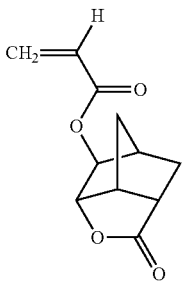

(a3-2-2)

(a3-2-3)

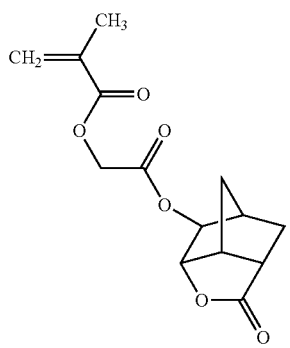

(a3-2-4)

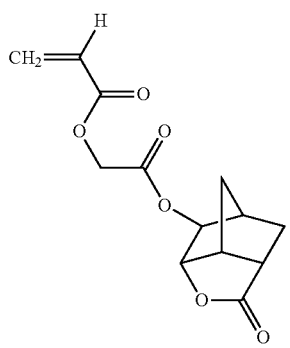

(a3-3-1)

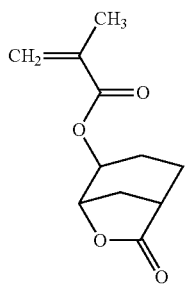

(a3-3-2)

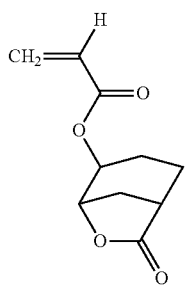

(a3-3-3)

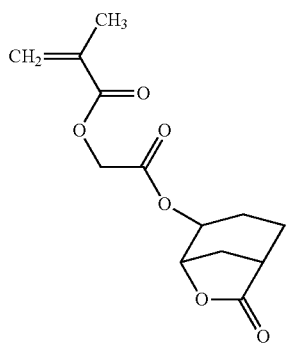

(a3-3-4)

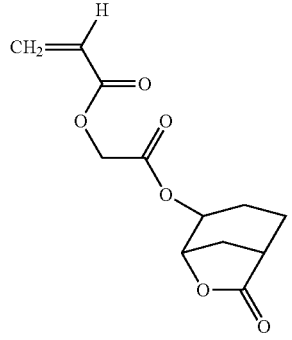

When the resin (A2) contains the structural units derived from the acid stable monomer (a3) having the lactone ring, the total proportion thereof is preferably 5 to 70 mol %, more preferably 10 to 65 mol %, still more preferably 15 to 60 mol %, with respect to the total structural units (100 mol %) constituting the resin (A2).

When the resin (A2) is the copolymer of the acid labile monomer (a1) and the acid stable monomer, the proportion of the structural unit derived from the acid labile monomer (a1) is preferably 10 to 80 mol %, and more preferably 20 to 60 mol %, with respect to the total structural units (100 mol %) constituting the resin (A2).

The proportion of the structural unit derived from the monomer having an adamantyl group (in particular, the monomer having the acid labile group (a1-1)) is preferably 15 mol % or more with respect to the structural units derived from the acid labile monomer (a1). As the mole ratio of the structural unit derived from the monomer having an adamantyl group increases within this range, the dry etching resistance of the resulting resist improves.

The resin (A2) preferably is a copolymer of the acid labile monomer (a1) and the acid stable monomer. In this copolymer, the acid labile monomer (a1) is preferably at least one of the acid labile monomer (a1-1) having an adamantyl group and the acid labile monomer (a1-2) having a cyclohexyl group, and more preferably is the acid labile monomer (a1-1).

The acid stable monomer is preferably the acid stable monomer (a2) having a hydroxy group and/or the acid stable monomer (a3) having a lactone ring. The acid stable monomer (a2) is preferably the monomer having the hydroxyadamantyl group (a2-1).

The acid stable monomer (a3) is preferably at least one of the monomer having the γ-butyrolactone ring (a3-1) and the monomer having the condensed ring of the γ-butyrolactone ring and the norbornene ring (a3-2).

The resin (A2) can be produced by a known polymerization method, for example, radical polymerization method, using at least one of the acid labile monomer (a1) and/or at least one of the acid stable monomer (a2) having a hydroxy group and/or at least one of the acid stable monomer (a3) having a lactone ring and/or at least one of a known compound.

The weight average molecular weight of the resin (A2) is preferably 2,500 or more (more preferably 3,000 or more, and still more preferably 4,000 or more), and 50,000 or less (more preferably 30,000 or less, and still more preferably 10,000 or less).

In the present resist composition, the weight ratio of the resins (A1)/(A2) (weight ratio) is preferably, for example, 0.01/10 to 5/10, more preferably 0.05/10 to 3/10, still more preferably 0.1/10 to 2/10, in particular, preferably 0.2/10 to 1/10.

<Resin Other than Resin (A1) and Resin (A2)>

The resist composition of the present invention may include a resin other than the resin (A1) and the resin (A2) described above. Such resin is a resin having at least one of the structural unit derived from the acid labile monomer (a1), at least one of the structural unit derived from the acid stable monomer, as described above, and/or at least one of the structural unit derived from a known monomer in this field.

The proportion of the resin (A) can be adjusted with respect to the total solid proportion of the resist composition. For example, the resist composition of the present invention preferably contains 80 weight % or more and 99 weight % or less of the resin (A), with respect to the total solid proportion of the resist composition.

In the specification, the term "solid proportion of the resist composition" means the entire proportion of all ingredients other than the solvent (E). For example, if the proportion of the solvent (E) is 90 weight %, the solid proportion of the resist composition is weight %.

The proportion of the resin (A) and the solid proportion of the resist composition can be measured with a known analytical method such as, for example, liquid chromatography and gas chromatography.

<Acid Generator (II)>

The acid generator (II) included in the resist composition of the present invention includes a salt represented by the formula (II);

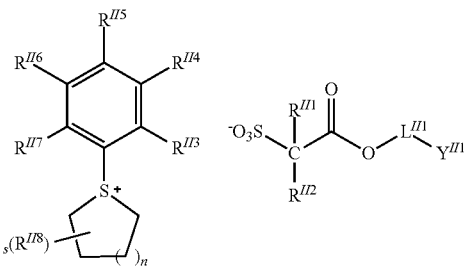

(II)

wherein $R^{II1}$ and $R^{II2}$ independently represent a fluorine atom or a $C_1$ to $C_6$ perfluoroalkyl group;

$L^{II1}$ represents a single bond, a $C_1$ to $C_6$ alkanediyl, a $C_4$ to $C_8$ divalent alicyclic hydrocarbon group, —$(CH_2)_t$—CO—O—* or —$(CH_2)_t$—CO—O—$CH_2$—$(CH_2)_u$—*, one or more —$CH_2$— contained in the alkanediyl, —$(CH_2)_t$—CO—O—* or —$(CH_2)_t$—CO—O—$CH_2$—$(CH_2)_u$—* may be replaced by —O—, t represents an integer of 1 to 12, u represents an integer of 0 to 12, * represents a bond to $Y^{II1}$;

$Y^{II1}$ represents an optionally substituted $C_3$ to $C_{18}$ alicyclic hydrocarbon group, and one or more —$CH_2$— contained in the alicyclic hydrocarbon group may be replaced by —O—, —CO— or —$SO_2$—;

$R^{II3}$, $R^{II4}$, $R^{II5}$, $R^{II6}$ and $R^{II7}$ independently represent a hydrogen atom, a hydroxy group, a $C_1$ to $C_6$ alkyl group, a $C_1$ to $C_6$ alkoxy group, a $C_2$ to $C_7$ alkoxycarbonyl group or a $C_2$ to $C_{12}$ acyloxy group, one or more —$CH_2$— contained in sulfur-containing ring of cation may be replaced by —O— or —CO—;

n represents an integer of 1 to 3;

s represents an integer of 0 to 3; and $R^{II8}$ in each occurrence independently represent a $C_1$ to $C_6$ alkyl group.

In the formula (II), a moiety having a positive charge sometimes refer to as an organic cation, and a moiety having a negative charge sometimes refer to as a sulfonate anion.

Examples of the perfluoroalkyl group of $R^{II1}$ and $R^{II2}$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

Among these, $R^{II1}$ and $R^{II2}$ independently are preferably trifluoromethyl or fluorine atom, and more preferably a fluorine atom.

The alkanediyl group of $L^{II1}$ may be any of a linear chain alkanediyl group and a branched chain alkanediyl group.

Specific examples of the linear chain alkanediyl group include methylene, ethylene, propane-1,3-diyl, propane-1,2-diyl, butane-1,4-diyl, pentane-1,5-diyl and hexane-1,6-diyl groups.

Specific examples of the branched chain alkanediyl group include a group in which a linear chain alkanediyl group has a side chain of an alkyl group (especially a $C_1$ to $C_4$ alkyl group such as methyl, ethyl, propyl, isopropyl, butyl, sec-butyl, tert-butyl groups) such as butan-1,3-diyl, 2-methylpuropane-1,3-diyl, 2-methylpuropane-1,2-diyl, pentan-1,4-diyl and 2-methylbutane-1,4-diyl groups.

Examples of the alkanediyl in which one or more —$CH_2$— contained in the alkanediyl is replaced by —O— include —$CH_2$—O—, —$CH_2$—$CH_2$—O—, —$CH_2$—$CH_2$—$CH_2$—O— and —$CH_2$—$CH_2$—O—$CH_2$—, among these, —$CH_2$—$CH_2$—O— is preferable.

Examples of divalent alicyclic hydrocarbon group of $L^{II1}$ include cycloalkanediyl group such as cyclobutan-1,3-diyl, cyclopenthan-1,3-diyl, cyclohexan-1,2-diyl, 1-methylcyclohexan-1,2-diyl, cyclohexan-1,4-diyl, cyclooctan-1,2-diyl and cyclooctan-1,5-diyl groups.

Examples of —$(CH_2)_t$—CO—O—* of $L^{II1}$ include —$CH_2$—CO—O—*, —$(CH_2)_2$—CO—O—*, —$(CH_2)_3$—CO—O—*, —$(CH_2)_4$—CO—O—*, —$(CH_2)_6$—CO—O—* and —$(CH_2)_8$—CO—O—*, among these, —$CH_2$—CO—O—* and —$(CH_2)_2$—CO—O—* are preferable.

Examples of —$(CH_2)_t$—CO—O—$CH_2$—$(CH_2)_u$—* of $L^{II1}$ include —$CH_2$—CO—O—$CH_2$—*, —$CH_2$—CO—O—$CH_2$—$CH_2$—*, —$CH_2$—CO—O—$CH_2$—$(CH_2)_2$—*, —$CH_2$—CO—O—$CH_2$—$CH_2$—O—* and —$CH_2$—CO—O—$CH_2$—$CH_2$—O—$CH_2$—*

For $L^{II1}$, a single bond or a $C_1$ to $C_6$ alkanediyl group is preferable, and a single bond or a methylene group is more preferable.

Examples of the alicyclic hydrocarbon group of $Y^{II1}$ include monocyclic and polycyclic cycloalkyl groups represented by the formula (Y1) to the formula (Y11). The cycloalkyl groups also include groups in which a $C_1$ to $C_{12}$ alkyl group is bonded to the atom constituting the ring, for example, groups represented by the formula (Y27) to the formula (Y29). The alicyclic hydrocarbon group is preferably a $C_3$ to $C_{12}$ cycloalkyl group.

Examples of the substituent of $Y^{II1}$ include a halogen atom (other than fluorine atom), a hydroxy group, a $C_1$ to $C_{12}$ alkoxy group, a $C_6$ to $C_{18}$ aromatic hydrocarbon group, a $C_7$ to $C_{21}$ aralkyl group, a $C_2$ to $C_4$ acyl group, a glycidyloxy group or a —$(CH_2)_{j2}$—O—CO—$R^{i1}$ group, wherein $R^{i1}$ represents a $C_1$ to $C_{16}$ aliphatic hydrocarbon group, a $C_3$ to $C_{16}$ alicyclic hydrocarbon group or a $C_6$ to $C_{18}$ aromatic hydrocarbon group, j2 represents an integer of 0 to 4. The aromatic hydrocarbon group and the aralkyl group of the substituent may further have a substituent such as a $C_1$ to $C_8$ alkyl group, a halogen atom or a hydroxy group.

Examples of the halogen atom include fluorine, chlorine, bromine and iodine atoms.

Examples of the alkoxyl group include methoxy, ethoxy, n-propoxy, isopropoxy, n-butoxy, sec-butoxy, tert-butoxy, n-pentyloxy, n-hexyloxy, heptyloxy, octyloxy, 2-ethylhexyloxy, nonyloxy, decyloxy, undecyloxy and dodecyloxy groups.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the aralkyl group include benzyl, phenethyl, phenylpropyl, naphthylmethyl and naphthylethyl groups.

Examples of the acyl group include acetyl, propionyl and butyryl groups.

Examples of the aliphatic hydrocarbon group of $R^{i1}$ include methyl, ethyl, propyl, butyl, pentyl, hexyl, heptyl and octyl groups. Examples of the alicyclic hydrocarbon group of $R^{i1}$ include monocyclic hydrocarbon groups, cycloalkyl group, such as cyclopentyl, cyclohexyl, methylcyclohexyl, dimethylcyclohexyl, cycloheptyl, cyclooctyl groups; and polycyclic hydrocarbon groups such as decahydronaphtyl, adamantyl, norbornyl (i.e., bicyclo[2.2.1]heptyl), and methyl norbornyl groups as well as groups below.

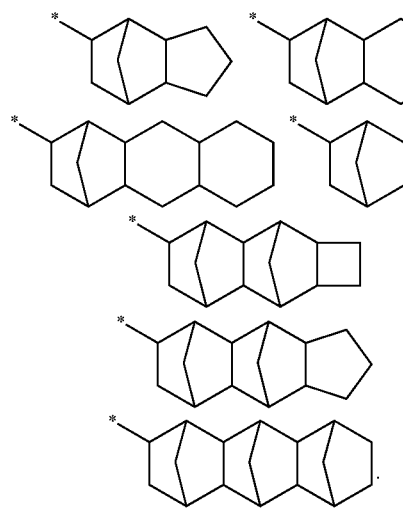

Examples of the aromatic hydrocarbon group include the same examples described above.

Examples of the alicyclic hydrocarbon group of $Y^{II1}$ in which one or more —CH$_2$— is replaced by the —O—, —SO$_2$— or —CO— include a cyclic ether group which is a group in which one or two —CH$_2$— contained in the alicyclic hydrocarbon group is replaced by the —O—;

a cyclic ketone group which is a group in which one or two —CH$_2$— contained in the alicyclic hydrocarbon group is replaced by the —CO—;

a sultone ring group which is a group in which an adjacent two —CH$_2$— contained in the alicyclic hydrocarbon group are replaced by the —O— and —SO$_2$—, respectively;

a lactone ring group which is a group in which an adjacent two —CH$_2$— contained in the alicyclic hydrocarbon group are replaced by the —O— and —CO—, respectively; and groups represented by the formula (Y12) to the formula (Y26).

 (Y1)

 (Y2)

 (Y3)

 (Y4)

 (Y5)

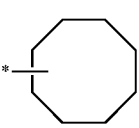 (Y6)

 (Y7)

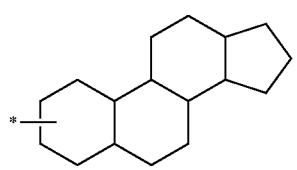 (Y8)

 (Y9)

 (Y10)

 (Y11)

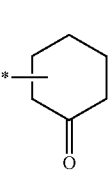 (Y12)

 (Y13)

(Y14) 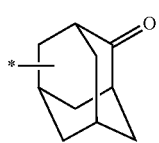

(Y15) 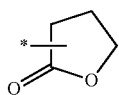

(Y16) 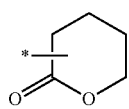

(Y17) 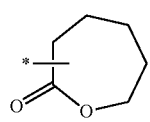

(Y18) 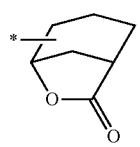

(Y19) 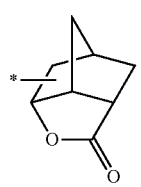

(Y20) 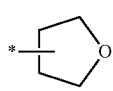

(Y21) 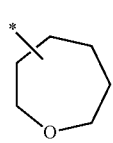

(Y22) 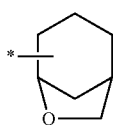

(Y23) 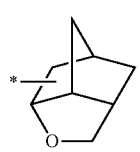

(Y24) 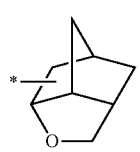

(Y25) 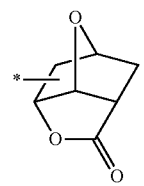

(Y26) 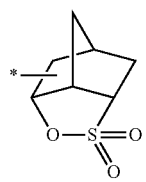

(Y27) 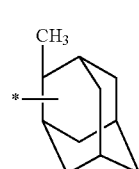

(Y28) 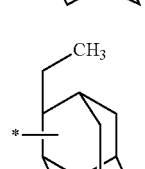

(Y29) 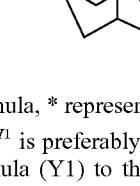

In the above formula, * represents a bond to $L^{II1}$.

Among these, $Y^{II1}$ is preferably any one of groups represented by the formula (Y1) to the formula (Y19) and the formula (Y27) to the formula (Y29), more preferably any one of groups represented by the formula (Y11), (Y14), (Y15), (Y19) and the formula (Y27) to the formula (Y29), and still more preferably group represented by the formula (Y11) and (Y14).

Examples of the alicyclic hydrocarbon group having a hydroxy group include groups below.

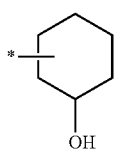 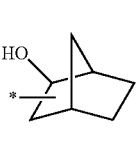 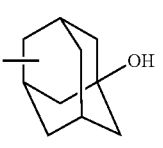

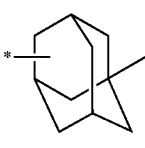

Examples of the alicyclic hydrocarbon group having a $C_6$ to $C_{18}$ aromatic hydrocarbon group include groups below.

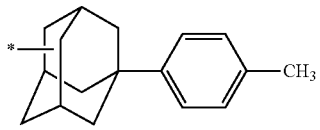

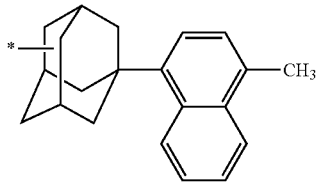

Examples of the alicyclic hydrocarbon group having $-(CH_2)_{j2}-O-CO-R^{i1}$ include groups below.

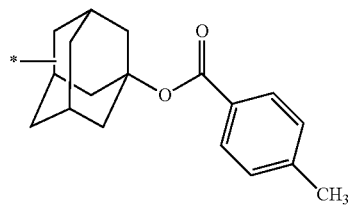

$Y^{II1}$ is preferably an adamantyl group which is optionally substituted, for example, an oxo group and a hydroxy group, and more preferably an adamantyl group, a hydroxyadamantyl group and an oxoadamantyl group.

The sulfonate anion is preferably an anions represented by the formula (b1-1-1) to the formula (b1-1-9) below. In the formula (b1-1-1) to the formula (b1-1-9), $R^{II1}$, $R^{II2}$ and $L^{II1}$ represents the same meaning as defined above. $R^{b2}$ and $R^{b3}$ independently represent a $C_1$ to $C_4$ alkyl group (preferably methyl group).

(b1-1-1)
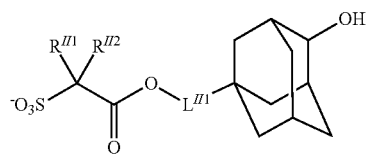

(b1-1-2)
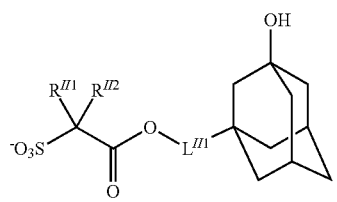

(b1-1-3)
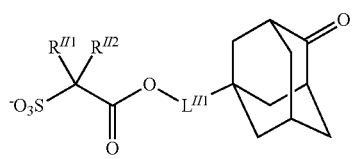

(b1-1-4)
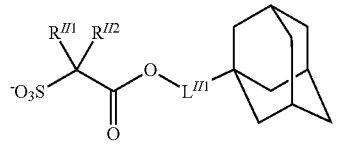

(b1-1-5)
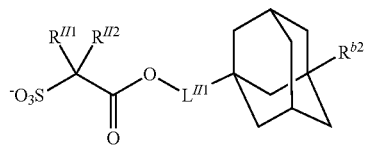

(b1-1-6)
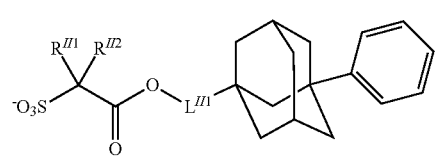

(b1-1-7)
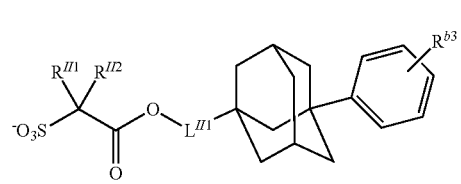

(b1-1-8)
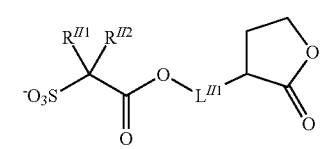

(b1-1-9)
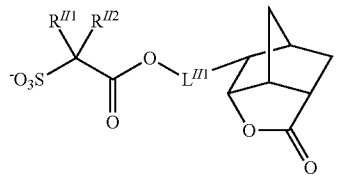

The sulfonate anion in which $Y^{II1}$ is a non-substituted alicyclic hydrocarbon group and $L^{II1}$ is a single bond or a $C_1$ to $C_6$ alkanediyl group is preferable. Examples of thereof include sulfonate anions below.

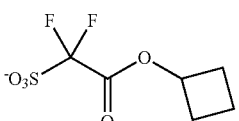 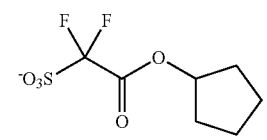

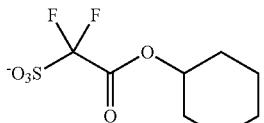 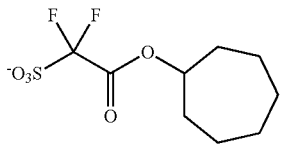

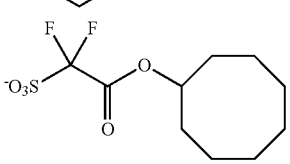

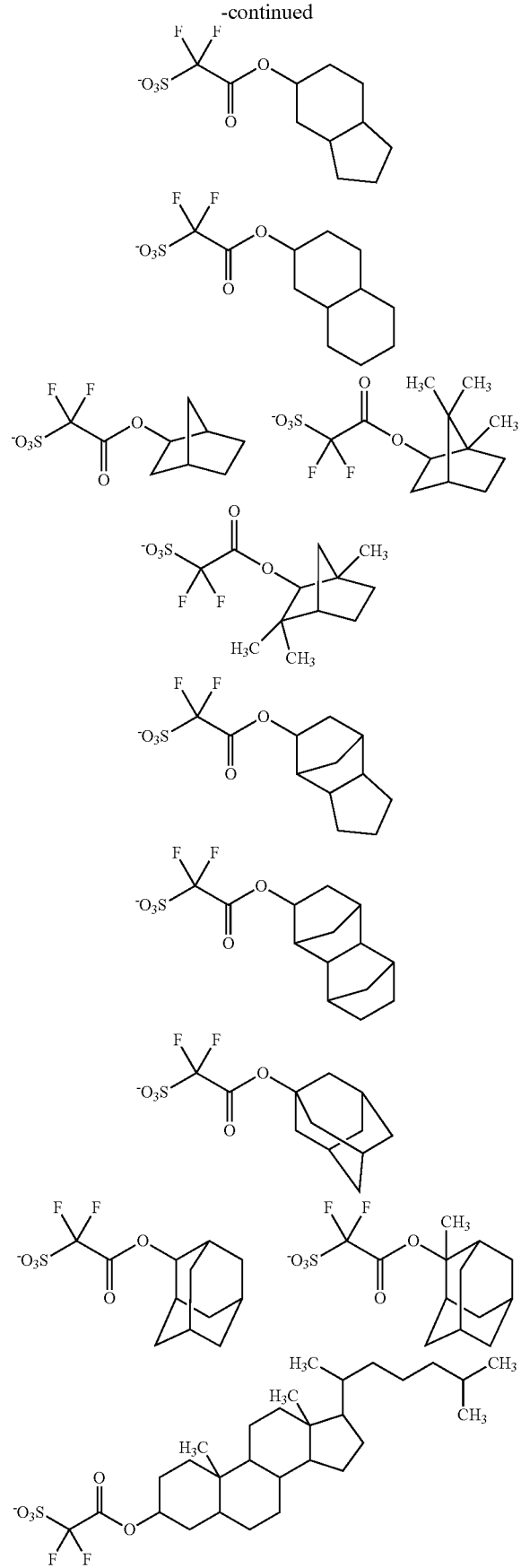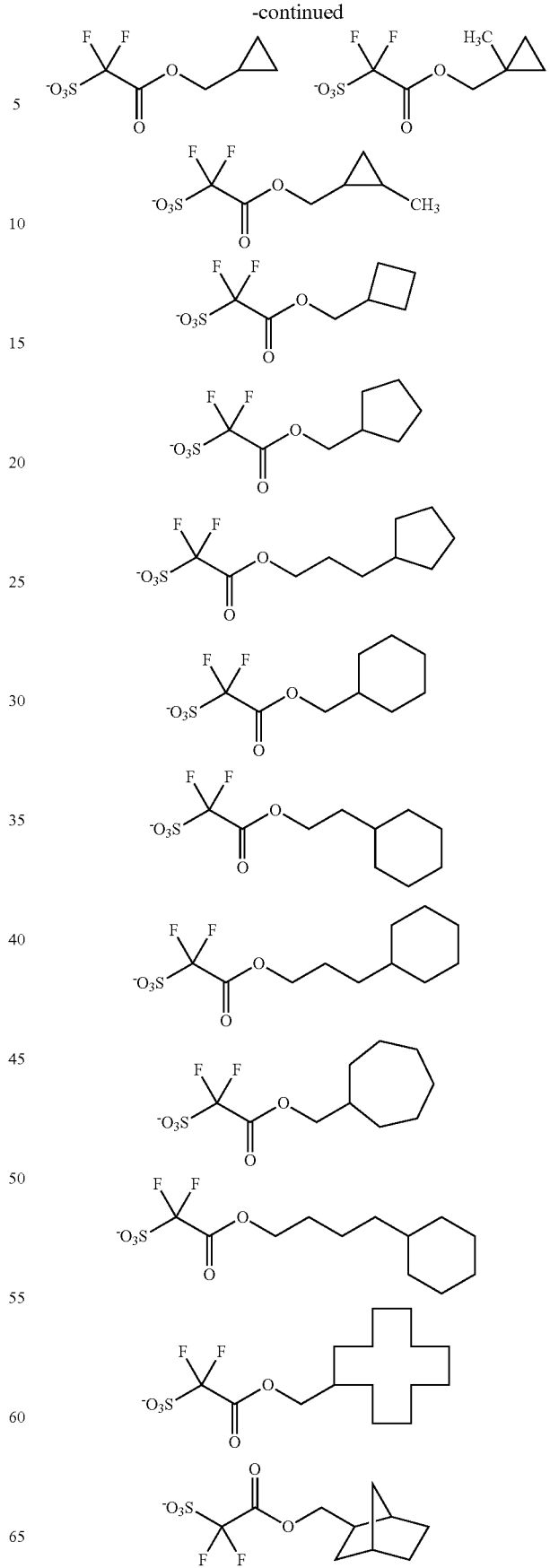

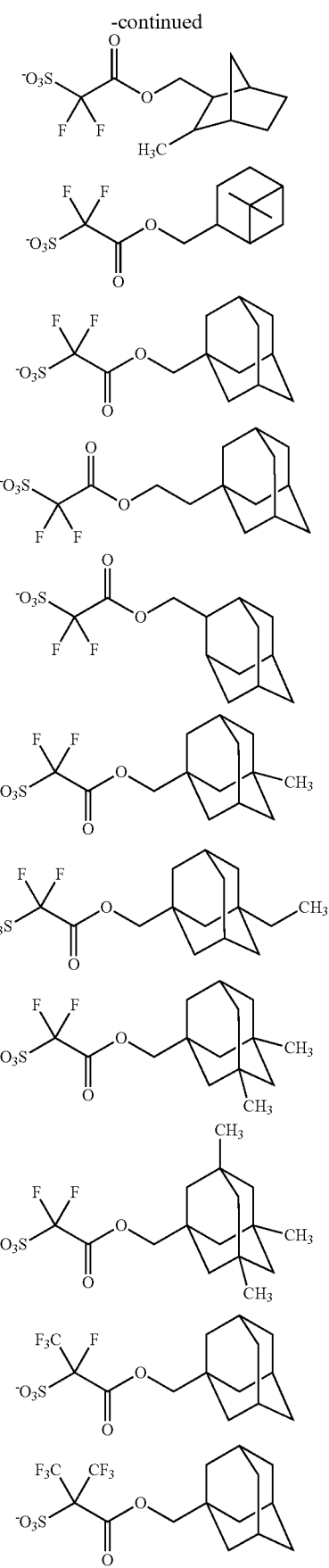
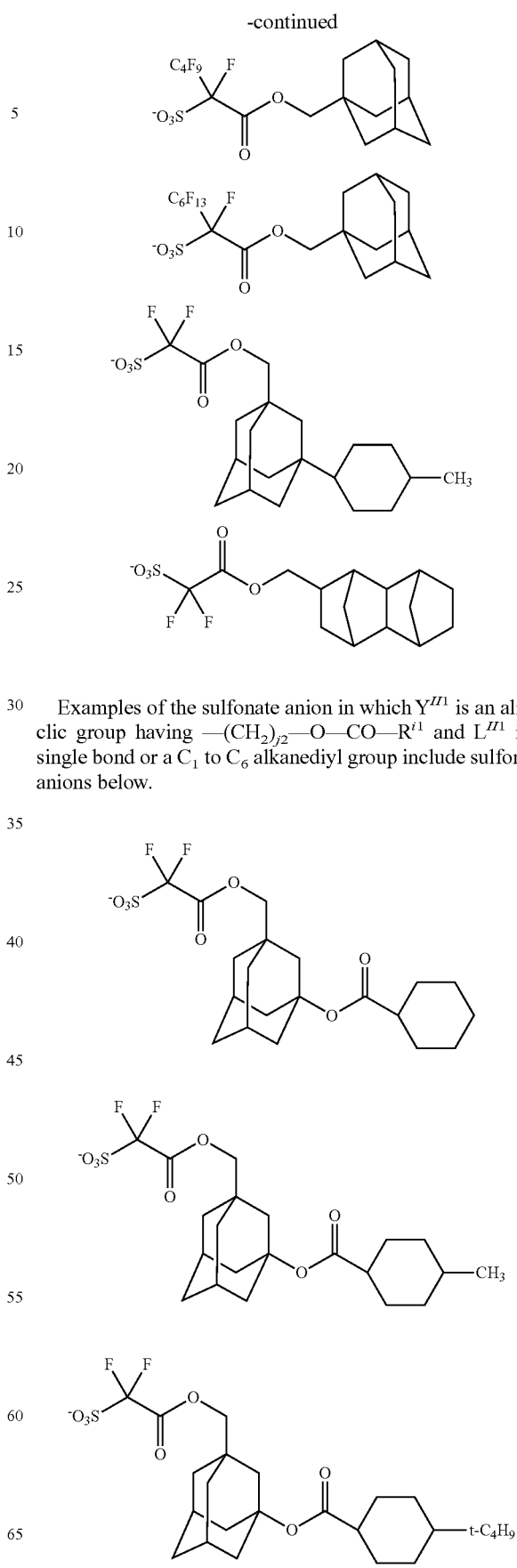
Examples of the sulfonate anion in which $Y^{II1}$ is an alicyclic group having $-(CH_2)_{j2}-O-CO-R^{i1}$ and $L^{II1}$ is a single bond or a $C_1$ to $C_6$ alkanediyl group include sulfonate anions below.

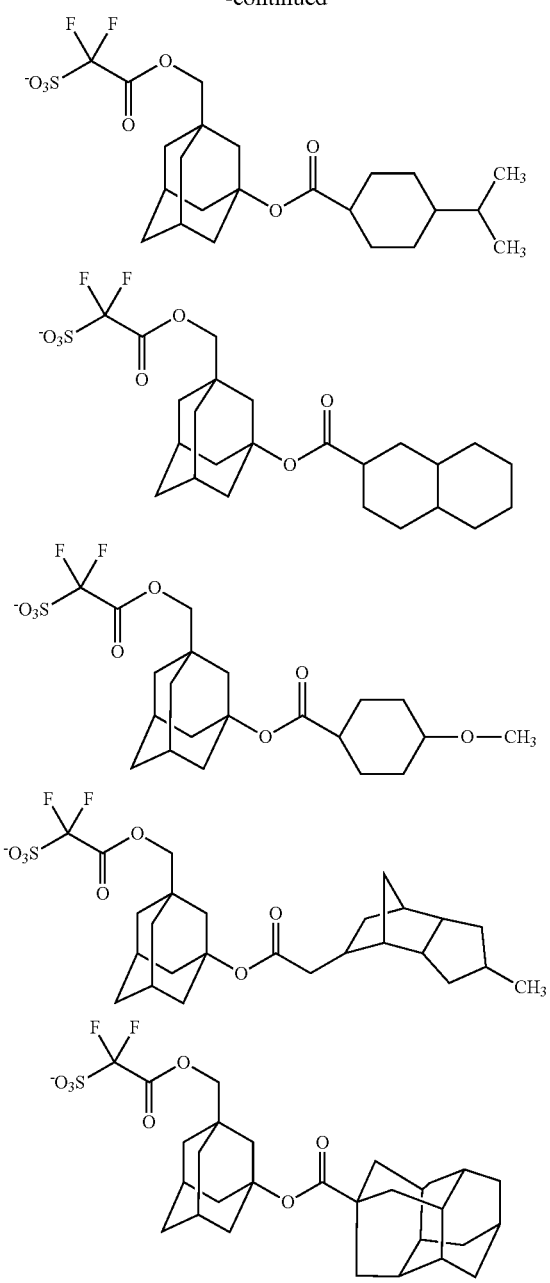
Examples of the sulfonate anion in which $Y^{II1}$ is an alicyclic group having a hydroxy group and $L^{II1}$ is a single bond or a $C_1$ to $C_6$ alkanediyl group include sulfonate anions below.
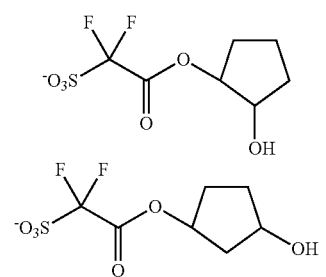
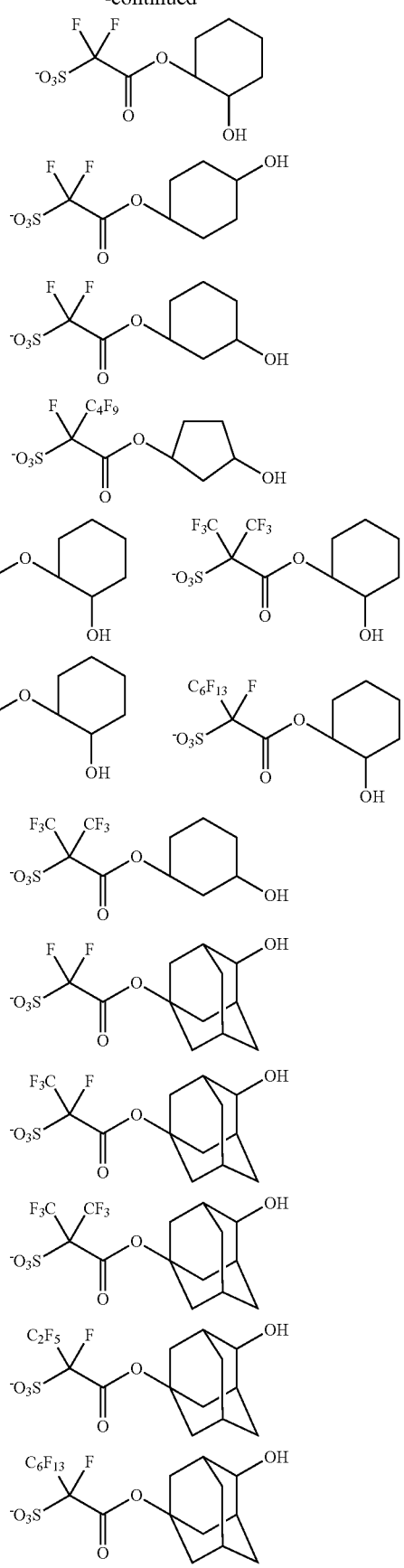

-continued
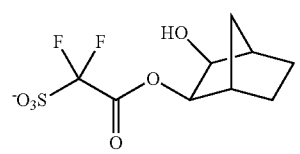
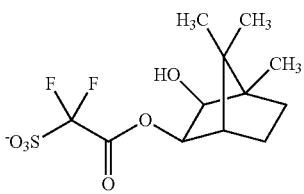
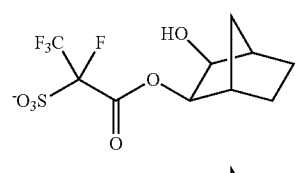
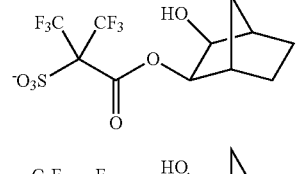
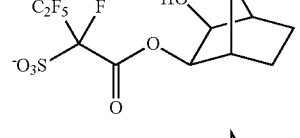
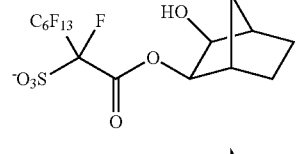
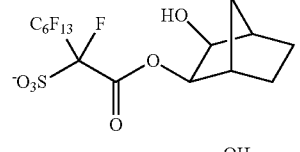
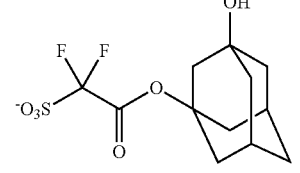
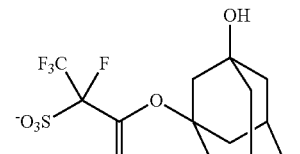
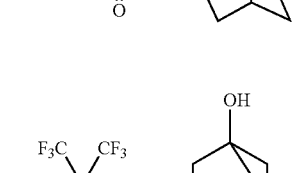
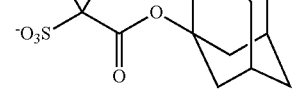
-continued
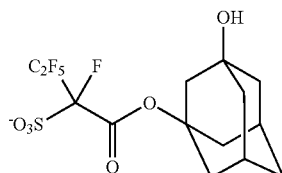
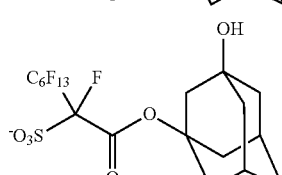
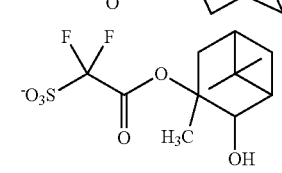
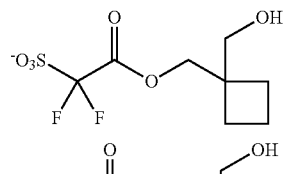
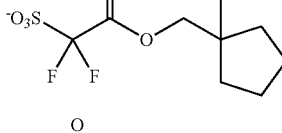
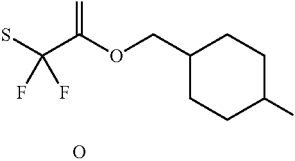
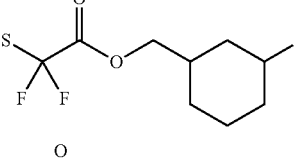
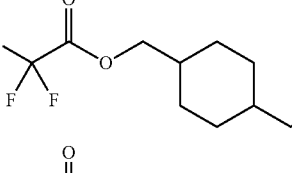
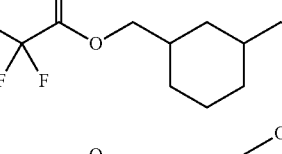
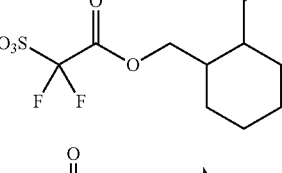
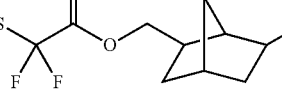

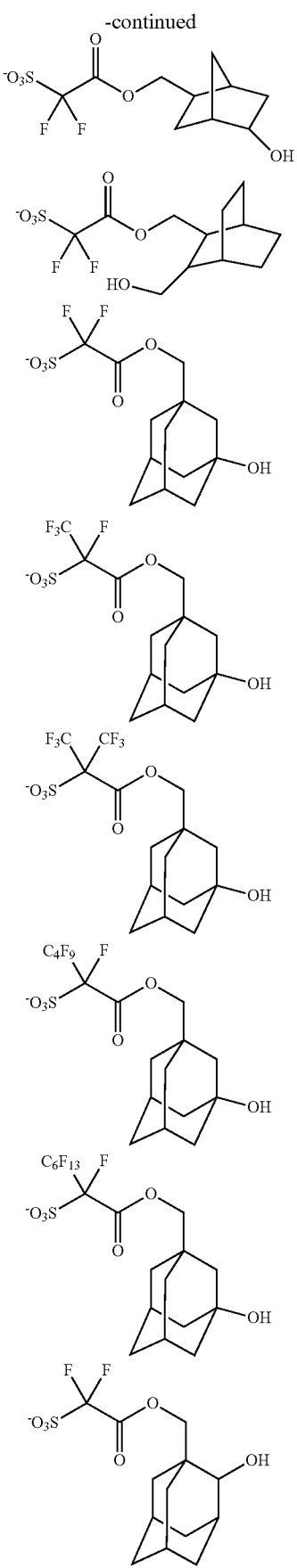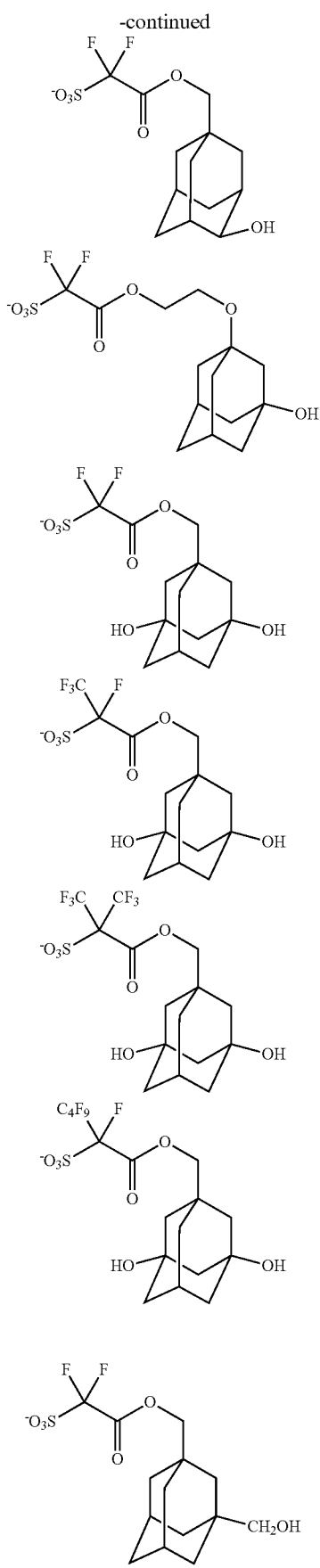

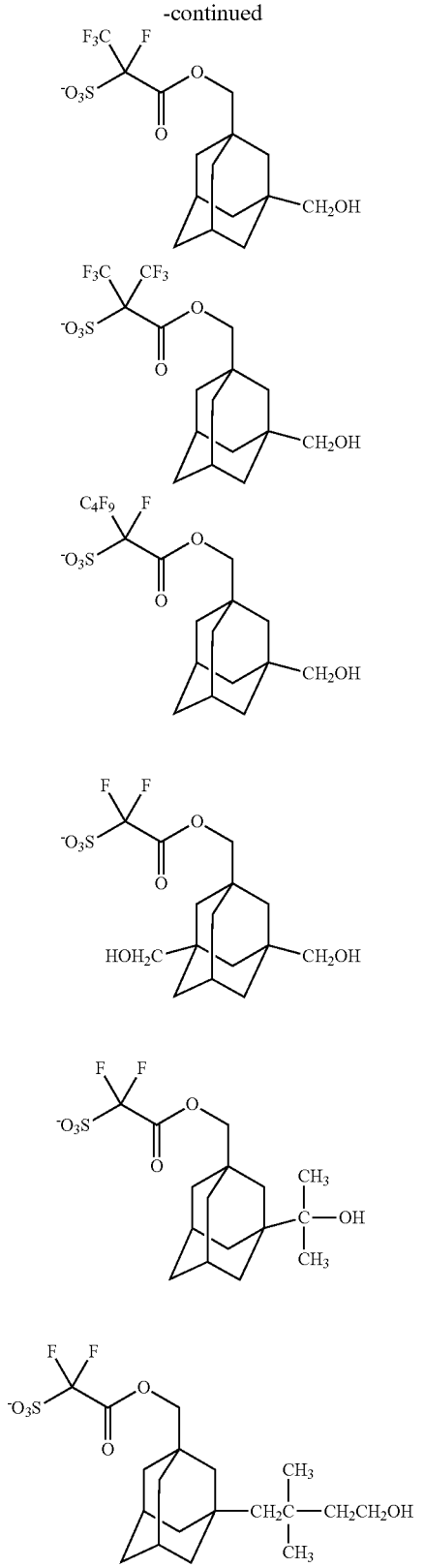
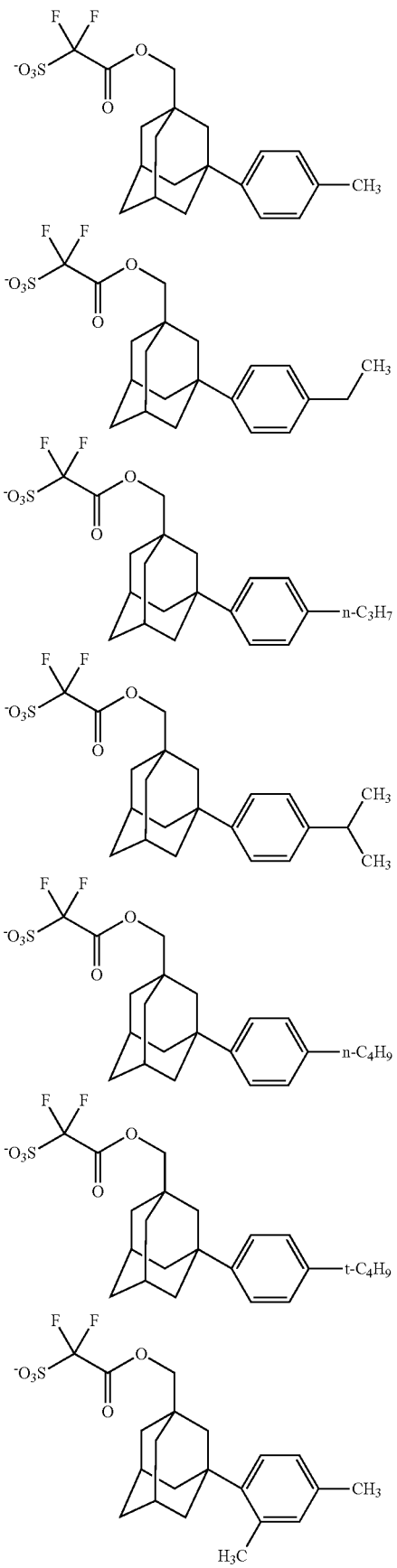
Examples of the sulfonate anion in which $Y^{II1}$ is an alicyclic group having an aromatic hydrocarbon group or an aralkyl group and $L^{II1}$ is a single bond or a $C_1$ to $C_6$ alkanediyl group include sulfonate anions below.

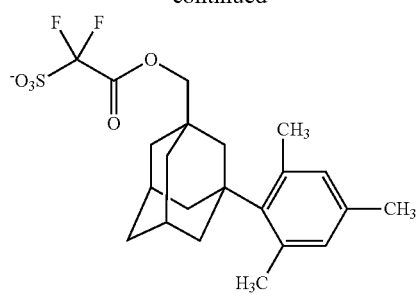
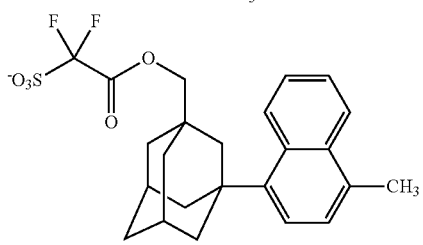
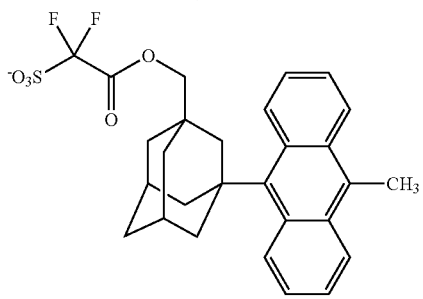
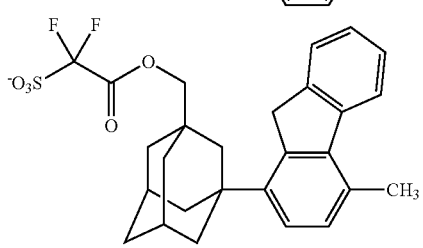
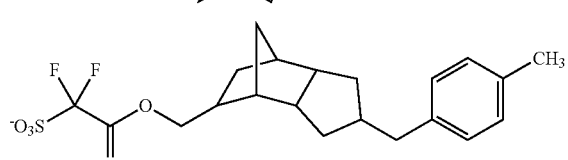
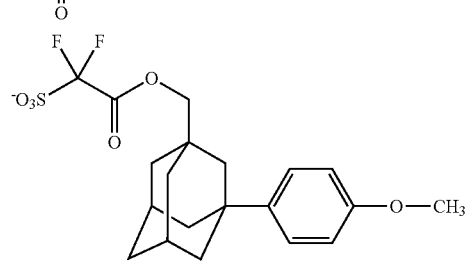
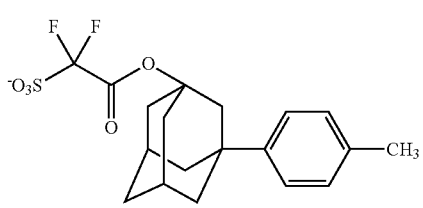
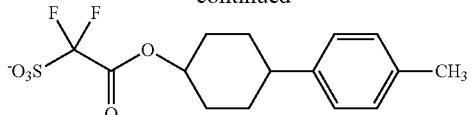
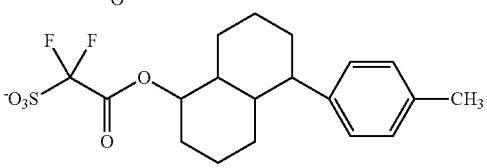
Examples of the sulfonate anion in which $Y^{II1}$ is a cyclic ether group and $L^{II1}$ is a single bond or a $C_1$ to $C_6$ alkanediyl group include sulfonate anions below.
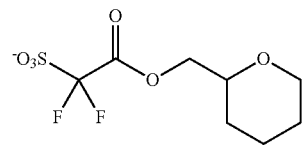
Examples of the sulfonate anion in which $Y^{II1}$ is a lactone ring group and $L^{II1}$ is a single bond or a $C_1$ to $C_6$ alkanediyl group include sulfonate anions below.
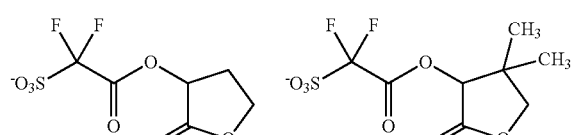
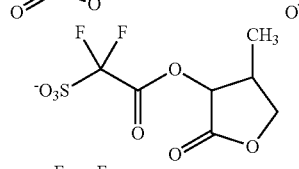
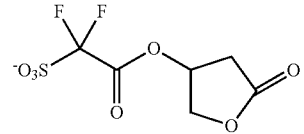
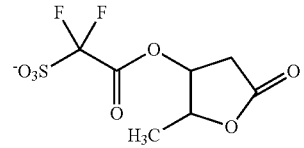
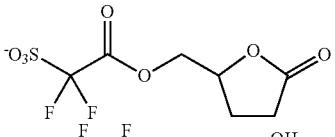
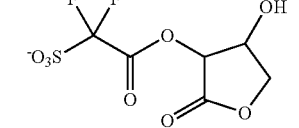
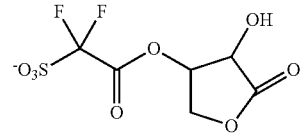

53
-continued
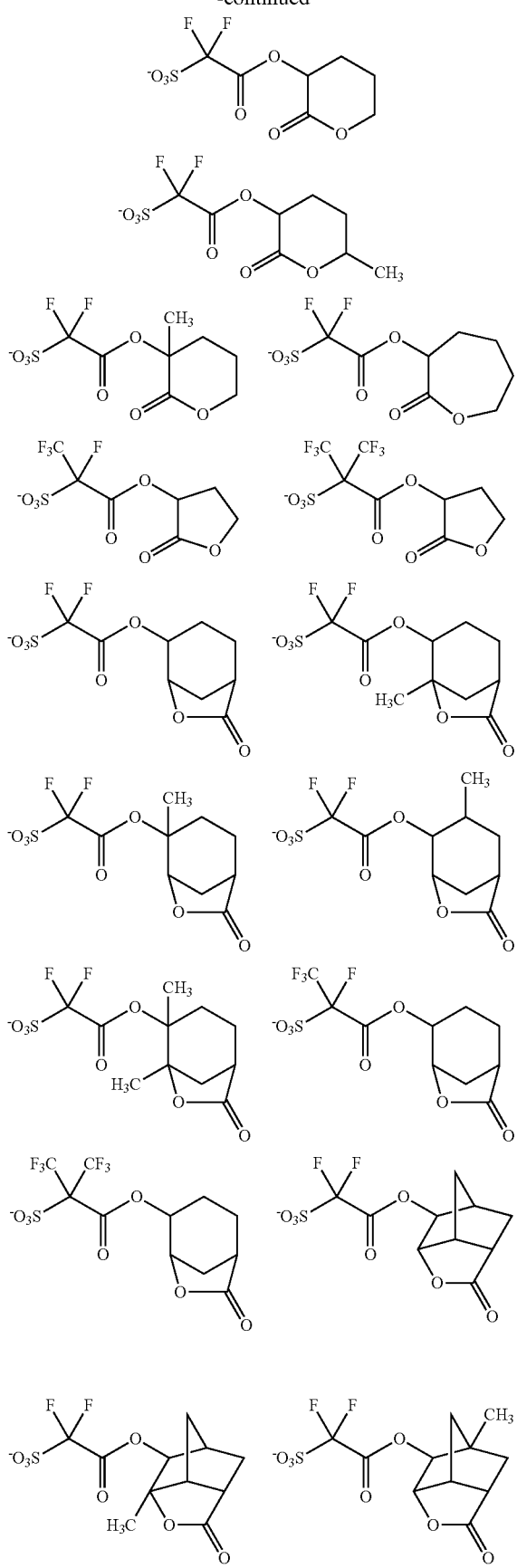
54
-continued
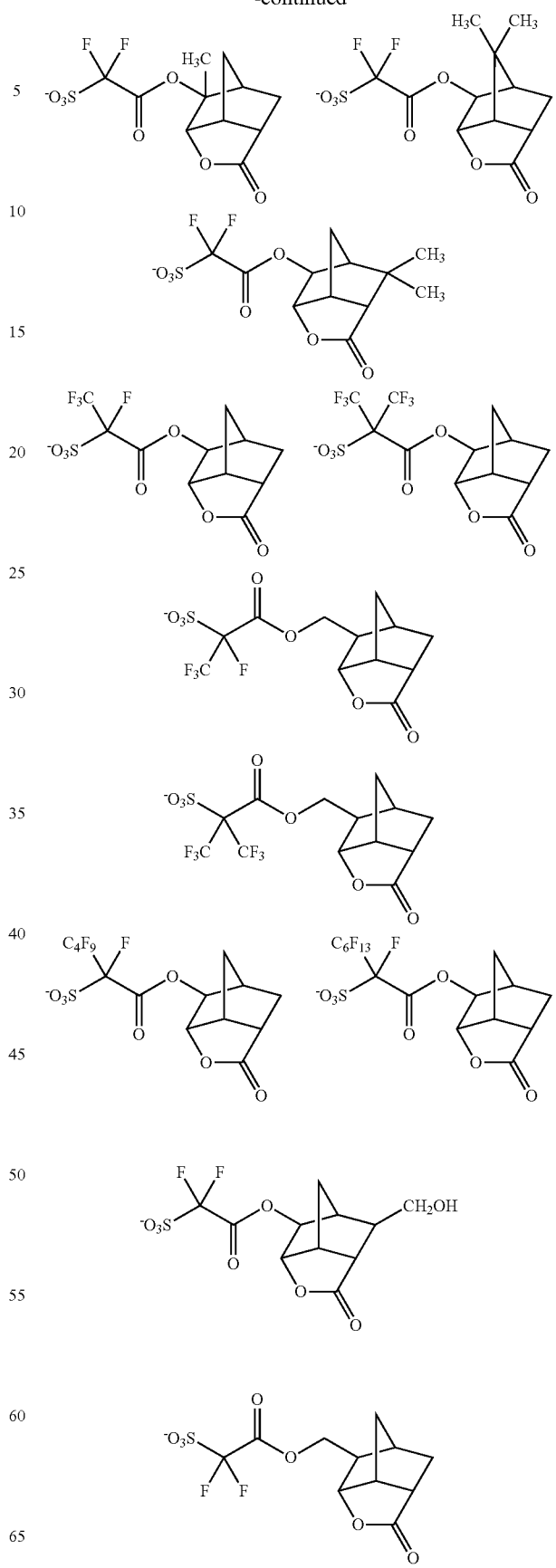

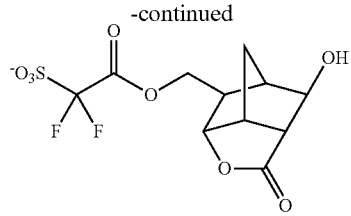

Examples of the sulfonate anion in which $Y^{II1}$ is a cyclic ketone group and $L^{II1}$ is a single bond or a $C_1$ to $C_6$ alkanediyl group include sulfonate anions below.

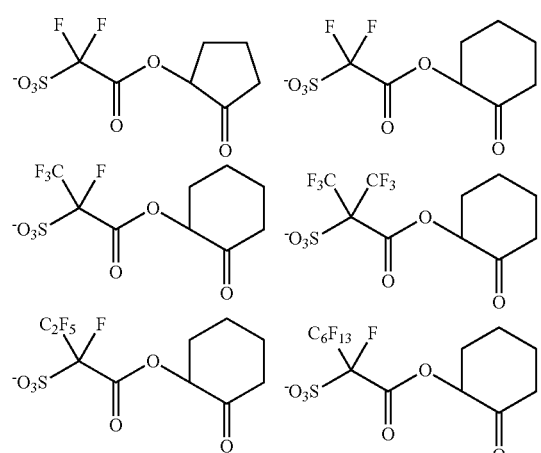

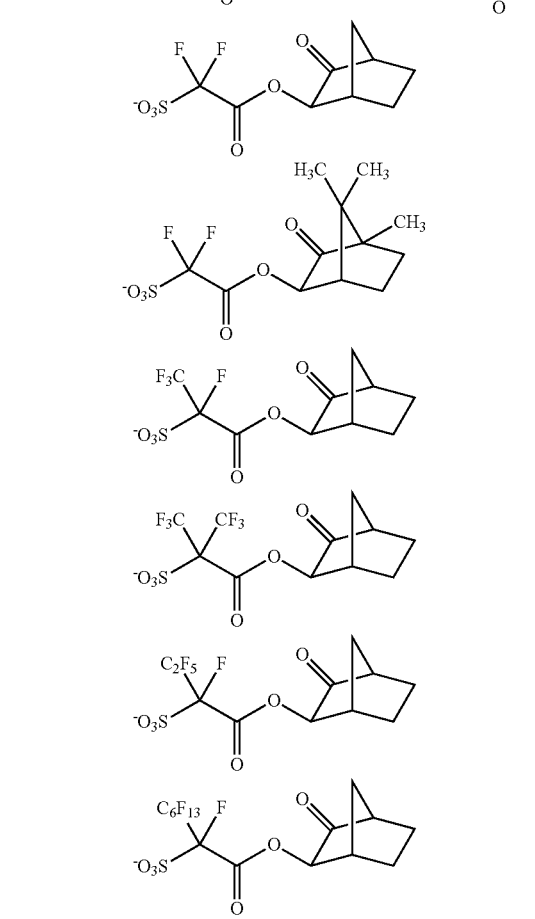

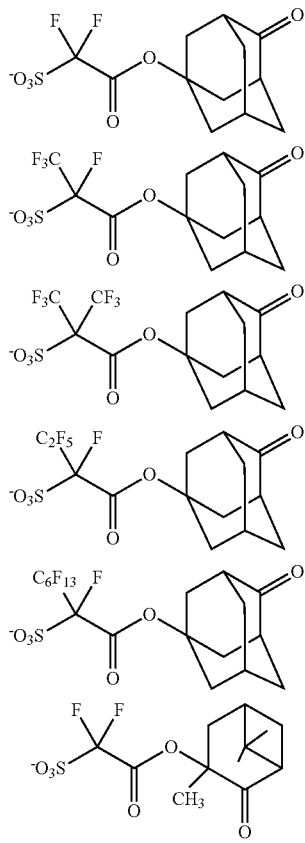

Examples of the sulfonate anion in which $Y^{II1}$ is a sultone ring group and $L^{II1}$ is a single bond or a $C_1$ to $C_6$ alkanediyl group include sulfonate anions below.

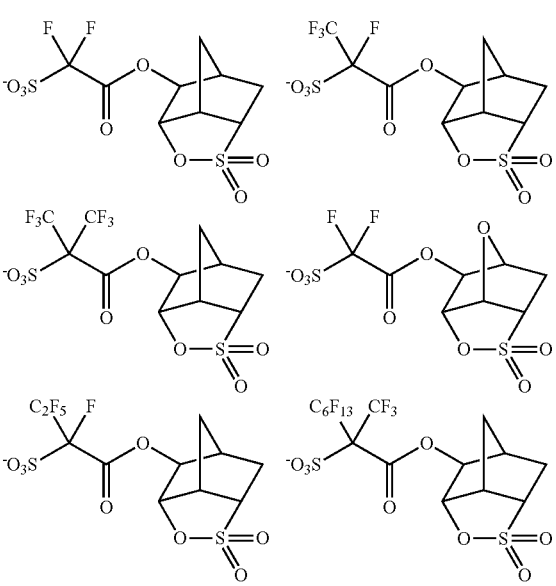

Examples of the sulfonate anion in which $Y^{II1}$ is a non-substituted alicyclic hydrocarbon group and $L^{II1}$ is —$(CH_2)_t$—CO—O—* or —$(CH_2)_t$—CO—O—$CH_2$—$(CH_2)_u$—* include sulfonate anions below.

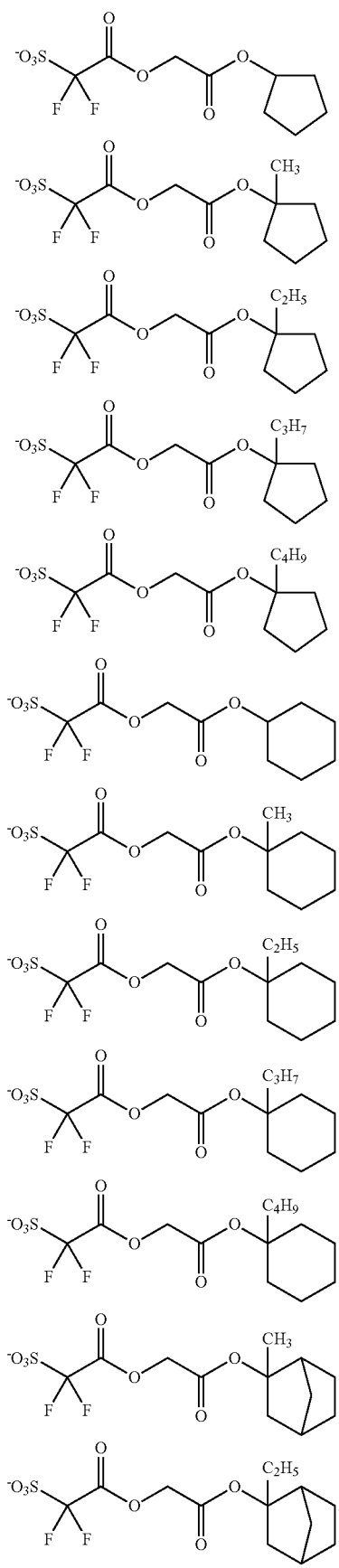
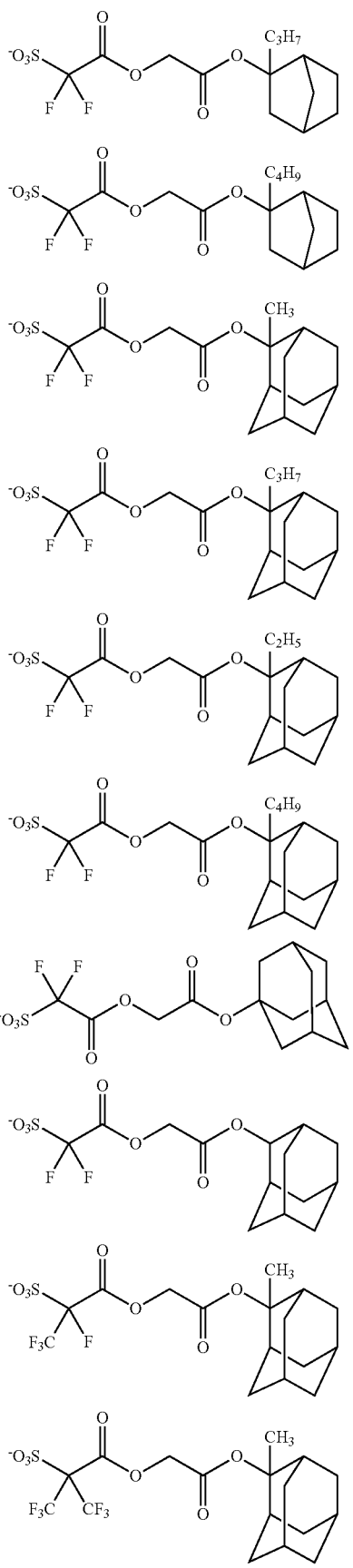

59
-continued
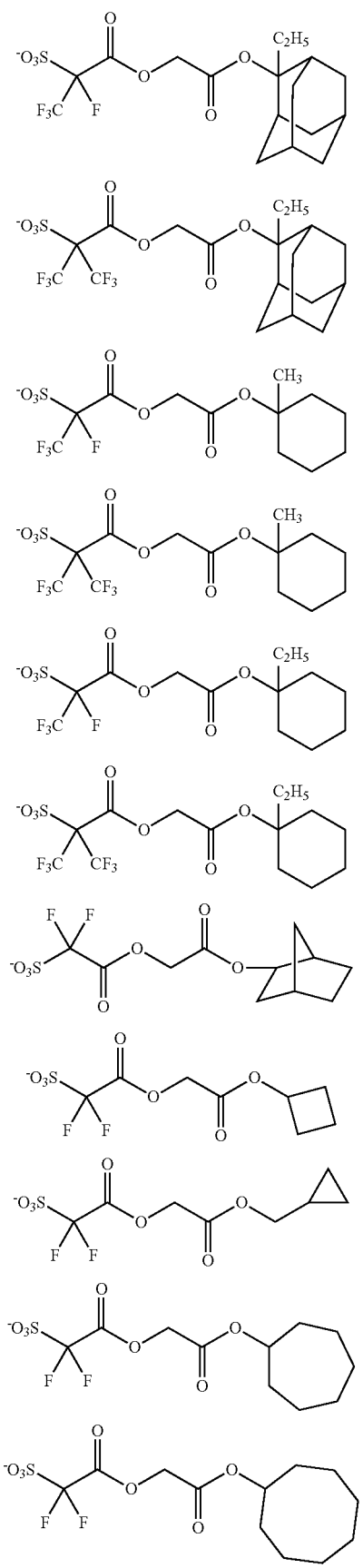
60
-continued
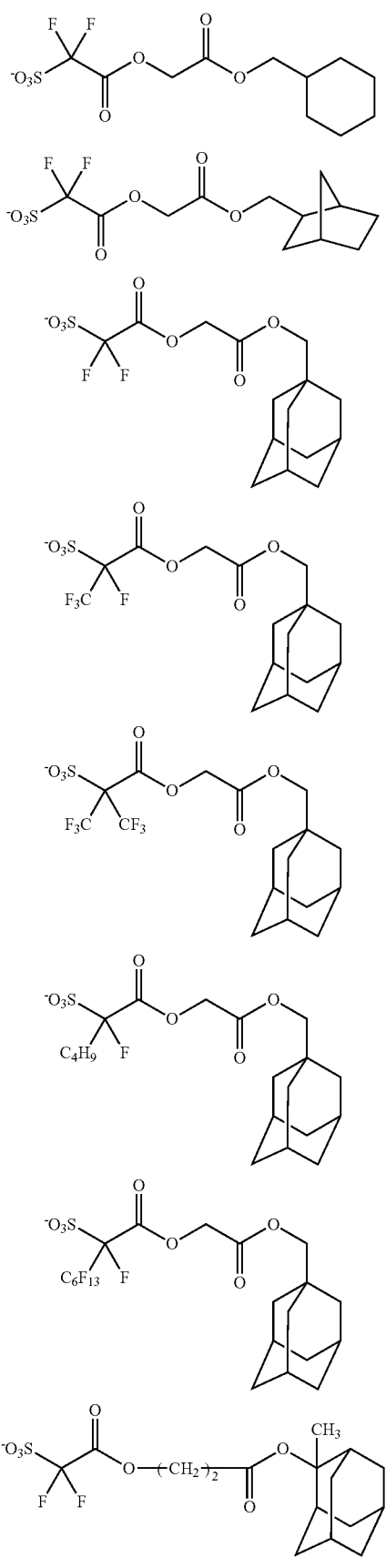

-continued
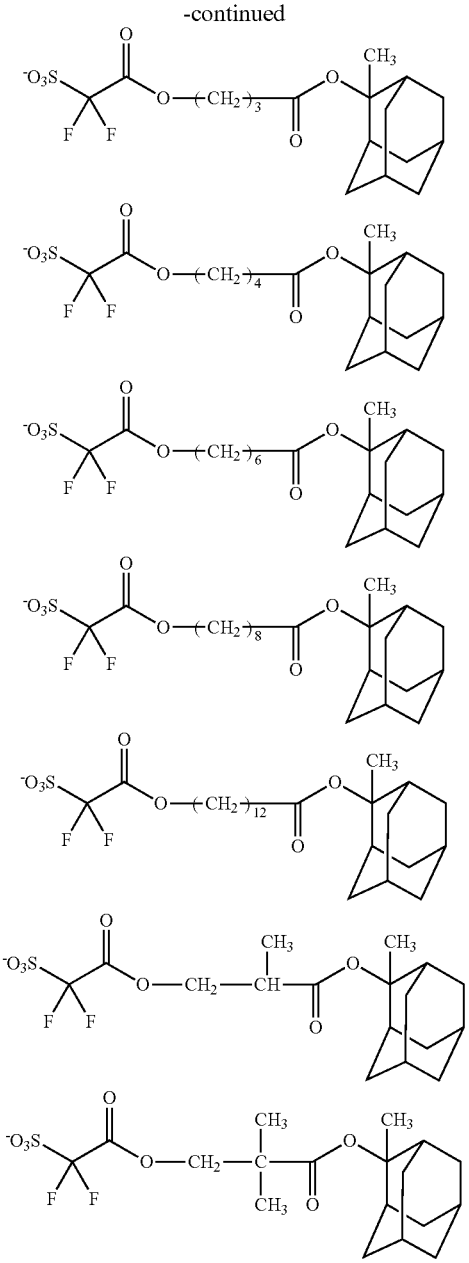
Examples of the sulfonate anion in which $Y^{II1}$ is an alicyclic group having a hydroxy group and $L^{II1}$ is —$(CH_2)_t$—CO—O—* or —$(CH_2)_t$—CO—O—$CH_2$—$(CH_2)_u$—* include a sulfonate anions below.
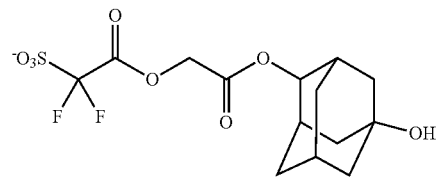
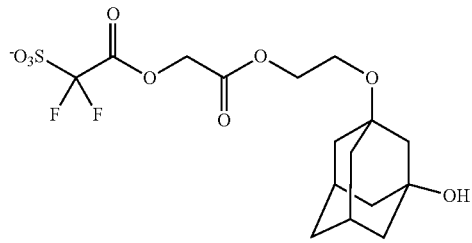
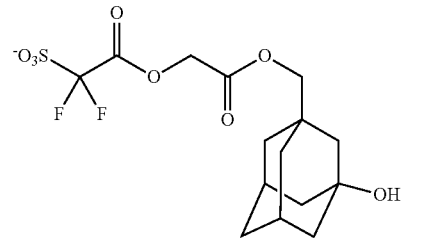
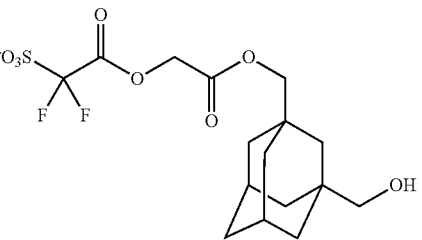
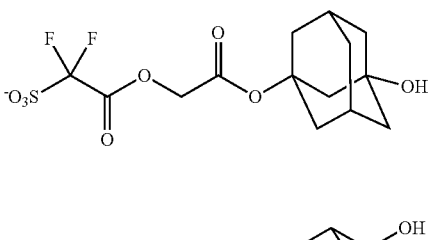
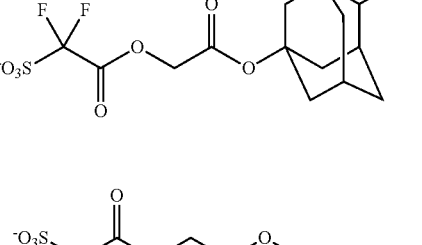
Examples of the sulfonate anion in which $Y^{II1}$ is an alicyclic group having —$(CH_2)_{j2}$—O—CO—$R^{i1}$ and $L^{II1}$ is —$(CH_2)_t$—CO—O—* or $(CH_2)_t$—CO—$CH_2$—$(CH_2)_u$—* include sulfonate anions below.
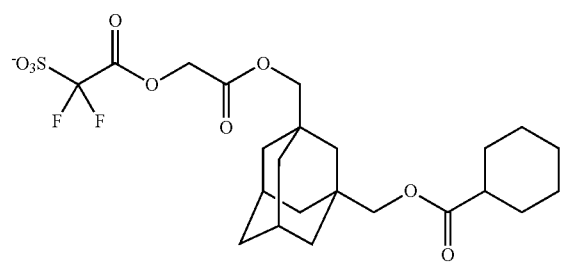
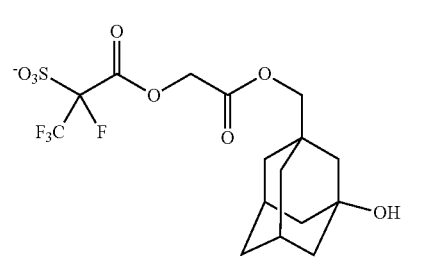

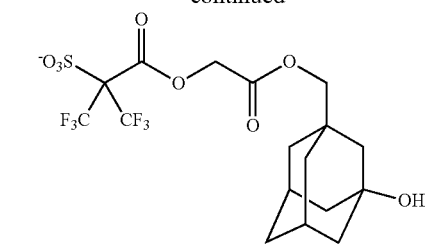

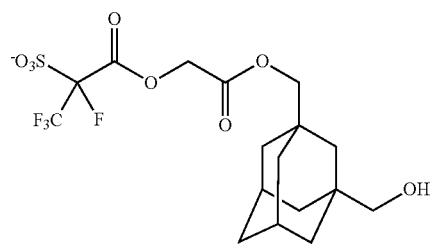

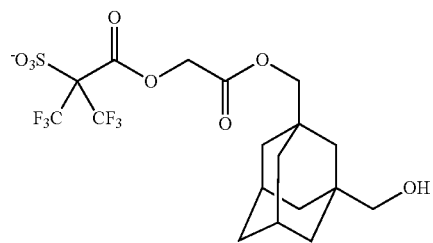

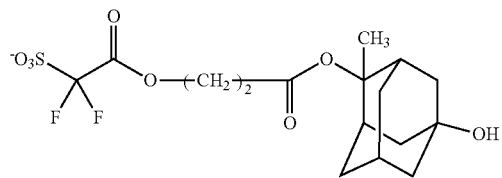

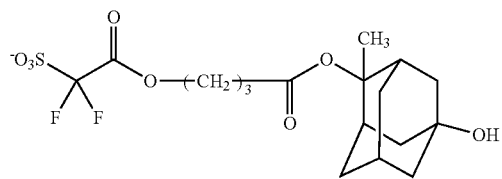

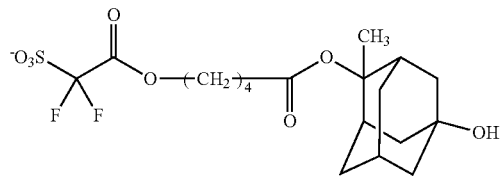

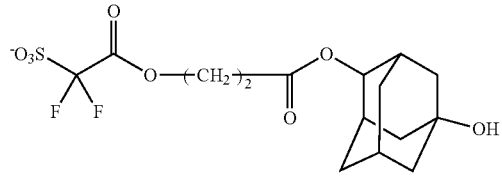

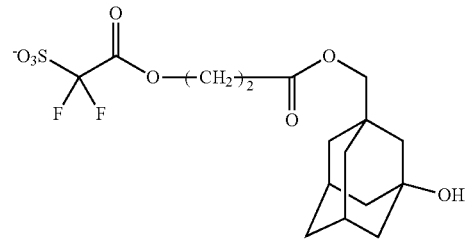

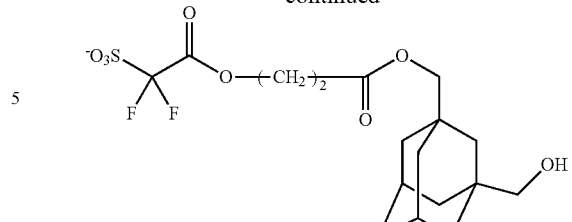

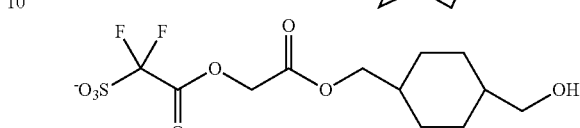

Examples of the sulfonate anion in which $Y^{II1}$ is an alicyclic group having a aromatic hydrocarbon group and $L^{II1}$ is —$(CH_2)_t$—CO—O—* or —$(CH_2)_t$—CO—O—$CH_2$—$(CH_2)_u$—* include a sulfonate anions below.

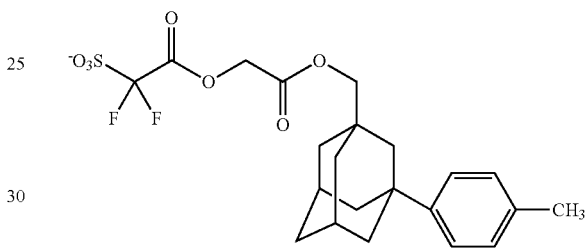

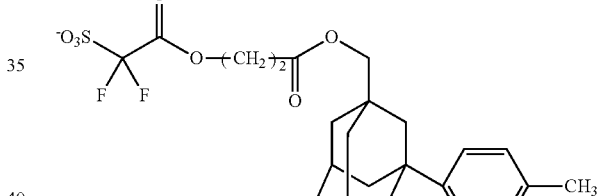

Examples of the sulfonate anion in which $Y^{II1}$ is a cyclic ether group and $L^{II1}$ is —$(CH_2)_t$—CO—O—* or —$(CH_2)_t$—CO—O—$CH_2$—$(CH_2)_u$—* include a sulfonate anions below.

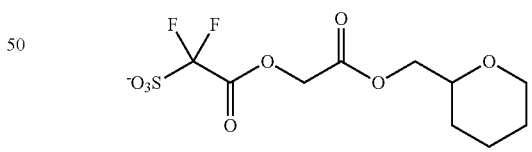

Examples of the sulfonate anion in which $Y^{II1}$ is a lactone ring group and $L^{II1}$ is —$(CH_2)_t$—CO—O—* or —$(CH_2)_t$—CO—O—$CH_2$—$(CH_2)_u$—* include a sulfonate anions below.

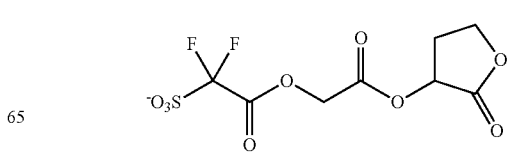

-continued
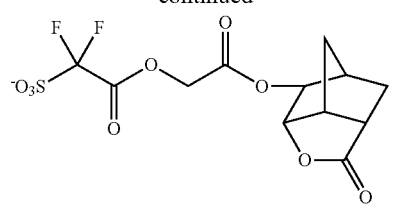
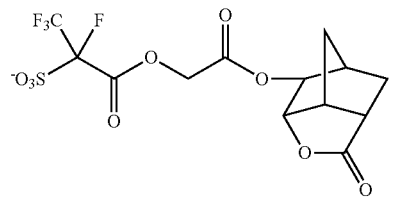
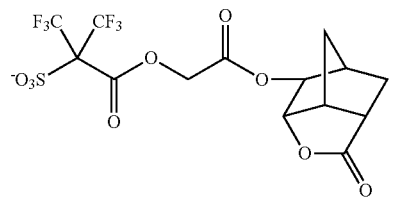
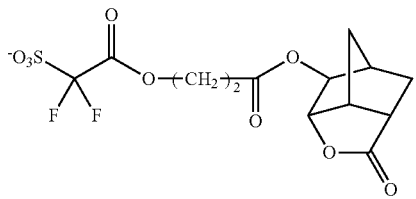
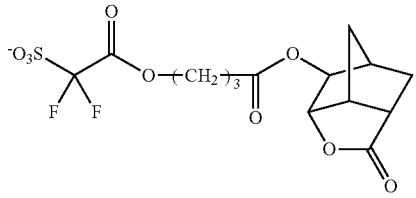
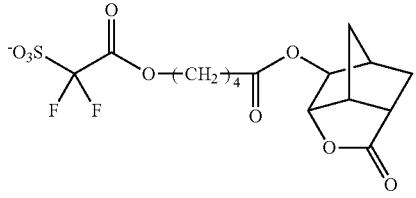
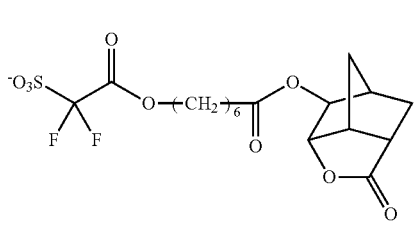
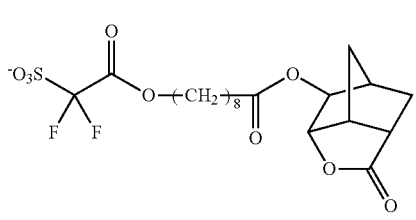
-continued
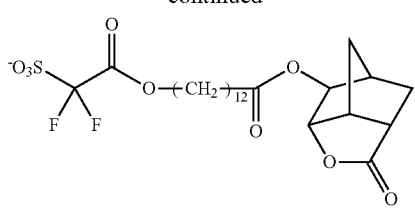
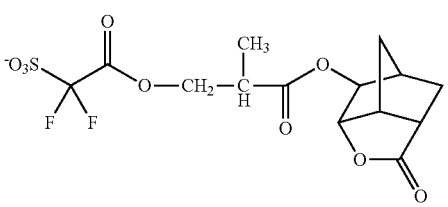
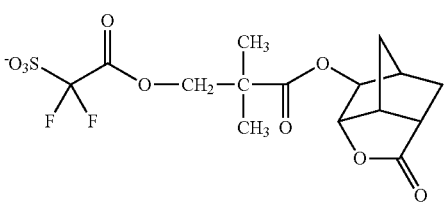
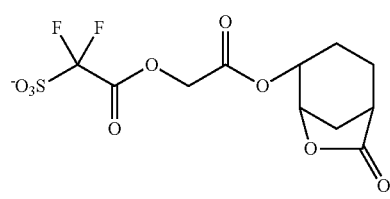
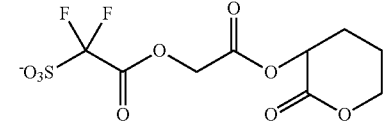
Examples of the sulfonate anion in which $Y^{II1}$ is a cyclic ketone group and $L^{II1}$ is —(CH$_2$)$_t$—CO—O—* or —(CH$_2$)$_t$—CO—O—CH$_2$—(CH$_2$)$_u$— include a sulfonate anions below.
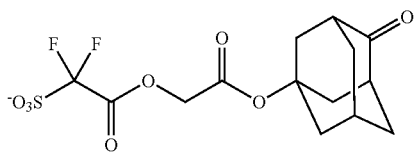
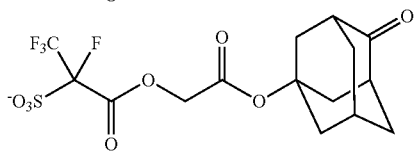
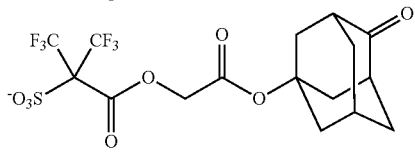
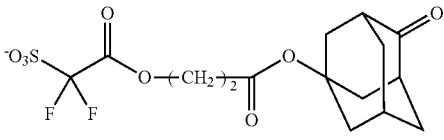

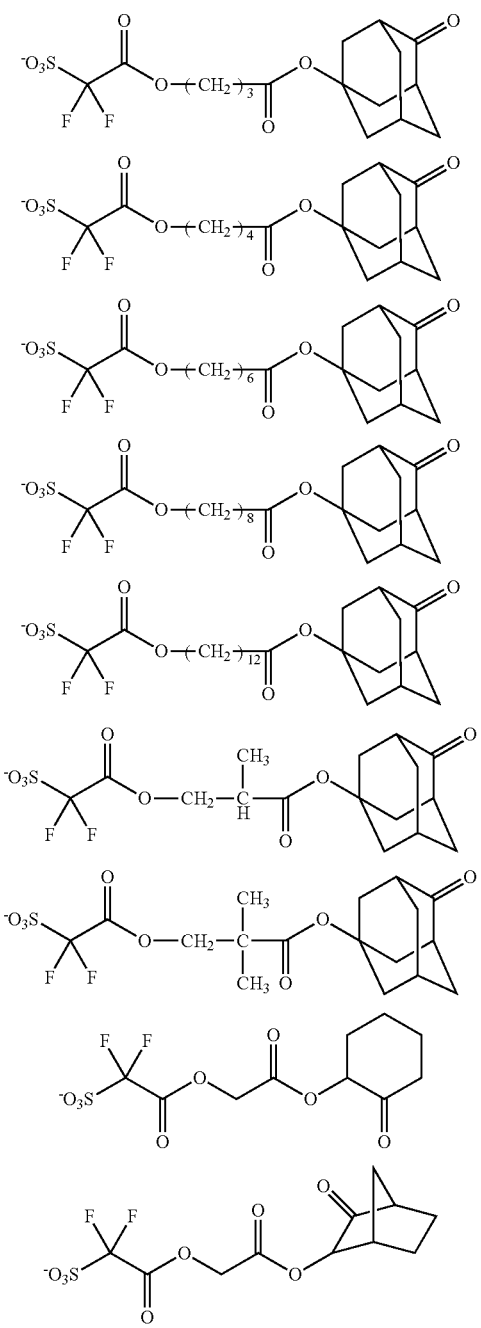
Examples of the sulfonate anion in which $Y^{II1}$ is a sultone ring group and $L^{II1}$ is $-(CH_2)_t-CO-O-*$ or $-(CH_2)_t-CO-O-CH_2-(CH_2)_u-*$ include a sulfonate anions below.
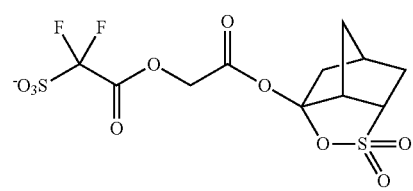
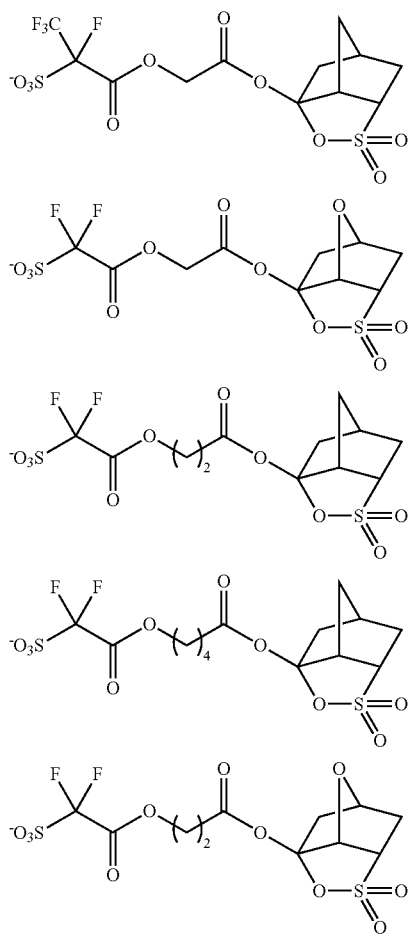
Examples of the sulfonate anion in which $Y^{II1}$ is a non-substituted alicyclic hydrocarbon group and $L^{II1}$ is $-(CH_2)_t-CO-O-*$ or $-(CH_2)_t-CO-O-CH_2-(CH_2)_u-*$ include a sulfonate anions below.
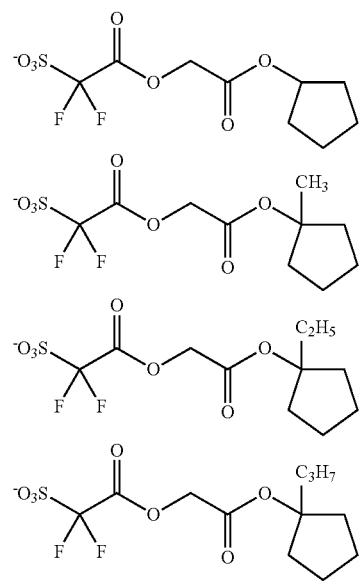

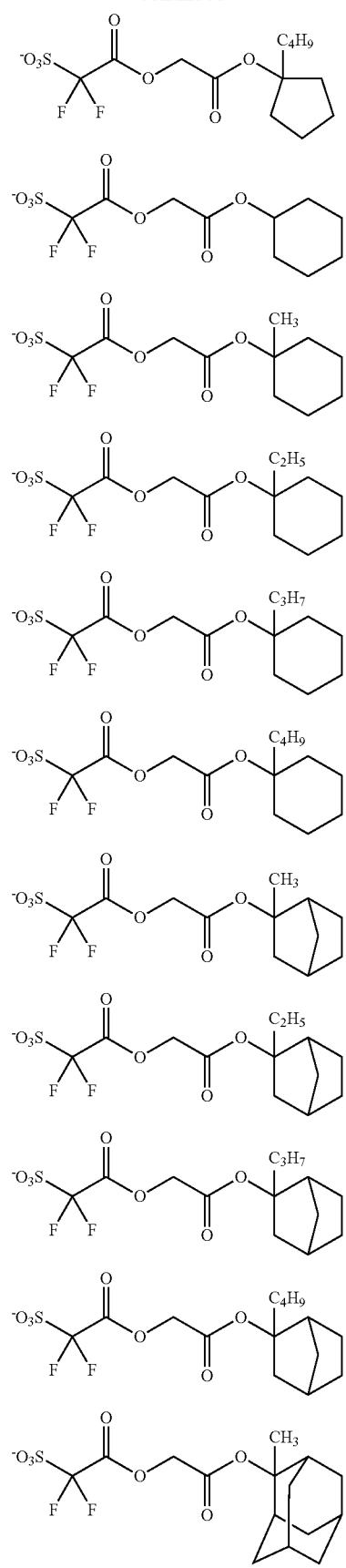
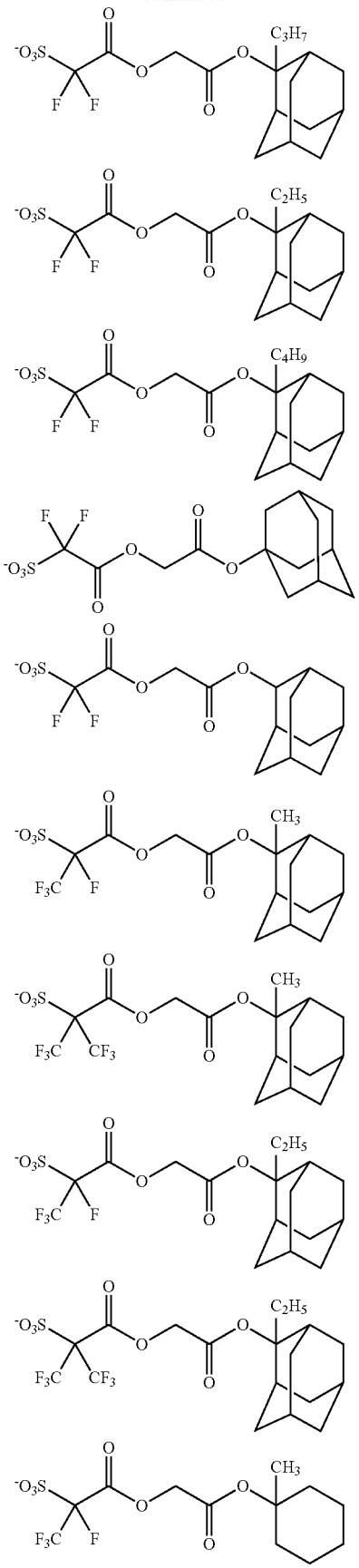

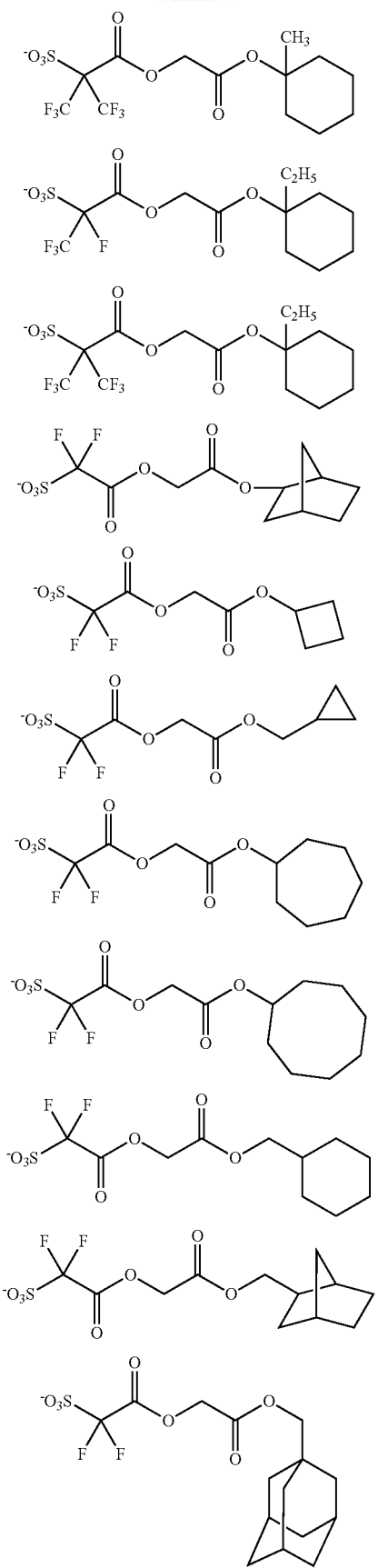
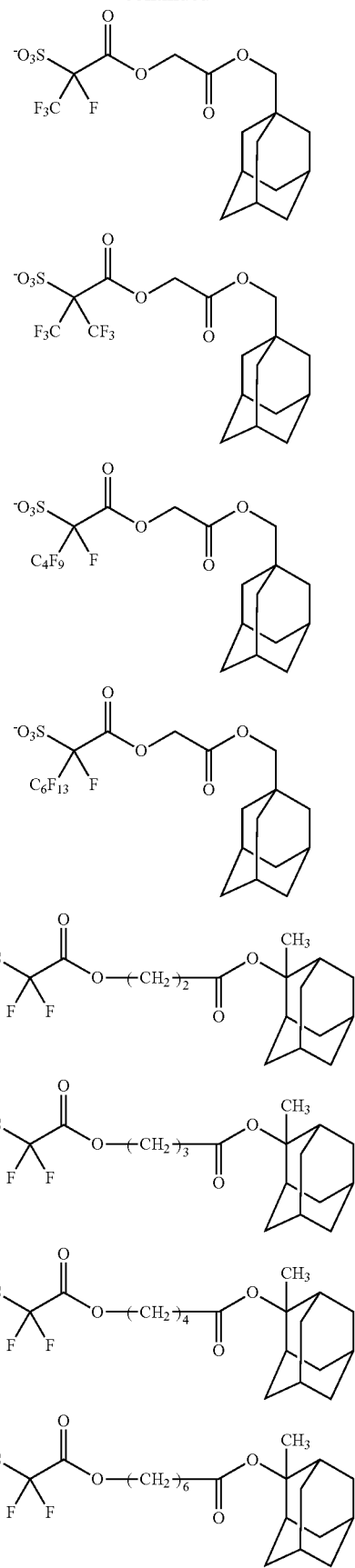

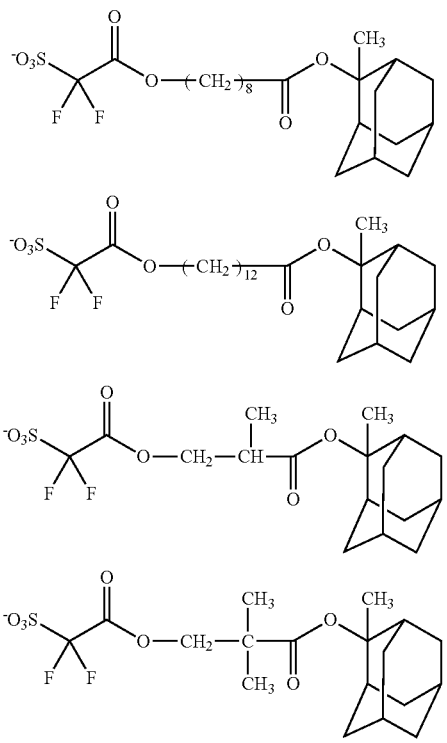

Among these, sulfonate anions as described below are preferable.

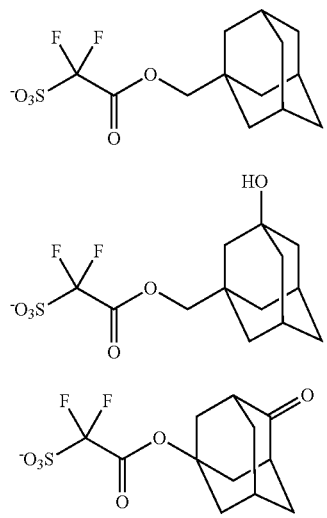

(II-a-1)
(II-a-2)
(II-a-3)
(II-a-4)

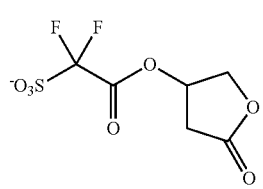

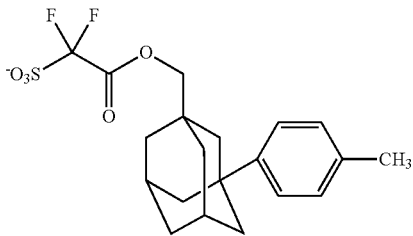

(II-a-5)

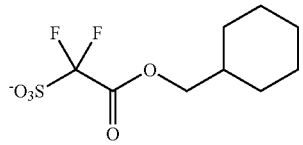

(II-a-6)

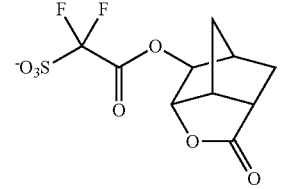

(II-a-7)

Examples of the alkyl group of $R^{II3}$ to $R^{II7}$ include methyl, ethyl, propyl and butyl groups.

Examples of the alkoxyl group include methoxy, ethoxy, propoxy, isopropoxy and butoxy groups.

Examples of the acyloxy group include acetyloxy and benzyloxy groups.

Examples of the alkyl group of $R^{II8}$ include methyl, ethyl, propyl, butyl, pentyl and hexyl groups.

Examples of groups in which one or more —CH$_2$— contained in sulfur-containing ring of cation is replaced by —O— or —CO— include below.

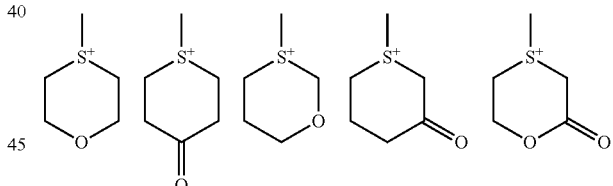

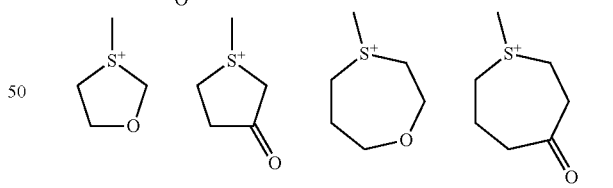

Examples of the organic cations include cations below.

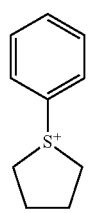

(II-c-1)

-continued
(II-c-2)
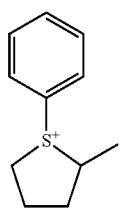
(II-c-3)
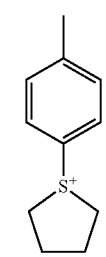
(II-c-4)
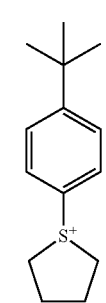
(II-c-5)
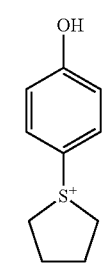
(II-c-6)
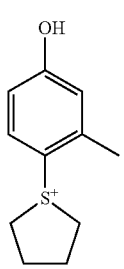
(II-c-7)
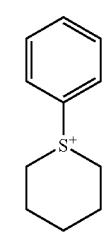
-continued
(II-c-8)
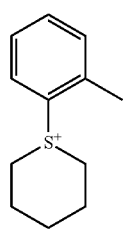
(II-c-9)
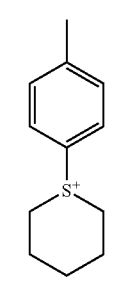
(II-c-10)
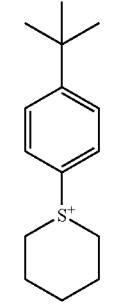
(II-c-11)
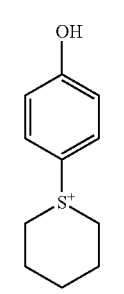
(II-c-12)
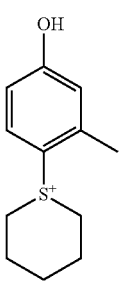
(II-c-13)
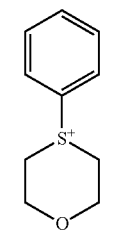

(II-c-14)
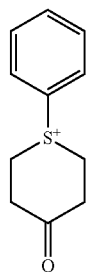
(II-c-15)
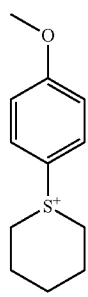
(II-c-16)
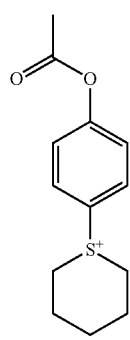
(II-c-17)
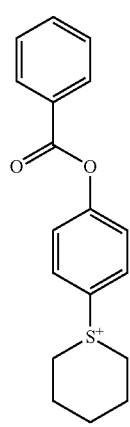
(II-c-18)
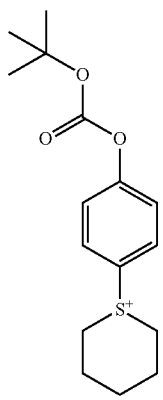
(II-c-19)
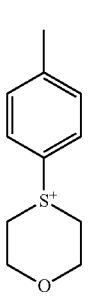
(II-c-20)
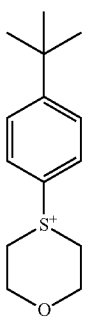
(II-c-21)
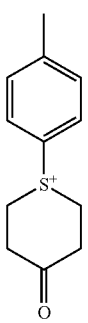

(II-c-22)

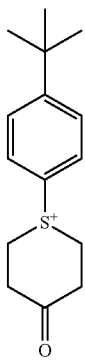

Examples of the acid generator (II) include salts in combination a sulfonate anion and an organic cation as described in the tables.

TABLE 1

| Acid generator (II) | Sulfonate anion | Organic cation |
|---|---|---|
| (II-1) | (II-a-2) | (II-c-7) |
| (II-2) | (II-a-2) | (II-c-13) |
| (II-3) | (II-a-2) | (II-c-20) |
| (II-4) | (II-a-3) | (II-c-13) |
| (II-5) | (II-a-2) | (II-c-10) |
| (II-6) | (II-a-2) | (II-c-4) |
| (II-7) | (II-a-1) | (II-c-1) |
| (II-8) | (II-a-2) | (II-c-1) |
| (II-9) | (II-a-3) | (II-c-1) |
| (II-10) | (II-a-4) | (II-c-1) |
| (II-11) | (II-a-5) | (II-c-1) |
| (II-12) | (II-a-6) | (II-c-1) |
| (II-13) | (II-a-7) | (II-c-1) |
| (II-14) | (II-a-1) | (II-c-2) |
| (II-15) | (II-a-2) | (II-c-2) |
| (II-16) | (II-a-3) | (II-c-2) |
| (II-17) | (II-a-5) | (II-c-2) |
| (II-18) | (II-a-7) | (II-c-2) |
| (II-19) | (II-a-1) | (II-c-3) |
| (II-20) | (II-a-2) | (II-c-3) |
| (II-21) | (II-a-3) | (II-c-3) |
| (II-22) | (II-a-5) | (II-c-3) |
| (II-23) | (II-a-7) | (II-c-3) |
| (II-24) | (II-a-1) | (II-c-4) |
| (II-25) | (II-a-3) | (II-c-4) |
| (II-26) | (II-a-4) | (II-c-4) |
| (II-27) | (II-a-5) | (II-c-4) |
| (II-28) | (II-a-6) | (II-c-4) |
| (II-29) | (II-a-7) | (II-c-4) |
| (II-30) | (II-a-1) | (II-c-5) |
| (II-31) | (II-a-2) | (II-c-5) |
| (II-32) | (II-a-3) | (II-c-5) |
| (II-33) | (II-a-5) | (II-c-5) |
| (II-34) | (II-a-7) | (II-c-5) |
| (II-35) | (II-a-1) | (II-c-6) |
| (II-36) | (II-a-2) | (II-c-6) |
| (II-37) | (II-a-3) | (II-c-6) |
| (II-38) | (II-a-5) | (II-c-6) |
| (II-39) | (II-a-7) | (II-c-6) |
| (II-40) | (II-a-1) | (II-c-7) |
| (II-41) | (II-a-3) | (II-c-7) |
| (II-42) | (II-a-4) | (II-c-7) |
| (II-43) | (II-a-5) | (II-c-7) |
| (II-44) | (II-a-6) | (II-c-7) |
| (II-45) | (II-a-7) | (II-c-7) |
| (II-46) | (II-a-1) | (II-c-8) |
| (II-47) | (II-a-2) | (II-c-8) |
| (II-48) | (II-a-3) | (II-c-8) |
| (II-49) | (II-a-5) | (II-c-8) |
| (II-50) | (II-a-7) | (II-c-8) |
| (II-51) | (II-a-1) | (II-c-9) |
| (II-52) | (II-a-2) | (II-c-9) |

TABLE 1-continued

| Acid generator (II) | Sulfonate anion | Organic cation |
|---|---|---|
| (II-53) | (II-a-3) | (II-c-9) |
| (II-54) | (II-a-5) | (II-c-9) |
| (II-55) | (II-a-7) | (II-c-9) |
| (II-56) | (II-a-1) | (II-c-10) |
| (II-57) | (II-a-3) | (II-c-10) |
| (II-58) | (II-a-4) | (II-c-10) |
| (II-59) | (II-a-5) | (II-c-10) |
| (II-60) | (II-a-6) | (II-c-10) |
| (II-61) | (II-a-7) | (II-c-10) |
| (II-62) | (II-a-1) | (II-c-11) |
| (II-63) | (II-a-2) | (II-c-11) |
| (II-64) | (II-a-3) | (II-c-11) |
| (II-65) | (II-a-5) | (II-c-11) |
| (II-66) | (II-a-7) | (II-c-11) |
| (II-67) | (II-a-1) | (II-c-12) |
| (II-68) | (II-a-2) | (II-c-12) |
| (II-69) | (II-a-3) | (II-c-12) |
| (II-70) | (II-a-5) | (II-c-12) |
| (II-71) | (II-a-7) | (II-c-12) |
| (II-72) | (II-a-1) | (II-c-13) |
| (II-73) | (II-a-4) | (II-c-13) |
| (II-74) | (II-a-5) | (II-c-13) |
| (II-75) | (II-a-6) | (II-c-13) |
| (II-76) | (II-a-7) | (II-c-13) |
| (II-77) | (II-a-1) | (II-c-14) |
| (II-78) | (II-a-2) | (II-c-14) |
| (II-79) | (II-a-3) | (II-c-14) |
| (II-80) | (II-a-4) | (II-c-14) |
| (II-81) | (II-a-5) | (II-c-14) |
| (II-82) | (II-a-6) | (II-c-14) |
| (II-83) | (II-a-7) | (II-c-14) |
| (II-84) | (II-a-1) | (II-c-15) |
| (II-85) | (II-a-2) | (II-c-15) |
| (II-86) | (II-a-3) | (II-c-15) |
| (II-87) | (II-a-5) | (II-c-15) |
| (II-88) | (II-a-7) | (II-c-15) |
| (II-89) | (II-a-1) | (II-c-16) |
| (II-90) | (II-a-2) | (II-c-16) |
| (II-91) | (II-a-3) | (II-c-16) |
| (II-92) | (II-a-5) | (II-c-16) |
| (II-93) | (II-a-7) | (II-c-16) |
| (II-94) | (II-a-1) | (II-c-17) |
| (II-95) | (II-a-2) | (II-c-17) |
| (II-96) | (II-a-3) | (II-c-17) |
| (II-97) | (II-a-5) | (II-c-17) |
| (II-98) | (II-a-7) | (II-c-17) |
| (II-99) | (II-a-1) | (II-c-18) |
| (II-100) | (II-a-2) | (II-c-18) |
| (II-101) | (II-a-3) | (II-c-18) |
| (II-102) | (II-a-5) | (II-c-18) |
| (II-103) | (II-a-7) | (II-c-18) |
| (II-104) | (II-a-1) | (II-c-19) |
| (II-105) | (II-a-2) | (II-c-19) |
| (II-106) | (II-a-3) | (II-c-19) |
| (II-107) | (II-a-5) | (II-c-19) |
| (II-108) | (II-a-7) | (II-c-19) |
| (II-109) | (II-a-1) | (II-c-20) |
| (II-110) | (II-a-3) | (II-c-20) |
| (II-111) | (II-a-4) | (II-c-20) |
| (II-112) | (II-a-5) | (II-c-20) |
| (II-113) | (II-a-6) | (II-c-20) |
| (II-114) | (II-a-7) | (II-c-20) |
| (II-115) | (II-a-1) | (II-c-21) |
| (II-116) | (II-a-2) | (II-c-21) |
| (II-117) | (II-a-3) | (II-c-21) |
| (II-118) | (II-a-5) | (II-c-21) |
| (II-119) | (II-a-7) | (II-c-21) |
| (II-120) | (II-a-1) | (II-c-22) |
| (II-121) | (II-a-2) | (II-c-22) |

TABLE 1-continued
| Acid generator (II) | Sulfonate anion | Organic cation |
|---|---|---|
| (II-122) | (II-a-3) | (II-c-22) |
| (II-123) | (II-a-5) | (II-c-22) |
| (II-124) | (II-a-7) | (II-c-22) |
Among these, preferable examples thereof include the acid generators described below.
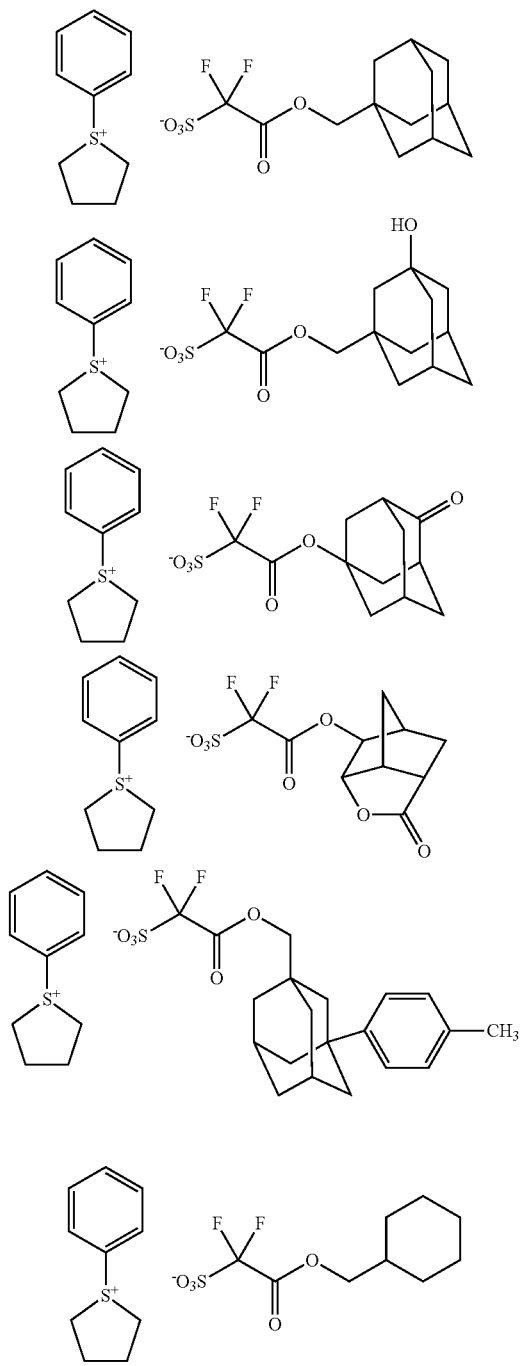
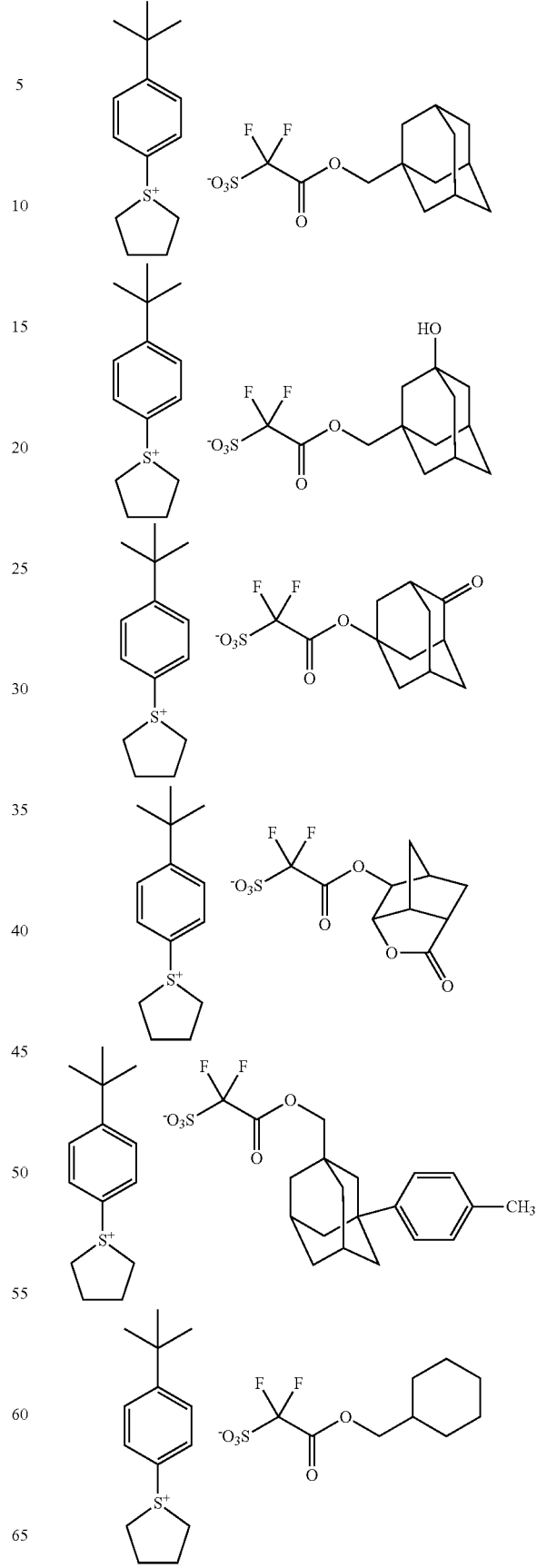

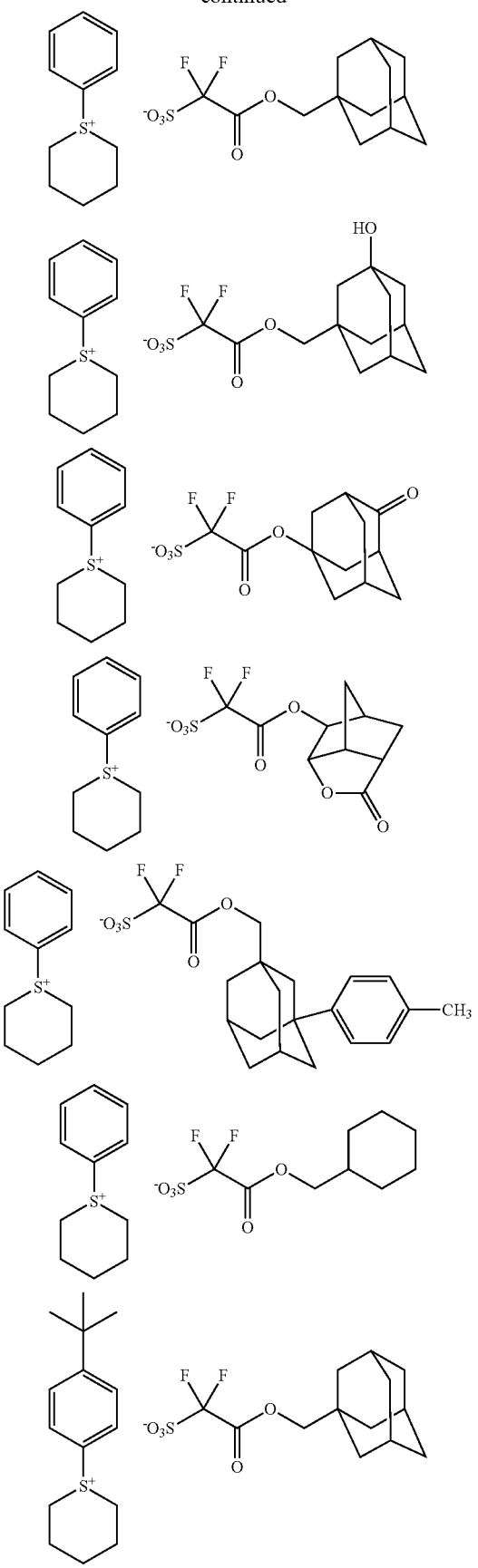
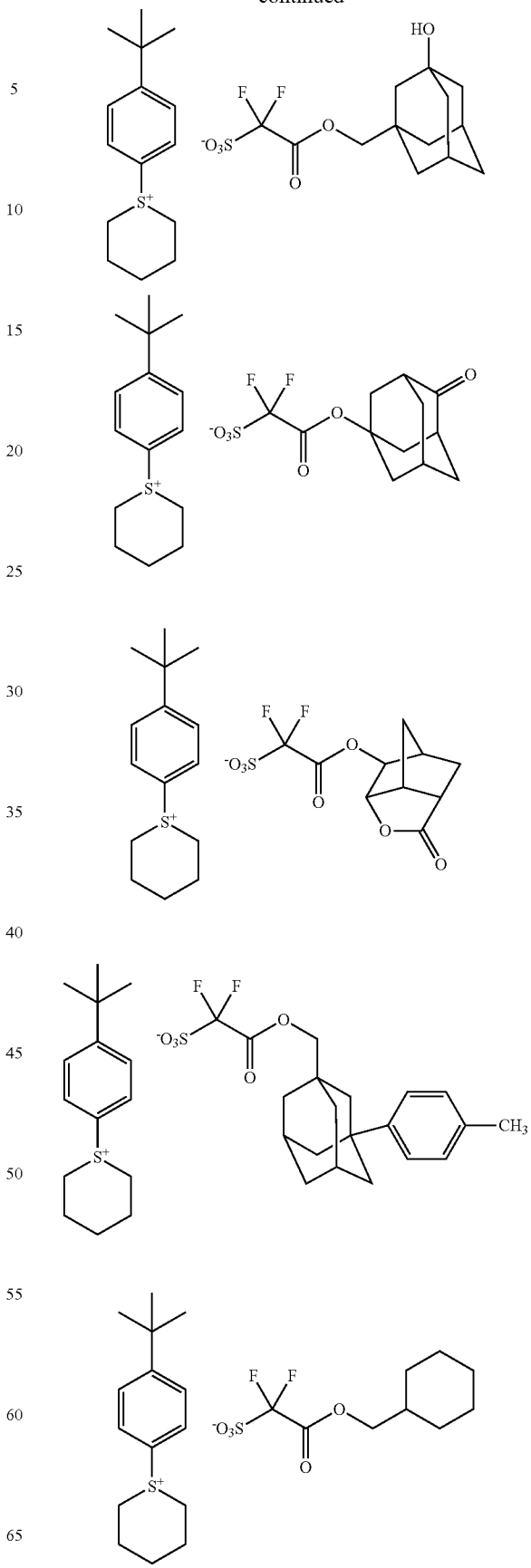

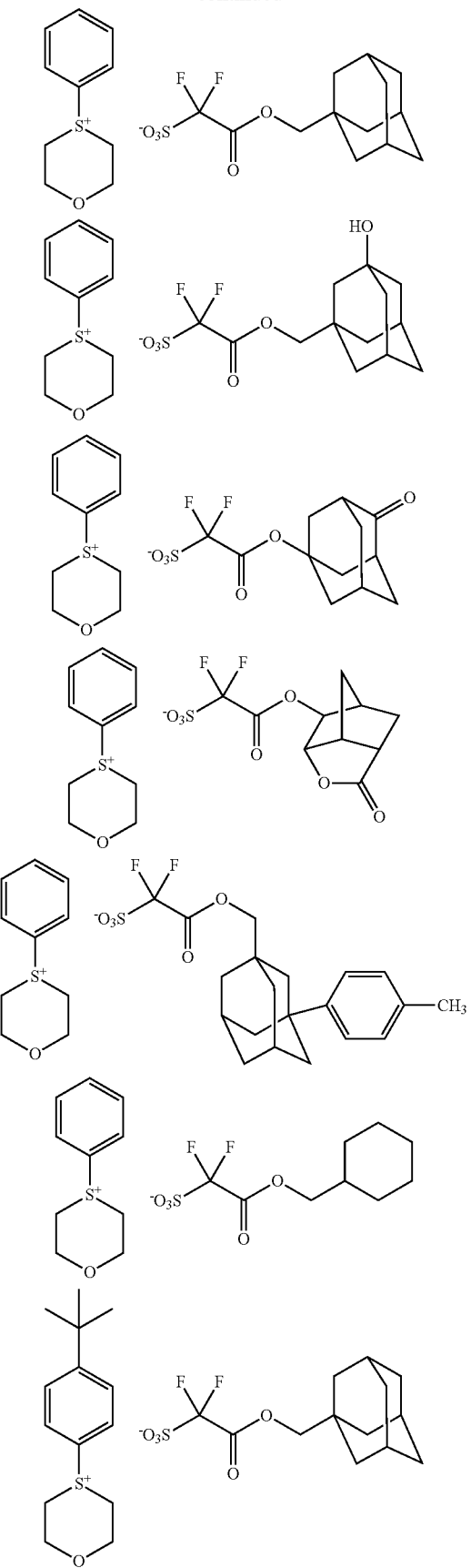
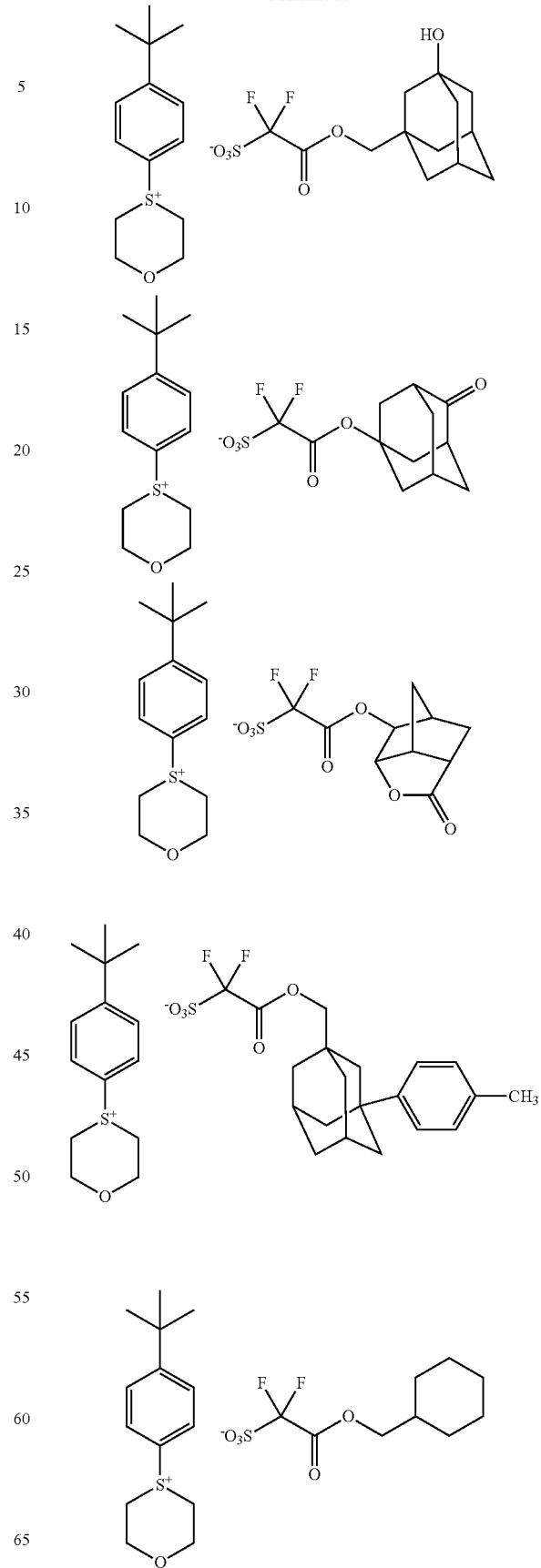

-continued

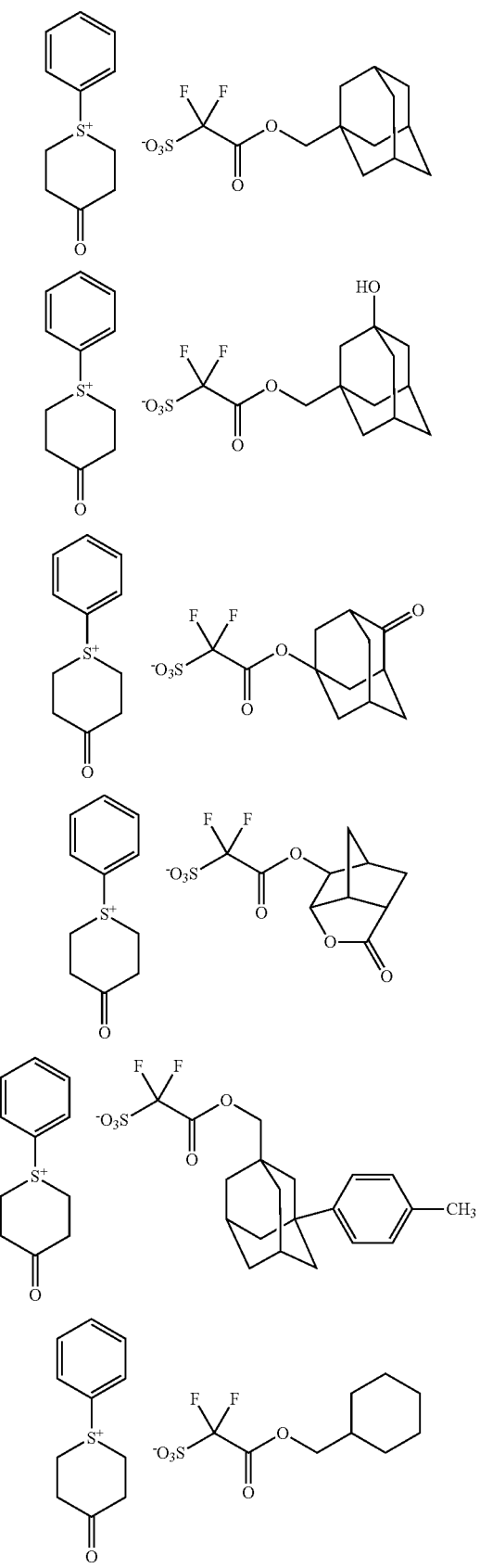

The acid generator (II) can be produced by a known method in the field. In the formula below, $R^{II1}$, $R^{II2}$, $R^{II3}$, $R^{II4}$, $R^{II5}$, $R^{II6}$, $R^{II7}$, $R^{II8}$, $L^{II1}$, s, n and $Y^{II1}$ represent the same meaning as described above.

For example, the salt represented by the formula (II) can be obtained by reacting a salt represented by the formula (II-a) with a salt represented by the formula (II-b) in a solvent.

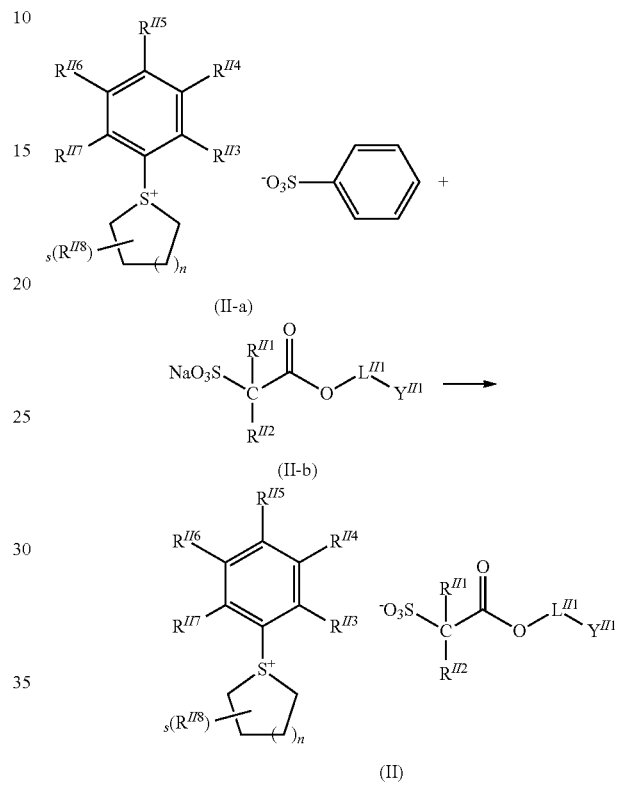

Examples of the solvent include chloroform.

The salt represented by the formula (II-b) can be synthesized according to the method described in JP-2008-209917A.

The salt represented by the formula (II-a) can be obtained by reacting a salt represented by the formula (II-c) with a compound represented by the formula (II-d) in a solvent in the presence of a catalyst.

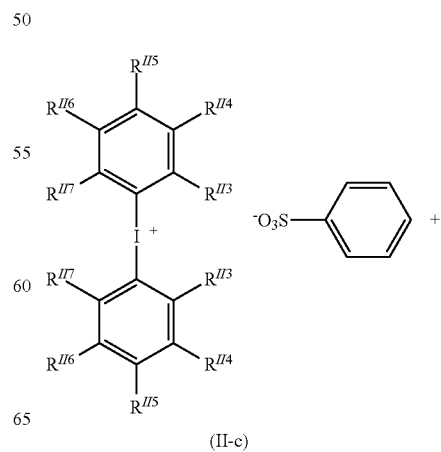

-continued

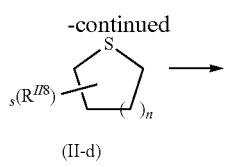

(II-d)

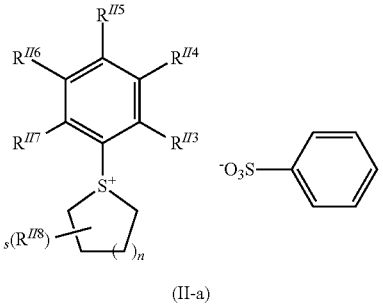

(II-a)

Examples of the solvent include monochloro benzene.
Examples of catalyst include copper (II) dibenzoate.
Examples of the salt represented by the formula (II-c) include diphenyl iodonium benzene sulfonate.
Examples of the compound represented by the formula (II-d) include pentamethylene sulfide, 1,4-tioxane, tetrahydrothiophene.

The salt represented by the formula (II) can be also obtained by reacting a salt represented by the formula (II-a') with a compound represented by the formula (II-b') in a solvent in the presence of

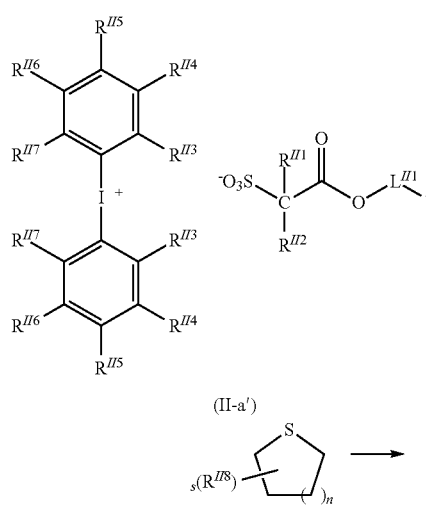

(II)

Examples of the solvent include monochloro benzene.
Examples of catalyst include copper (II) dibenzoate.

Examples of the salt represented by the formula (II-b') include pentamethylene sulfide, 1,4-tioxane, tetrahydrothiophene.

The salt represented by the formula (II-a') can be obtained by reacting a salt represented by the formula (II-c') with a compound represented by the formula (II-d') in a solvent.

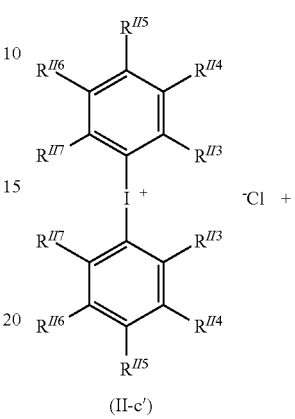

(II-c')

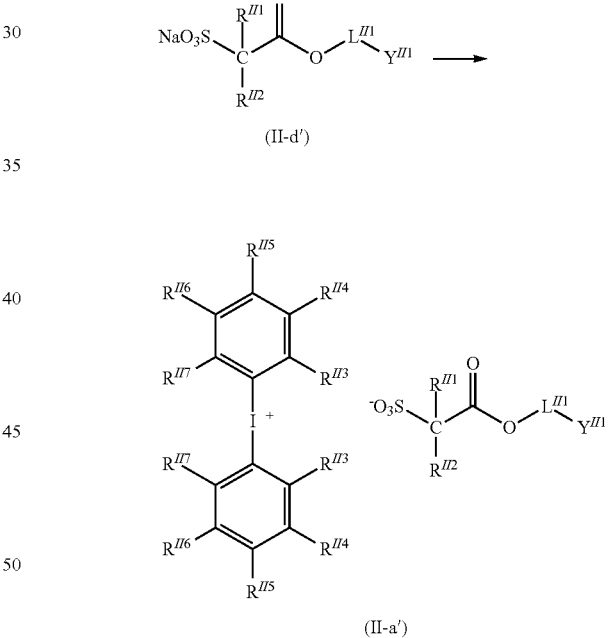

(II-a')

Examples of the solvent include chloroform and water.
Examples of the salt represented by the formula (II-c') include diphenyliodonium chloride.
The salt represented by the formula (II-d') can be synthesized according to the method described in JP-2008-209917A.

In the resist composition of the present invention, the acid generator (II) may be used as a single compound or as a combination of two or more compounds.

<Acid Generator (III)>

The acid generator (III) which may be included in the resist composition of the present invention preferably includes a salt represented by the formula (III);

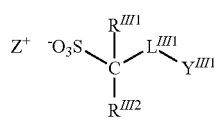

(III)

wherein $R^{III1}$ and $R^{III2}$ independently represent a fluorine atom or a $C_1$ to $C_6$ perfluoroalkyl group;

$L^{III1}$ represents a single bond or a $C_1$ to $C_{17}$ divalent saturated hydrocarbon group, one or more hydrogen atom in the saturated hydrocarbon group may be replaced by a fluorine atom or a hydroxy group, and one or more —$CH_2$— contained in the saturated hydrocarbon group may be replaced by —O— or —CO—;

$Y^{III1}$ represents an optionally substituted $C_1$ to $C_{18}$ alkyl group or an optionally substituted $C_3$ to $C_{18}$ alicyclic hydrocarbon group, and one or more —$CH_2$— contained in the alkyl group and alicyclic hydrocarbon group may be replaced by —O—, —CO— or —$SO_2$—; and $Z^+$ represents an organic cation.

In the formula (III), a moiety having a negative charge in which an organic cation, $Z^+$, having a positive charge is removed may refer to as a sulfonate anion.

Examples of the perfluoroalkyl group of $R^{III1}$ and $R^{III2}$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

Among these, $R^{III1}$ and $R^{III2}$ independently are preferably trifluoromethyl or fluorine atom, and more preferably a fluorine atom.

Examples of the a divalent saturated hydrocarbon group of $L^{III1}$ include any of;

a chain alkanediyl group such as methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, ethane-1,1-diyl, propan-1,1-diyl and propan-2,2-diyl groups;

a branched chain alkanediyl group such as a group in which a chain alkanediyl group is bonded a side chain of a $C_1$ to $C_4$ alkyl group such as methyl, ethyl, propyl, isopropyl, butyl, sec-butyl and tert-butyl, for example, butane-1,3-diyl, 2-methylpropane-1,3-diyl, 2-methylpropane-1,2-diyl, pentane-1,4-diyl and 2-methylbutane-1,4-diyl groups;

a mono-alicyclic hydrocarbon group such as a cycloalkanediyl group, e.g., cyclobutan-1,3-diyl, cyclopentan-1,3-diyl, cyclohexane-1,2-diyl, 1-methylhexane-1,2-diyl, cyclohexane-1,4-diyl, cyclooctan-1,2-diyl, cyclooctan-1,5-diyl groups;

a poly-alicyclic hydrocarbon group such as norbornane-2,3-diyl, norbornane-1,4-diyl, norbornane-2,5-diyl, adamantane-1,5-diyl and adamantane-2,6-diyl groups; and a combination of two or more groups.

Examples of the saturated hydrocarbon group of $L^{III1}$ in which one or more —$CH_2$— contained in the saturated hydrocarbon group is replaced by —O— or —CO— include groups represented by the formula (b1-1) to the formula (b1-7) below. In the formula (b1-1) to the formula (b1-7), the group is represented so as to correspond with two sides of the formula (III), that is, the left side of the group bonds to carbon atom of $C(R^{III1})(R^{III2})$— and the right side of the group bonds to —Y (examples of the formula (b1-1) to the formula (b1-7) are the same as above). * represents a bond.

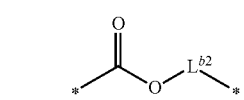

(b1-1)

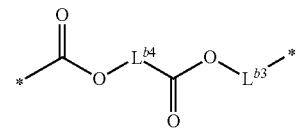

(b1-2)

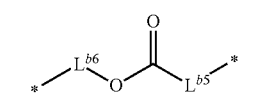

(b1-3)

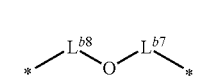

(b1-4)

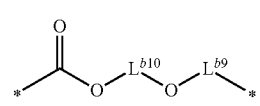

(b1-5)

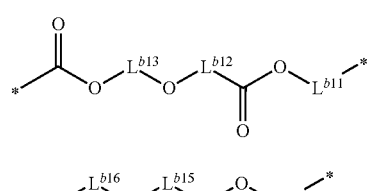

(b1-6)

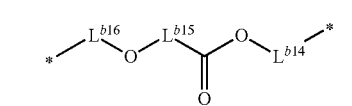

(b1-7)

wherein $L^{b2}$ represents a single bond or a $C_1$ to $C_{15}$ divalent saturated hydrocarbon group;

$L^{b3}$ represents a single bond or a $C_1$ to $C_{12}$ divalent saturated hydrocarbon group;

$L^{b4}$ represents a $C_1$ to $C_{13}$ divalent saturated hydrocarbon group, the total number of the carbon atoms in $L^{b3}$ and $L^{b4}$ is at most 13;

$L^{b5}$ represents a single bond or a $C_1$ to $C_{14}$ divalent saturated hydrocarbon group;

$L^{b6}$ represents a $C_1$ to $C_{15}$ divalent saturated hydrocarbon group, the total number of the carbon atoms in $L^{b5}$ and $L^{b6}$ is at most 15;

$L^{b7}$ represents a single bond or a $C_1$ to $C_{15}$ divalent saturated hydrocarbon group;

$L^{b8}$ represents a $C_1$ to $C_{15}$ divalent saturated hydrocarbon group, the total number of the carbon atoms in $L^{b7}$ and $L^{b8}$ is at most 16;

$L^{b9}$ represents a single bond or a $C_1$ to $C_{13}$ divalent saturated hydrocarbon group;

$L^{b10}$ represents a $C_1$ to $C_{14}$ divalent saturated hydrocarbon group, the total number of the carbon atoms in $L^{b9}$ and $L^{b10}$ is at most 14;

$L^{b11}$ and $L^{b12}$ independently represent a single bond or a $C_1$ to $C_{11}$ divalent saturated hydrocarbon group;

$L^{b13}$ represents a $C_1$ to $C_{12}$ divalent saturated hydrocarbon group, the total number of the carbon atoms in $L^{b11}$, $L^{b12}$ and $L^{b13}$ is at most 12;

$L^{b14}$ and $L^{b15}$ independently represent a single bond or a $C_1$ to $C_{13}$ divalent saturated hydrocarbon group;

$L^{b16}$ represents a $C_1$ to $C_{14}$ divalent saturated hydrocarbon group, the total number of the carbon atoms in $L^{b14}$, $L^{b15}$ and $L^{b16}$ is at most 14.

Among these, $L^{III1}$ is preferably the groups represented by the formula (b1-1) to the formula (b1-4), more preferably the group represented by the formula (b1-1) or the formula (b1-2), and still more preferably the group represented by the formula (b1-1). In particular, the divalent group represented by the formula (b1-1) in which $L^{b2}$ represents a single bond or —CH$_2$— is preferable.

Specific examples of the divalent group represented by the formula (b1-1) include groups below. In the formula below, * represent a bond.

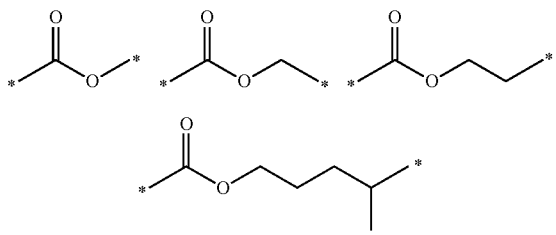

Specific examples of the divalent group represented by the formula (b1-2) include groups below.

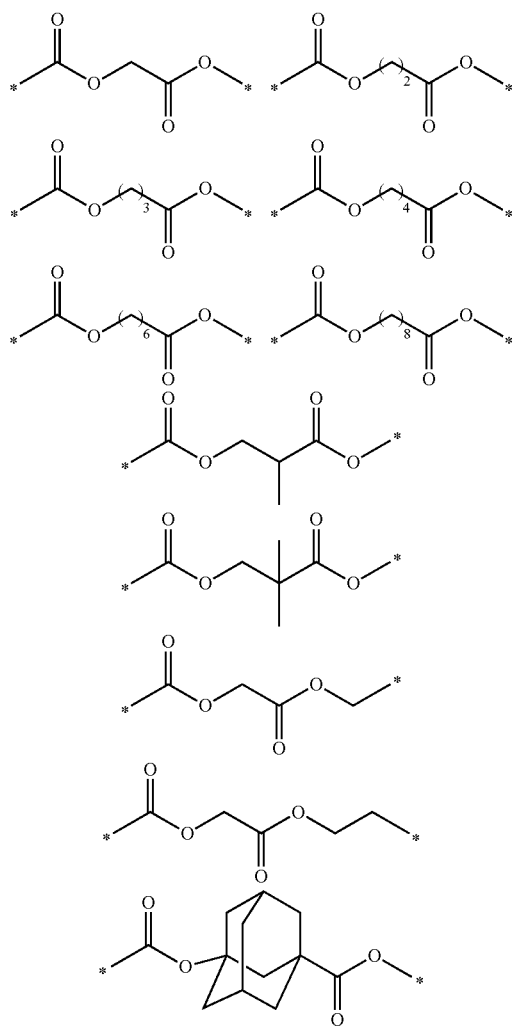

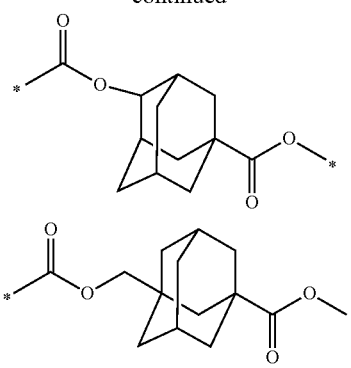

Specific examples of the divalent group represented by the formula (b1-3) include groups below.

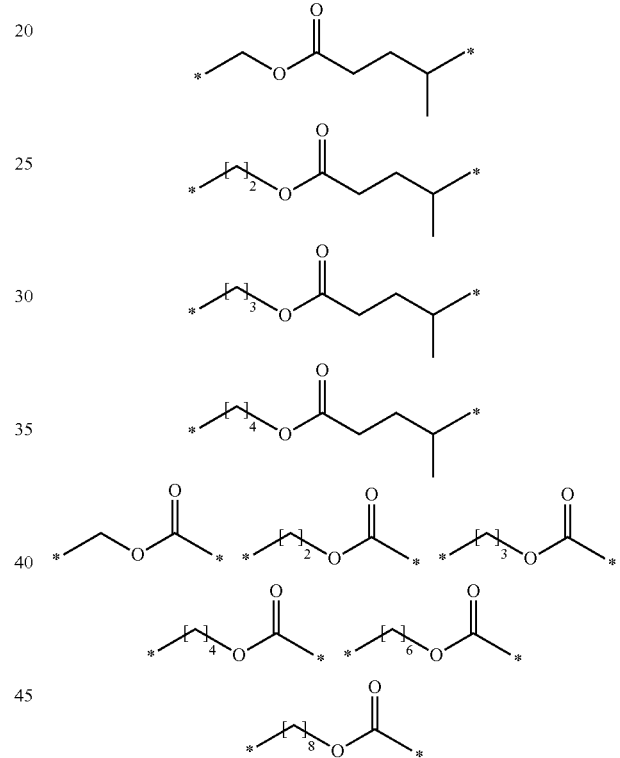

Specific examples of the divalent group represented by the formula (b1-4) include a group below.

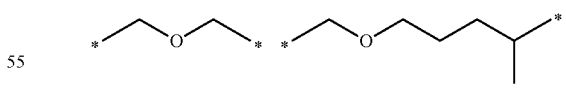

Specific examples of the divalent group represented by the formula (b1-5) include groups below.

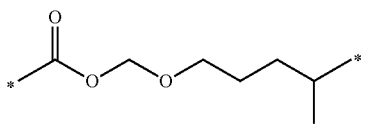

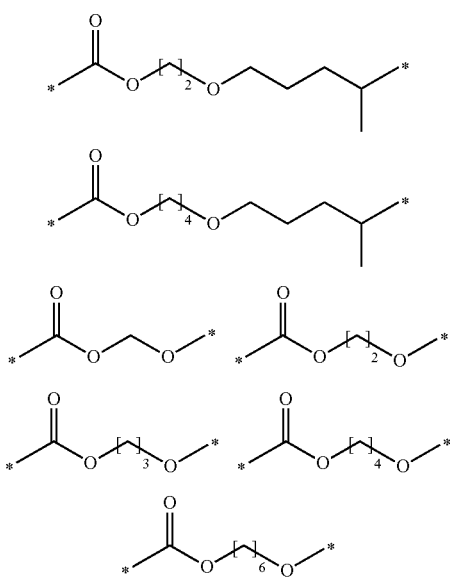
Specific examples of the divalent group represented by the formula (b1-6) include groups below.
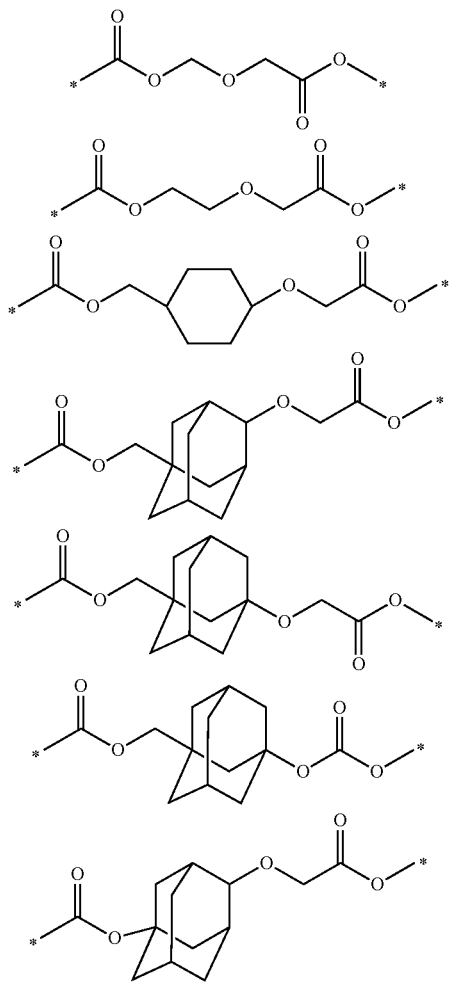
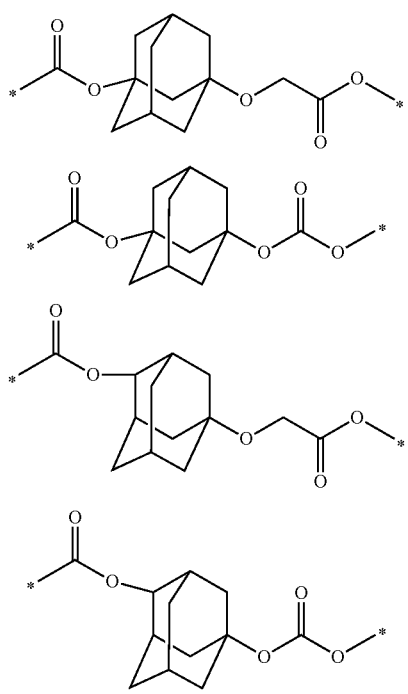
Specific examples of the divalent group represented by the formula (b1-7) include groups below.
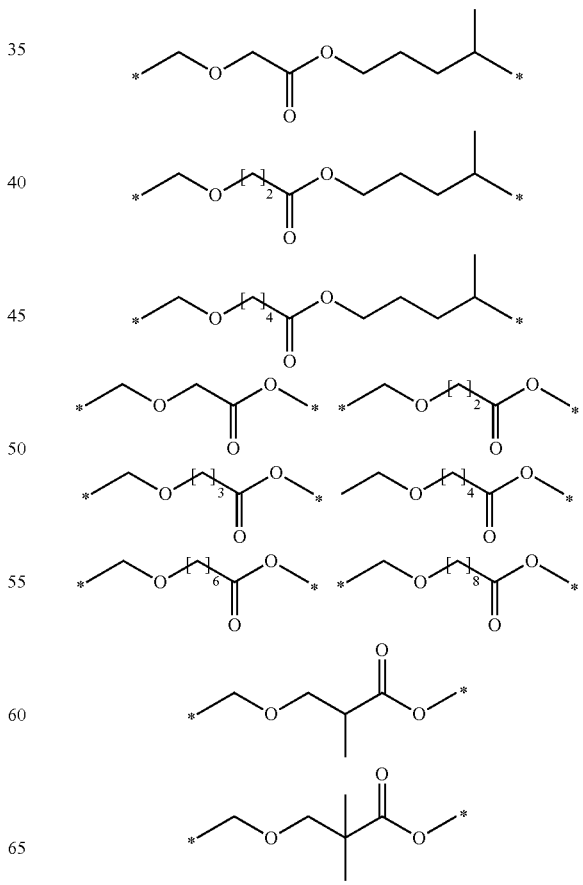

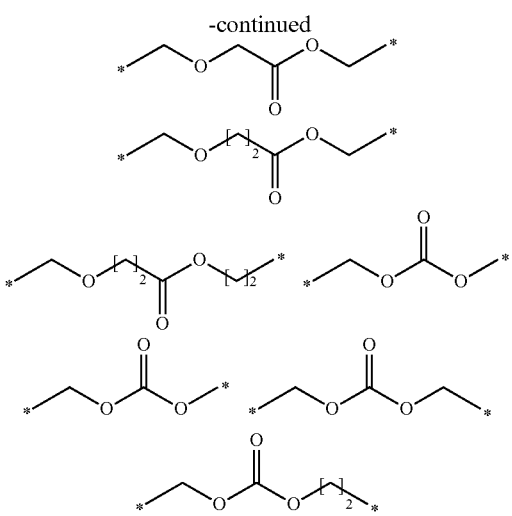

The divalent saturated hydrocarbon group of $L^{III1}$ which one or more hydrogen atom in the saturated hydrocarbon group may be replaced by a fluorine atom or a hydroxy group include as follows.

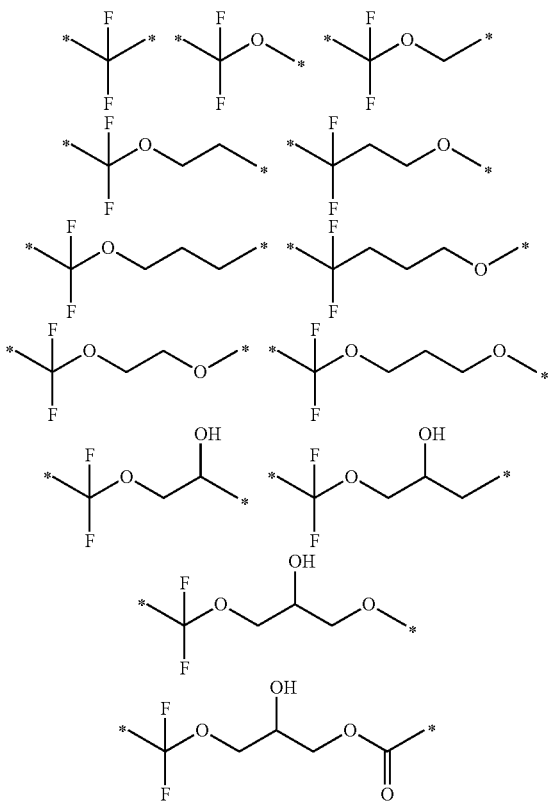

The alkyl group of $Y^{III1}$ is preferably a $C_1$ to $C_6$ alkyl group.

Examples of the alicyclic hydrocarbon group of $Y^{III1}$ include groups represented by the formula (Y1) to the formula (Y11) and the formula (Y27) to the formula (Y29) described above.

$Y^{III1}$ may have a substituent.

Examples of the substituent of $Y^{III1}$ include a halogen atom, a hydroxy group, an oxo group, a $C_1$ to $C_{12}$ alkyl group, a hydroxy group-containing $C_1$ to $C_{12}$ alkyl group, a $C_3$ to $C_{16}$ alicyclic hydrocarbon group, a $C_1$ to $C_{12}$ alkoxy group, a $C_6$ to $C_{18}$ aromatic hydrocarbon group, a $C_7$ to $C_{21}$ aralkyl group, a $C_2$ to $C_4$ acyl group, a glycidyloxy group or a —$(CH_2)_{j2}$—O—CO—$R^{b1}$ group, wherein $R^{b1}$ represents a $C_1$ to $C_{16}$ alkyl group, a $C_3$ to $C_{16}$ alicyclic hydrocarbon group or a $C_6$ to $C_{18}$ aromatic hydrocarbon group, j2 represents an integer of 0 to 4. The alkyl group, alicyclic hydrocarbon group, aromatic hydrocarbon group and the aralkyl group of the substituent may further have a substituent such as a $C_1$ to $C_6$ alkyl group, a halogen atom, a hydroxy group and an oxo group.

Examples of the hydroxy group-containing alkyl group include hydroxymethyl and hydroxyethyl groups Examples of the halogen atom, the alkyl group, the alicyclic hydrocarbon group, the alkoxyl group, the aromatic hydrocarbon group, the aralkyl group and the acyl group include the same examples, respectively, described above.

Examples of the alicyclic hydrocarbon group of $Y^{III1}$ in which one or more —$CH_2$— contained in the alicyclic hydrocarbon group is replaced by —O—, —CO— or —$SO_2$— include a cyclic ether group which is a group in which one or two —$CH_2$— contained in the alicyclic hydrocarbon group is replaced by the —O—;

an alicyclic hydrocarbon group which is a group in which one or two —$CH_2$— contained in the alicyclic hydrocarbon group is replaced by the —CO—;

a sultone ring group which is a group in which an adjacent two —$CH_2$— contained in the alicyclic hydrocarbon group are replaced by the —O— and —$SO_2$—, respectively;

a lactone ring group which is a group in which an adjacent two —$CH_2$— contained in the alicyclic hydrocarbon group are replaced by the —O— and —CO—, respectively.

Specific examples of the alicyclic hydrocarbon group of $Y^{III1}$ in which one or more —$CH_2$— contained in the alicyclic hydrocarbon group is replaced by —O—, —CO— or —$SO_2$— include groups represented by the formula (Y12) to the formula (Y26) of the above.

Among these, the alicyclic hydrocarbon group is preferably any one of groups represented by the formula (Y1) to the formula (Y19), more preferably any one of groups represented by the formula (Y11), (Y14), (Y15) or (Y19), and still more preferably group represented by the formula (Y11) or (Y14).

Examples of $Y^{III1}$ include the groups below.

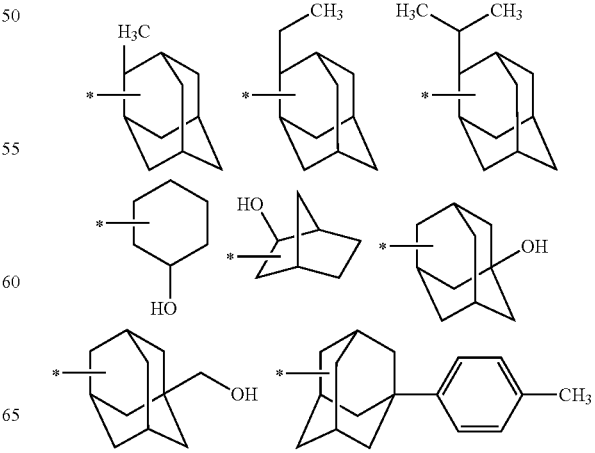

-continued

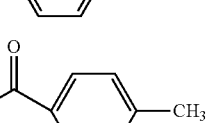
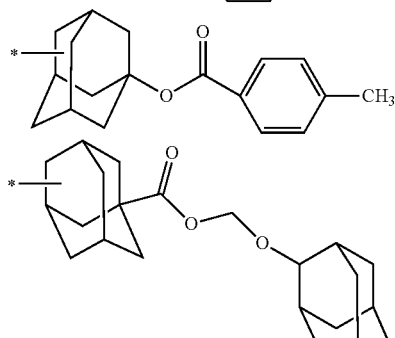
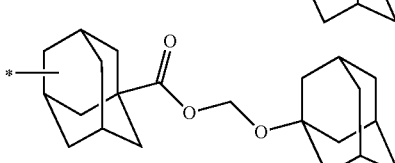
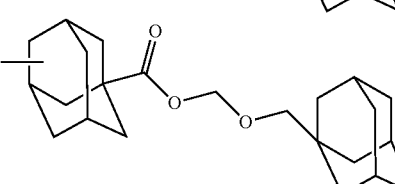
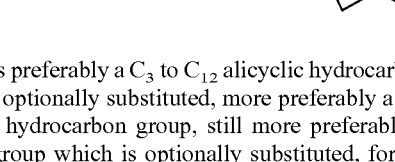
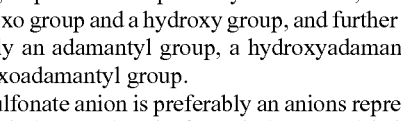

$Y^{III1}$ is preferably a $C_3$ to $C_{12}$ alicyclic hydrocarbon group which is optionally substituted, more preferably a $C_3$ to $C_{12}$ alicyclic hydrocarbon group, still more preferably an adamantyl group which is optionally substituted, for example, with an oxo group and a hydroxy group, and further still more preferably an adamantyl group, a hydroxyadamantyl group and an oxoadamantyl group.

The sulfonate anion is preferably an anions represented by the formula (III1-1-1) to the formula (III1-1-11) below. In the formula (III1-1-1) to the formula (III1-1-11), $R^{III1}$ and $R^{III2}$ and $L^{III1}$ represent the same meaning as defined above. $R^{b2}$ and $R^{b3}$ independently represent a $C_1$ to $C_4$ alkyl group (preferably methyl group).

(III1-1-1)
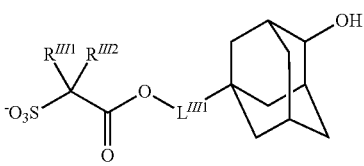

(III1-1-2)
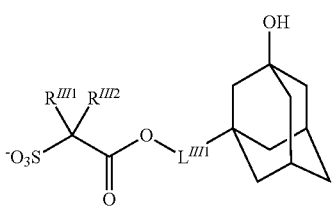

-continued (III1-1-3)
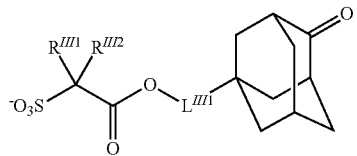

(III1-1-4)
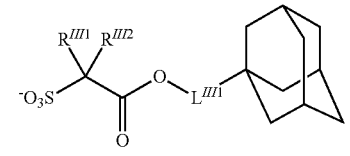

(III1-1-5)
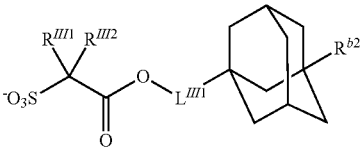

(III1-1-6)
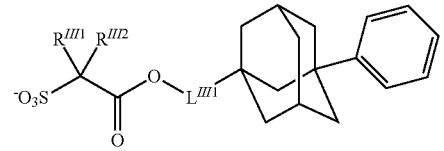

(III1-1-7)
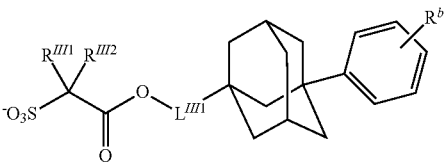

(III1-1-8)
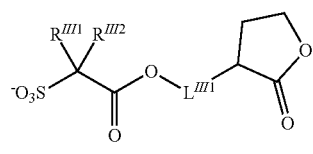

(III1-1-9)
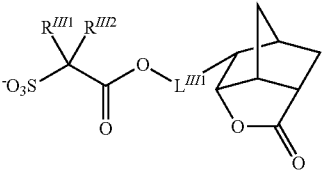

(III1-1-10)
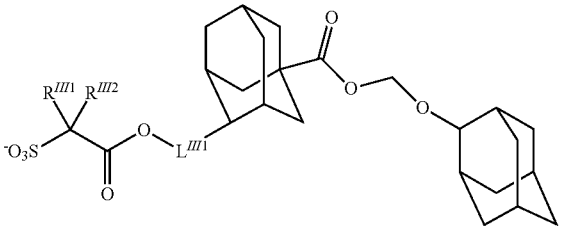

(III1-1-11)

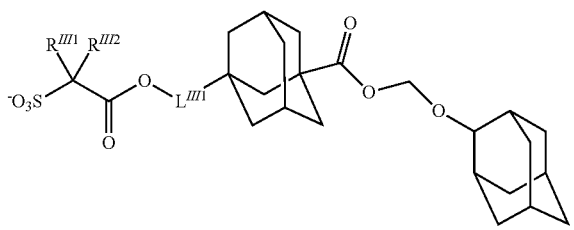

Specific examples of the sulfonate anion include sulfonate anions described in JP2010-204646A.

Examples of the cation of the acid generator (III) include an organic onium cation such as an organic sulfonium cation, organic iodonium cation, organic ammonium cation, benzothiazolium cation and organic phosphonium cation. Among these, organic sulfonium cation and organic iodonium cation are preferable, and aryl sulfonium cation is more preferable.

$Z^+$ of the formula (III) is preferably represented by any of the formula (b2-1) to the formula (b2-4).

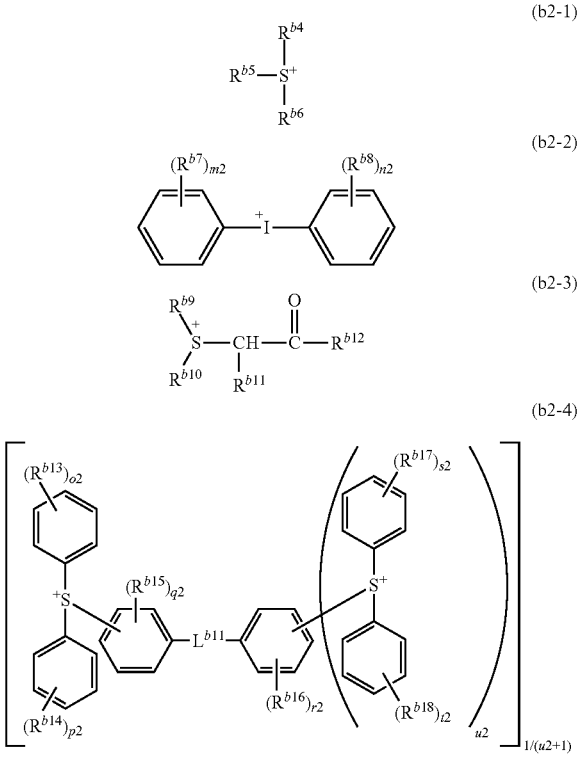

wherein $R^{b4}$, $R^{b5}$ and $R^{b6}$ independently represent a $C_1$ to $C_{30}$ alkyl group, a $C_3$ to $C_{18}$ alicyclic hydrocarbon group or a $C_6$ to $C_{36}$ aromatic hydrocarbon group, or $R^{b4}$ and $R^{b5}$ may be bonded together to form a sulfur-containing ring, one or more hydrogen atoms contained in the alkyl group may be replaced by a hydroxy group, a $C_3$ to $C_{15}$ alicyclic hydrocarbon group, a $C_1$ to $C_{12}$ alkoxy group or a $C_6$ to $C_{15}$ aromatic hydrocarbon group, one or more hydrogen atoms contained in the alicyclic hydrocarbon group may be replaced by a halogen atom, a $C_1$ to $C_{18}$ alkyl group, a $C_2$ to $C_4$ acyl group and a glycidyloxy group, one or more hydrogen atoms contained in the aromatic hydrocarbon group may be replaced by a halogen atom, a hydroxy group or a $C_1$ to $C_{12}$ alkoxy group;

$R^{b7}$ and $R^{b8}$ in each occurrence independently represent a hydroxy group, a $C_1$ to $C_{12}$ alkyl group or a $C_1$ to $C_{12}$ alkoxyl group;

m2 and n2 independently represent an integer of 0 to 5;

$R^{b9}$ and $R^{b10}$ independently represent a $C_1$ to $C_{18}$ alkyl group or a $C_3$ to $C_{18}$ alicyclic hydrocarbon group, or $R^{b9}$ and $R^{b10}$ may be bonded together with a sulfur atom bonded thereto to form a sulfur-containing 3- to 12-membered (preferably 3- to 7-membered) ring, and one or more —CH$_2$— contained in the ring may be replaced by —O—, —CO— or —S—;

$R^{b11}$ represents a hydrogen atom, a $C_1$ to $C_{18}$ alkyl group, a $C_3$ to $C_{18}$ alicyclic hydrocarbon group or a $C_6$ to $C_{18}$ aromatic hydrocarbon group;

$R^{b12}$ represents a $C_1$ to $C_{12}$ alkyl group, a $C_3$ to $C_{18}$ alicyclic hydrocarbon group or a $C_6$ to $C_{18}$ aromatic hydrocarbon group, one or more hydrogen atoms contained in the alkyl group may be replaced by a $C_6$ to $C_{18}$ aromatic hydrocarbon group, one or more hydrogen atoms contained in the aromatic hydrocarbon group may be replaced by a $C_1$ to $C_{12}$ alkoxy group or a $C_1$ to $C_{12}$ alkyl carbonyloxy group;

$R^{b11}$ and $R^{b12}$ may be bonded together with —CH—CO— bonded thereto to form a 3- to 12-membered (preferably a 3- to 7-membered) ring, and one or more —CH$_2$— contained in the ring may be replaced by —O—, —CO— or —S—;

$R^{b13}$, $R^{b14}$, $R^{b15}$, $R^{b16}$, $R^{b17}$ and $R^{b18}$ in each occurrence independently represent a hydroxy group, a $C_1$ to $C_{12}$ alkyl group or a $C_1$ to $C_{12}$ alkoxy group;

$L^{b11}$ represents —S— or —O—;

o2, p2, s2 and t2 independently represent an integer of 0 to 5;

q2 or r2 independently represent an integer of 0 to 4;

u2 represents an integer of 0 or 1.

Examples of the alkyl group include methyl, ethyl, n-propyl, isopropyl, n-butyl, sec-butyl, tert-butyl, pentyl, hexyl, octyl and 2-ethylhexyl groups. In particular, the alkyl group of $R^{b9}$ to $R^{b12}$ is preferably a $C_1$ to $C_{12}$ alkyl group.

Examples of the alkyl group in which one or more hydrogen atoms are replaced by an alicyclic hydrocarbon group include 1-(1-adamatane-1-yl)-alkane-1-yl group.

Examples of the alicyclic hydrocarbon group include a monocyclic hydrocarbon groups such as cyclopropyl, cyclobutyl, cyclopentyl, cyclohexyl, cycloheptyl, cyclodecyl; a polycyclic hydrocarbon groups such as decahydronaphtyl, adamantyl and norbornyl (i.e., bicyclo[2.2.1]heptyl), groups as well as groups below.

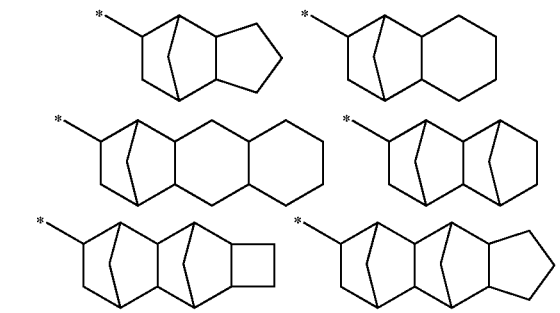

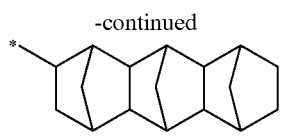

In particular, the alicyclic hydrocarbon group of $R^{b9}$ to $R^{b12}$ is preferably a $C_3$ to $C_{18}$ alicyclic hydrocarbon group, and more preferably a $C_4$ to $C_{12}$ alicyclic hydrocarbon group.

Examples of the alicyclic hydrocarbon group in which one or more hydrogen atoms are replaced by an alkyl group include methyl cyclohexyl, dimethyl cyclohexyl, 2-alkyladamantane-2-yl, methyl norbornyl and isobornyl groups.

Examples of the aromatic hydrocarbon group include phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

When the aromatic hydrocarbon include an alkyl group or an alicyclic hydrocarbon group, a $C_1$ to $C_{18}$ alkyl group or a $C_3$ to $C_{18}$ alicyclic hydrocarbon group is preferable.

Examples of the alkyl group in which one or more hydrogen atoms are replaced by an aromatic hydrocarbon group, i.e., aralkyl group include benzyl, phenethyl, phenylpropyl, trityl, naphthylmethyl and naphthylethyl groups.

Examples of the alkoxyl group include methoxy, ethoxy, propoxy, propoxy, butoxy, pentyloxy, hexyloxy, heptyloxy, octyloxy, decyloxy and dodecyloxy groups.

Examples of the halogen atom include fluorine, chlorine, bromine and iodine atoms.

Examples of the acyl group include acetyl, propionyl and butyryl groups.

Examples of the alkyl carbonyloxy group include methyl carbonyloxy, ethyl carbonyloxy, n-propyl carbonyloxy, isopropyl carbonyloxy, n-butyl carbonyloxy, sec-butyl carbonyloxy, tert-butyl carbonyloxy, pentyl carbonyloxy, hexyl carbonyloxy, octylcarbonyloxy and 2-ethylhexylcarbonyloxy groups.

The sulfur-containing ring formed by $R^{b4}$ and $R^{b5}$ may be either of monocyclic or polycyclic, aromatic or non-aromatic, or saturated or unsaturated ring, and may further have at least one of sulfur atom and/or at least one of oxygen atom as long as the ring has one sulfur atom. The ring is preferably a ring having 3 to 18 carbon atoms, and more preferably a ring having 4 to 18 carbon atoms.

Examples of the ring having a sulfur atom and formed by $R^{b9}$ and $R^{b10}$ bonded together include thiolane-1-ium ring (tetrahydrothiophenium ring), thian-1-ium ring and 1,4-oxathian-4-ium ring.

Examples of the ring having —CH—CO— and formed by $R^{b11}$ and $R^{b12}$ bonded together include oxocycloheptane ring, oxocyclohexane ring, oxonorbornane ring and oxoadamantane ring.

Among the cations represented by the formula (b2-1) to the formula (b2-4), the cation represented by the formula (b2-1-1) is preferable, and triphenyl sulfonium cation (v2=w2=x2=0 in the formula (b2-1-1)), diphenyl sulfonium cation (v2=w2=0, xz3=1, and $R^3$ is a methyl group in the formula (b2-1-1)), and tritolyl sulfonium cation (v1=w2=x3=1, $P^1$, $P^2$ and $P^3$ are a methyl group in the formula (b-2-1-1)) are more preferable.

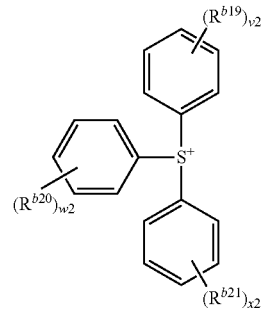

(b2-1-1)

wherein $R^{b19}$, $R^{b20}$ and $R^{b21}$ in each occurrence independently represent a halogen atom, a hydroxy group, a $C_1$ to $C_{12}$ alkyl group, a $C_3$ to $C_{18}$ alicyclic hydrocarbon group or a $C_1$ to $C_{12}$ alkoxy group, or two of $R^{b19}$, $R^{b20}$ and $R^{b21}$ may be bonded together to form a sulfur-containing ring;

v2 to x2 independently represent an integer of 0 to 5.

In the formula (b2-1-1), the sulfur-containing ring formed by two of $R^{b19}$, $R^{b20}$ and $R^{b21}$ may be either of monocyclic or polycyclic, aromatic or non-aromatic, or saturated or unsaturated ring, and may further have at least one of sulfur atom and/or at least one of oxygen atom as long as the ring has one sulfur atom.

$R^{b19}$ to $R^{b21}$ independently preferably represent a halogen atom (and more preferably fluorine atom), a hydroxy group, a $C_1$ to $C_{12}$ alkyl group or a $C_1$ to $C_{12}$ alkoxy group; or two of $R^{b19}$, $R^{b20}$ and $R^{b21}$ preferably are bonded together to form a sulfur-containing ring, and v2 to x2 independently represent preferably 0 or 1.

Specific examples of the organic cations represented by the formula (b2-1) to the formula (b2-4) include, for example, compounds described in JP2010-204646A.

The acid generator (III) is a compound combined the above sulfonate anion with an organic cation.

The above sulfonate anion and the organic cation may optionally be combined, a combination of any of the anion represented by the formula (III1-1-1) to the formula (III1-1-9) and the cation represented by the formula (b2-1-1), as well as a combination of any of the anion represented by the formula (III1-1-3) to the formula (III1-1-5) and the cation represented by the formula (b2-3) are preferable.

Preferred acid generators (III) are represented by the formula (III-1) to the formula (III-20). Among these, the formulae (III-1), (III-2), (III-6), (III-11), (III-12), (III-13) and (III-14) which contain triphenyl sulfonium cation, and the formulae (III-3) and (III-7) which contain tritolyl sulfonium cation are preferable.

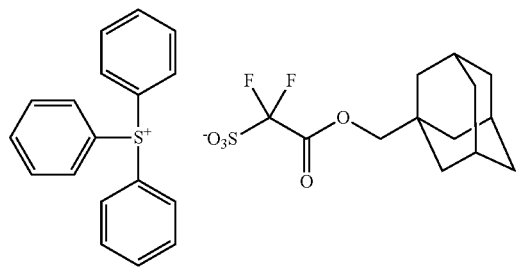

(III-1)

(III-2)

(III-3)

(III-4)

(III-5)

(III-6)

(III-7)

(III-8)

(III-9)

(III-10)
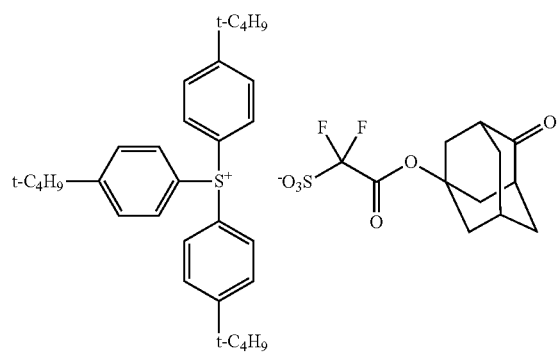
(III-11)
(III-12)
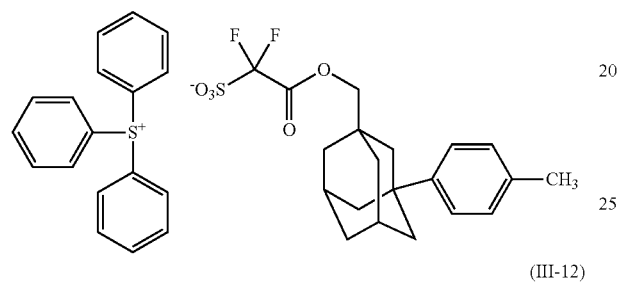
(III-13)
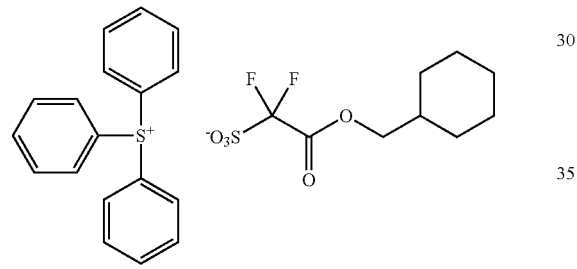
(III-14)
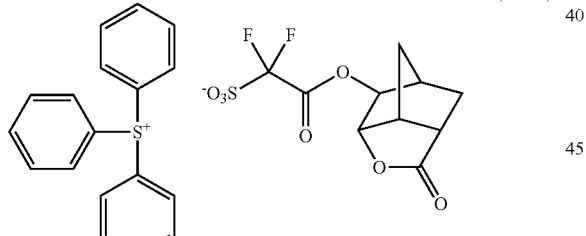
(III-15)
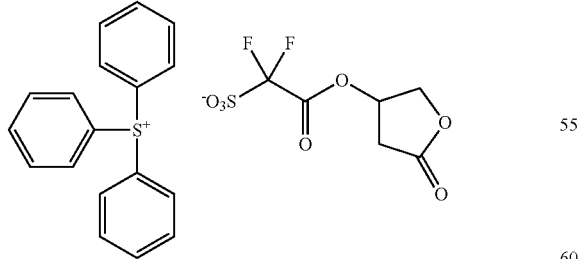
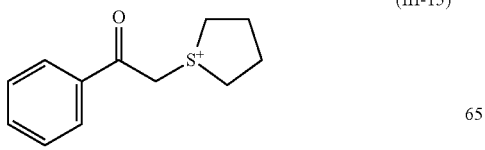
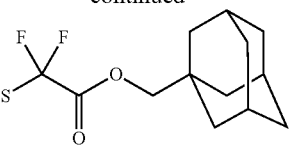
(III-16)
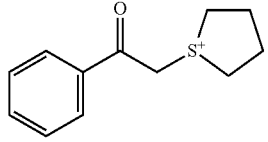
(III-17)
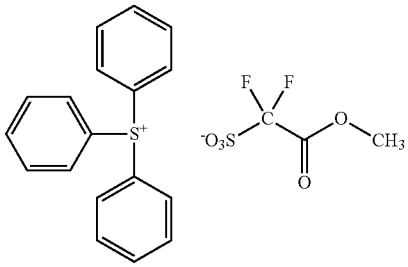
(III-18)
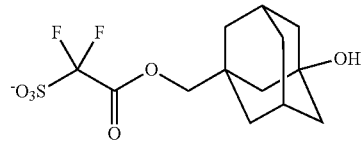
(III-19)
(III-20)
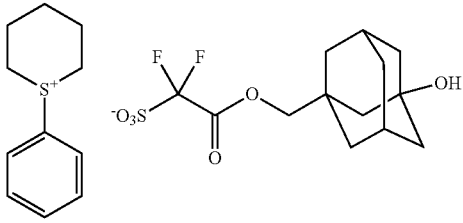
The acid generator (III) can be produced by a known method in this field.

In the resist composition of the present invention, the acid generator (III) may be used as a single salt or as a combination of two or more salts.

<Other Acid Generator>

The resist composition of the present invention contains at least one kinds of acid generator (II), or at least one kinds of acid generator (II) and at lest one kinds of acid generator (III), and may further include a known acid generator other than the acid generator (II) and the acid generator (III) (hereinafter is sometimes referred to as "acid generator (B)".

The acid generator (B) may be any of a non-ionic-based and an ionic-based acid generator, and ionic-based acid generator is preferable. Examples of the acid generator (B) include, an acid generator having a cation and an anion which are different from these of the acid generator (II) and the acid generator (III), an acid generator having a cation which is the same as these of the acid generator (II) and the acid generator (III) and an anion of a known anion which is different from that of the acid generator (II) and the acid generator (III), and an acid generator having an anion which is the same as these of the acid generator (II) and the acid generator (III) and a cation of a known anion which is different from that of the acid generator (II) and the acid generator (III).

In the resist composition of the present invention, the proportion of the acid generator (II) is preferably not less than 1 weight % (and more preferably not less than 3 weigh %), and not more than 30 weight % (and more preferably not more than 25 weight %), with respect to the resin (A).

The proportion of the acid generator (III) is preferably not less than 1 weight % (and more preferably not less than 3 weight %), and not more than 30 weight % (and more preferably not more than 25 weight %), with respect to the resin (A).

In this case, the weight ratio of the acid generator (II) and the acid generator (III) is preferably, for example, 5:95 to 95:5, more preferably 10:90 to 90:10 and still more preferably 15:85 to 85:15.

When the resist composition of the present invention contains the acid generator (B), the total proportion of the acid generator (II), the acid generator (III) and the acid generator (B) is preferably not less than 1 parts by weight (and more preferably not less than 3 weight %), and not more than 40 weight % (and more preferably not more than 35 weight %), with respect to the resin (A).

<Solvent (E)>

The resist composition of the present invention preferably includes a solvent (E). The proportion of the solvent (E) 90 weight % or more, preferably 92 weight % or more, and more preferably 94 weight % or more, and also preferably 99.9 weight % or less and more preferably 99 weight % or less. The proportion of the solvent (E) can be measured with a known analytical method such as, for example, liquid chromatography and gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; ethers such as diethylene glycol dimethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

<Basic Compound (C)>

The resist composition of the present invention may contain a basic compound (C). The basic compound (C) is a compound having a property to quench an acid, in particular, generated from the acid generator (B), and called "quencher".

As the basic compounds (C), nitrogen-containing basic compounds (for example, amine and basic ammonium salt) are preferable. The amine may be an aliphatic amine or an aromatic amine. The aliphatic amine includes any of a primary amine, secondary amine and tertiary amine. Preferred basic compounds (C) include compounds presented by the formula (C1) to the formula (C8) and the formula (C1-1) as described below. Among these, the basic compound presented by the formula (C1-1) is more preferable.

(C1)

wherein $R^{c1}$, $R^{c2}$ and $R^{c3}$ independently represent a hydrogen atom, a $C_1$ to $C_6$ alkyl group, $C_5$ to $C_{10}$ alicyclic hydrocarbon group or a $C_6$ to $C_{10}$ aromatic hydrocarbon group, one or more hydrogen atom contained in the alkyl group and alicyclic hydrocarbon group may be replaced by a hydroxy group, an amino group or a $C_1$ to $C_6$ alkoxyl group, one or more hydrogen atom contained in the aromatic hydrocarbon group may be replaced by a $C_1$ to $C_6$ alkyl group, a $C_1$ to $C_6$ alkoxyl group, a $C_5$ to $C_{10}$ alicyclic hydrocarbon group or a $C_6$ to $C_{10}$ aromatic hydrocarbon group.

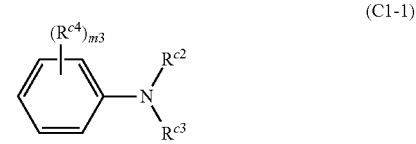

(C1-1)

wherein $R^{c2}$ and $R^{c3}$ have the same definition of the above;

$R^{c4}$ in each occurrence represents a $C_1$ to $C_6$ alkyl group, a $C_1$ to $C_6$ alkoxyl group, a $C_5$ to $C_{10}$ alicyclic hydrocarbon group or a $C_6$ to $C_{10}$ aromatic hydrocarbon group;

m3 represents an integer 0 to 3.

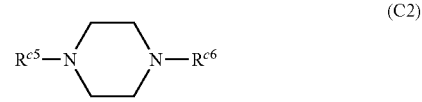

(C2)

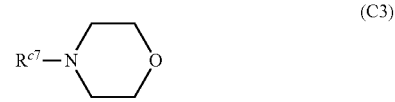

(C3)

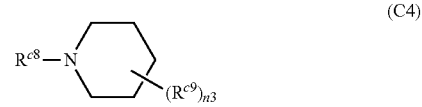

(C4)

wherein $R^{c5}$, $R^{c6}$, $R^{c7}$ and $R^{c8}$ independently represent the any of the group as described in $R^{c1}$ of the above;

$R^{c9}$ in each occurrence independently represents a $C_1$ to $C_6$ alkyl group, a $C_3$ to $C_6$ alicyclic hydrocarbon group or a $C_2$ to $C_6$ alkanoyl group;

n3 represents an integer of 0 to 8.

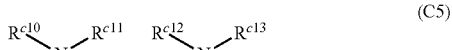

(C5)

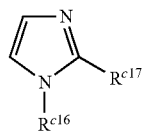

(C6)

wherein $R^{c10}$, $R^{c11}$, $R^{c12}$, $R^{c13}$ and $R^{c16}$ independently represent the any of the groups as described in $R^{c1}$;

$R^{c14}$, $R^{c15}$ and $R^{c17}$ in each occurrence independently represent the any of the groups as described in $R^{c4}$;

o3 and p3 represent an integer of 0 to 3;

$L^{c1}$ represents a divalent $C_1$ to $C_6$ alkanediyl group, —CO—, —C(=NH)—, —S— or a combination thereof.

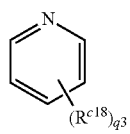

(C7)

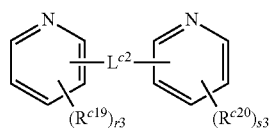

(C8)

wherein $R^{c18}$, $R^{c19}$ and $R^{c20}$ in each occurrence independently represent the any of the groups as described in $R^{c4}$;

q3, r3 and s3 represent an integer of 0 to 3;

$L^{c2}$ represents a single bond, a $C_1$ to $C_6$ alkanediyl group, —CO—, —C(=NH)—, —S— or a combination thereof.

In the formula (C1) to the formula (C8) and the formula (C1-1), the alkyl, alicyclic hydrocarbon, aromatic, alkoxy and alkanediyl groups include the same examples as the above.

Examples of the alkanoyl group include acetyl, 2-methyl acetyl, 2,2-dimethyl acetyl, propionyl, butyryl, isobutyryl, pentanoyl and 2,2-dimethyl propionyl groups.

Specific examples of the amine represented by the formula (C1) include 1-naphtylamine, 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylene diamine, tetramethylene diamine, hexamethylene diamine, 4,4'-diamino-1,2-diphenylethane, 4,4'-diamino-3,3'-dimethyldiphenylmethane and 4,4'-diamino-3,3'-diethyldiphenylmethane.

Among these, diisopropylaniline is preferable, particularly 2,6-diisopropylaniline is more preferable as the basic compounds (C) contained in the present resist composition.

Specific examples of the compound represented by the formula (C2) include, for example, piperazine.

Specific examples of the compound represented by the formula (C3) include, for example, morpholine.

Specific examples of the compound represented by the formula (C4) include, for example, piperidine, a hindered amine compound having piperidine skeleton described in JP H11-52575-A.

Specific examples of the compound represented by the formula (C5) include, for example, 2,2'-methylenebisaniline.

Specific examples of the compound represented by the formula (C6) include, for example, imidazole and 4-methylimidazole.

Specific examples of the compound represented by the formula (C7) include, for example, pyridine and 4-methylpyridine.

Specific examples of the compound represented by the formula (C8) include, for example, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

The proportion of the basic compound (C) is preferably 0.01 to weight %, more preferably 0.01 to 3 weight %, and still more preferably 0.01 to 1 weight % with respect to the total solid proportion of the resist composition.

<Other Ingredient (Hereinafter is Sometimes Referred to as "Other Ingredient (F)")>

The resist composition can also include small amounts of various known additives such as sensitizers, dissolution inhibitors, surfactants, stabilizers, and dyes, as needed.

<Preparing the Resist Composition>

The present resist composition can be prepared by mixing the resin (A1), the resin (A2) and the acid generator (B), and the basic compound (C), the solvent (E) and the other ingredient (F) as needed. There is no particular limitation on the order of mixing. The mixing may be performed in an arbitrary order. The temperature of mixing may be adjusted to an appropriate temperature within the range of to 40° C., depending on the kinds of the resin and solubility in the solvent (E) of the resin. The time of mixing may be adjusted to an appropriate time within the range of 0.5 to 24 hours, depending on the mixing temperature. There is no particular limitation to the tool for mixing. An agitation mixing may be adopted.

After mixing the above ingredients, the present resist compositions can be prepared by filtering the mixture through a filter having about 0.003 to 0.2 μm pore diameter.

<Method for Producing a Resist Pattern>

The method for producing a resist pattern of the present invention includes the steps of:

(1) applying the resist composition of the present invention onto a substrate;
(2) drying the applied composition to form a composition layer;
(3) exposing the composition layer;
(4) heating the exposed composition layer, and
(5) developing the heated composition layer.

Applying the resist composition onto the substrate can generally be carried out through the use of a resist application device, such as a spin coater known in the field of semiconductor microfabrication technique.

Drying the applied composition layer, for example, can be carried out using a heating device such as a hotplate (so-called "prebake"), a decompression device, or a combination thereof. Thus, the solvent evaporates from the resist composition and a composition layer with the solvent removed is formed. The condition of the heating device or the decompression device can be adjusted depending on the kinds of the solvent used. The temperature in this case is generally within the range of 50 to 200° C. Moreover, the pressure is generally within the range of 1 to $1.0 \times 10^5$ Pa.

The composition layer thus obtained is generally exposed using an exposure apparatus or a liquid immersion exposure apparatus. The exposure is generally carried out through a mask that corresponds to the desired pattern. Various types of exposure light source can be used, such as irradiation with ultraviolet lasers such as KrF excimer laser (wavelength: 248 nm), ArF excimer laser (wavelength: 193 nm), F2 excimer laser (wavelength: 157 nm), or irradiation with far-ultraviolet wavelength-converted laser light from a solid-state laser source (YAG or semiconductor laser or the like), or vacuum ultraviolet harmonic laser light or the like. Also, the exposure device may be one which irradiates electron beam or extreme-ultraviolet light (EUV).

After exposure, the composition layer is subjected to a heat treatment (so-called "post-exposure bake") to promote the deprotection reaction. The heat treatment can be carried out using a heating device such as a hotplate. The heating temperature is generally in the range of 50 to 200° C., preferably in the range of 70 to 150° C.

The composition layer is developed after the heat treatment, generally with an alkaline developing solution and using a developing apparatus. The development here means to bring the composition layer after the heat treatment into contact with an alkaline solution. Thus, the exposed portion of the composition layer is dissolved by the alkaline solution and removed, and the unexposed portion of the composition layer remains on the substrate, whereby producing a resist pattern. Here, as the alkaline developing solution, various types of aqueous alkaline solutions used in this field can be used. Examples include aqueous solutions of tetramethylammonium hydroxide and (2-hydroxyethyl)trimethylammonium hydroxide (common name: choline).

After the development, it is preferable to rinse the substrate and the pattern with ultrapure water and to remove any residual water thereon.

<Application>

The resist composition of the present invention is useful as the resist composition for excimer laser lithography such as with ArF, KrF or the like, and the resist composition for electron beam (EB) exposure lithography and extreme-ultraviolet (EUV) exposure lithography, as well as liquid immersion exposure lithography.

The resist composition of the present invention can be used in semiconductor microfabrication and in manufacture of liquid crystals, thermal print heads for circuit boards and the like, and furthermore in other photofabrication processes, which can be suitably used in a wide range of applications.

EXAMPLES

The present invention will be described more specifically by way of examples, which are not construed to limit the scope of the present invention.

All percentages and parts expressing the content or amounts used in the Examples and Comparative Examples are based on weight, unless otherwise specified.

The structure of a compound is measured by MASS (LC: manufactured by Agilent, 1100 type, MASS: manufactured by Agilent, LC/MSD type or LC/MSD TOF type).

The weight average molecular weight is a value determined by gel permeation chromatography.

Apparatus: HLC-8120GPCtype (Tosoh Co. Ltd.)
Column: TSK gel Multipore HXL-M×3+guardcolumn (Tosoh Co. Ltd.)
Eluant: tetrahydrofuran
Flow rate: 1.0 mL/min
Detecting device: RI detector
Column temperature: 40° C.
Injection amount: 100 μL
Standard material for calculating molecular weight: standard polystylene (Toso Co. ltd.)

Synthesis Example 1

Synthesis of Compound Represented by the Formula (A)

10.00 parts of a compound (A-2), 40.00 parts of tetrahydrofuran and 7.29 parts of pyridine were mixed, and stirred for 30 minutes at 23° C. The obtained mixture was cooled to 0° C. To this mixture was added 33.08 parts of a compound (A-1) over 1 hour while maintaining at the same temperature. The temperature of the mixture was then elevated to about 23° C., and the mixture was stirred for 3 hour at the same temperature. To thus obtained reactant was, 361.51 parts of ethyl acetate and 20.19 parts of 5% of hydrochloric acid solution were added to obtain a mixture, the mixture was stirred for 30 minutes at 23° C. The obtained solution was allowed to stand, and then separated to recover an organic layer. To the recovered organic layer, 81.42 parts of a saturated sodium hydrogen carbonate was added, and the obtained solution was stirred for 30 minutes at 23° C., allowed to stand, and then separated to recover the organic layer. To the recovered organic layer was added 90.38 parts of ion-exchanged water, and the obtained solution was stirred for 30 minutes at 23° C., allowed to stand, and then separated to wash the organic layer with water. These washing operations were repeated for 5 times. The obtained organic layer was concentrated, resulting in 23.40 parts of the compound (A).

MS (mass spectroscopy): 326.0 (molecular ion peak)

Synthesis Example 2

Synthesis of Compound Represented by the Formula (B)

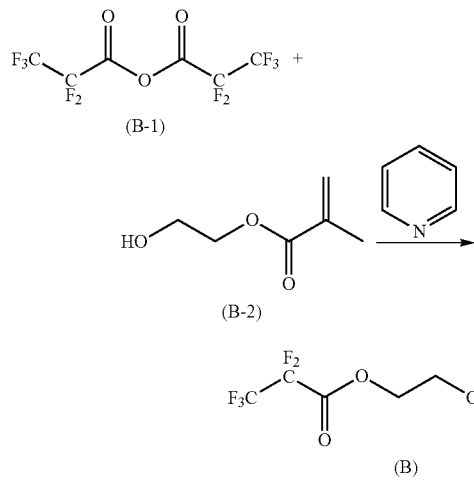

88.00 parts of a compound (B-2), 616.00 parts of methyl isobutyl ketone and 60.98 parts of pyridine were mixed, and stirred for 30 minutes at 23° C. The obtained mixture was cooled to 0° C. To this mixture was added 199.17 parts of a compound (B-1) over 1 hour while maintaining at the same temperature. The temperature of the mixture was then elevated to about 10° C., and the mixture was stirred for 1 hour at the same temperature. Thus obtained reactant was added to 1446.22 parts of n-heptane and 703.41 parts of 2% of hydrochloric acid solution to obtain a mixture, the mixture was stirred for 30 minutes at 23° C. The obtained solution was allowed to stand, and then separated to recover an organic layer. To the recovered organic layer, 337.64 parts of 2% of hydrochloric acid solution was added to obtain a mixture, and the mixture was stirred for 30 minutes at 23° C. The obtained solution was allowed to stand, and then separated to recover an organic layer. To the recovered organic layer, 361.56 parts of ion-exchanged water was added, and the obtained solution was stirred for 30 minutes at 23° C., allowed to stand, and then separated to wash the organic layer with water. To the obtained organic layer, 443.92 parts of 10% of potassium carbonate was added, and the obtained solution was stirred for 30 minutes at 23° C., allowed to stand, and then separated to recover the organic layer. These washing operations were repeated for 2 times. To the obtained organic layer, 361.56 parts of ion-exchanged water was added, and the obtained solution was stirred for 30 minutes at 23° C., allowed to stand, and then separated to wash the organic layer with water. These washing operations were repeated for 5 times. The obtained organic layer was concentrated, resulting in 163.65 parts of the compound (B).

MS (mass spectroscopy): 276.0 (molecular ion peak)

Synthesis Example 3

Synthesis of Compound Represented by the Formula (E)

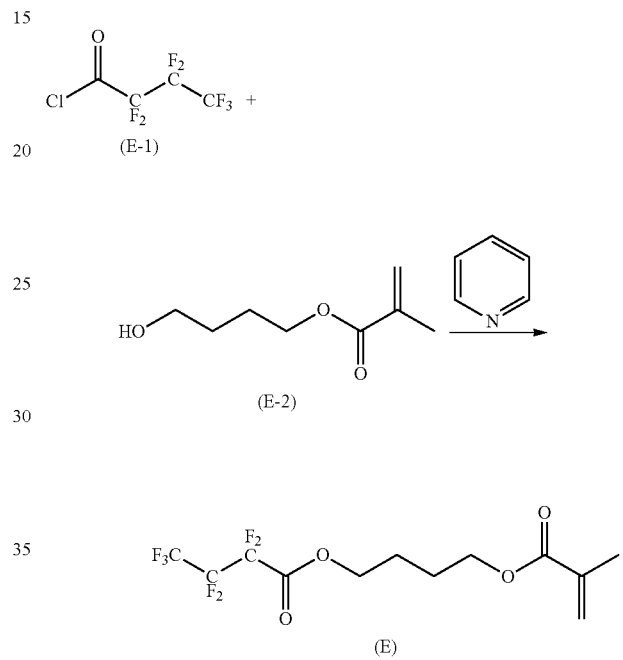

30.00 parts of a compound (E-2), 210.00 parts of methyl isobutyl ketone and 18.00 parts of pyridine were mixed, and stirred for 30 minutes at 23° C. The obtained mixture was cooled to 0° C. To this mixture was added 48.50 parts of a compound (E-1) over 1 hour while maintaining at the same temperature. The temperature of the mixture was then elevated to about 5° C., and the mixture was stirred for 1 hour at the same temperature. Thus obtained reactant was added to 630 parts of ethyl acetate, 99.68 parts of 5% of hydrochloric acid solution and 126 parts of ion-exchanged water to obtain a mixture, the mixture was stirred for 30 minutes at 23° C. The obtained solution was allowed to stand, and then separated to recover an organic layer. To the recovered organic layer, 86.50 parts of 10% of potassium carbonate solution was added to obtain a mixture, and the mixture was stirred for 30 minutes at 23° C. The obtained solution was allowed to stand, and then separated to recover an organic layer. These washing operations were repeated for two times. To the recovered organic layer, 157.50 parts of ion-exchanged water was added, and the obtained solution was stirred for 30 minutes at 23° C., allowed to stand, and then separated to wash the organic layer with water. These washing operations were repeated for five times. The obtained organic layer was concentrated, resulting in 27.61 parts of the compound (E).

MS (mass spectroscopy): 354.1 (molecular ion peak)

Synthesis Example 4

Synthesis of Compound Represented by the Formula (F)

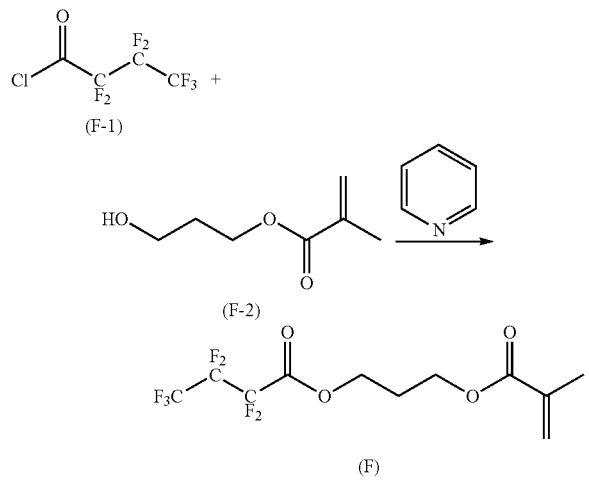

27.34 parts of a compound (F-2), 190.00 parts of methyl isobutyl ketone and 18.00 parts of pyridine were mixed, and stirred for 30 minutes at 23° C. The obtained mixture was cooled to 0° C. To this mixture was added 48.50 parts of a compound (F-1) over 1 hour while maintaining at the same temperature. The temperature of the mixture was then elevated to about 5° C., and the mixture was stirred for 1 hour at the same temperature. Thus obtained reactant was added to 570 parts of ethyl acetate, 99.68 parts of 5% of hydrochloric acid solution and 126 parts of ion-exchanged water to obtain a mixture, the mixture was stirred for 30 minutes at 23° C. The obtained solution was allowed to stand, and then separated to recover an organic layer. To the recovered organic layer, 86.50 parts of 10% of potassium carbonate solution was added to obtain a mixture, and the mixture was stirred for 30 minutes at 23° C. The obtained solution was allowed to stand, and then separated to recover an organic layer. These washing operations were repeated for two times. To the recovered organic layer, 150 parts of ion-exchanged water was added, and the obtained solution was stirred for 30 minutes at 23° C., allowed to stand, and then separated to wash the organic layer with water. These washing operations were repeated for five times. The obtained organic layer was concentrated, resulting in 23.89 parts of the compound (F).

MS (mass spectroscopy): 340.1 (molecular ion peak)

Synthesis Example 5

Synthesis of Compound Represented by the Formula (II-2)

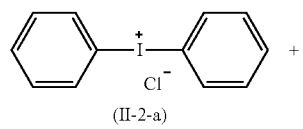

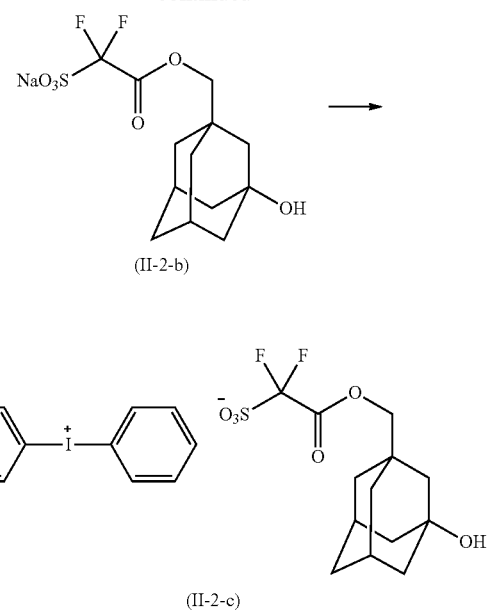

A compound represented by the formula (II-2-b) was synthesized according to the method described in JP 2008-209917A.

35.00 parts of the compound represented by the formula (II-2-b), 30.58 parts of the salt represented by the formula (II-2-a), 100 parts of chloroform and 50.00 parts of ion-exchanged water were charged, and stirred for 15 hours at 23° C. The obtained reacted solution was separated into two layers, and a chloroform layer was isolated. To the obtained chloroform layer, 30 parts of ion-exchanged water was added, stirred, and separated to wash an organic layer. These operations were repeated for five times. The obtained chloroform layer was concentrated to obtain a concentrate, to this concentrate, 100 parts of tert-butylmethyl ether was added, and the obtained mixture was stirred for 30 minutes at 23° C., and filtrated, resulting in 44.93 parts of the salt represented by the formula (II-2-c).

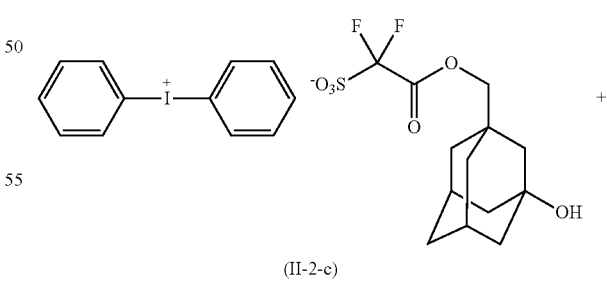

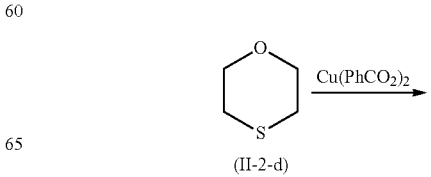

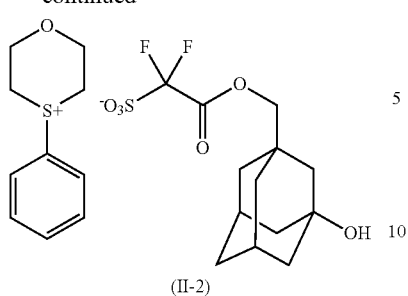

(II-2)

20.0 parts of the salt represented by the formula (II-2-c), 3.36 parts of the compound represented by the formula (II-2-d) and 100.00 parts of monochlorobenzene were charged, and stirred for 30 minutes at 23° C., 0.25 parts of cupper (II) dibenzoate was added thereto. The resultant was stirred for 1 hour at 100° C. to obtain the solution. The obtained reacted solution was concentrated. To the obtained residue, 200 parts of chloroform, 8 parts of acetonitrile and 50 parts of ion-exchanged water were added, stirred for 30 minutes at 23° C., and separated to obtain an organic layer. To the obtained organic layer, 50 parts of ion-exchanged water was added, stirred for minutes at 23° C., and separated to obtain an organic layer. These operations repeated for four times. The obtained organic layer was concentrated to obtain a concentrate, to this concentrate, 37 parts of acetonitrile was added to dissolve, and the obtained mixture was concentrated. To the obtained residue, 71.80 parts of tert-butyl methyl ether was added, stirred, and the supernatant was removed. To the obtained mass, acetonitrile was added to dissolve, and concentrated, resulting in 2.44 parts of the salt represented by the formula (II-2).

MS (ESI(+) Spectrum): M⁺ 181.1

MS (ESI(−) Spectrum): M⁻ 339.1

Synthesis Example 6

Synthesis of Compound Represented by the Formula (II-3)

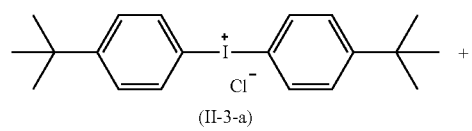

(II-3-a)

NaO₃S...

(II-3-b)

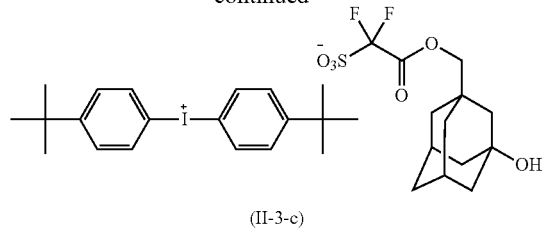

(II-3-c)

The compound represented by the formula (II-3-b) was synthesized according to the method described in JP 2008-209917A.

30.00 parts of the compound represented by the formula (II-3-b), 30.50 parts of the salt represented by the formula (II-3-a), 100 parts of chloroform and 50.00 parts of ion-exchanged water were charged, and stirred for 15 hours at 23° C. The obtained reacted solution was separated into two layers, and a chloroform layer was isolated. To the obtained chloroform layer, 30 parts of ion-exchanged water was added, stirred, and separated to wash an organic layer. These operations were repeated for five times. To the obtained chloroform layer was concentrated to obtain a concentrate, to this concentrate, 100 parts of tert-butylmethyl ether was added, and the obtained mixture was stirred for 30 minutes at 23° C., and filtrated, resulting in 48.57 parts of the salt represented by the formula (II-2-c).

(II-3-c)

(II-3-d) Cu(PhCO₂)₂ →

(II-3)

20.00 parts of the salt represented by the formula (II-3-c), 2.86 parts of the compound represented by the formula (II-3-d) and 250.00 parts of monochlorobenzene were charged, and stirred for 30 minutes at 23° C., 0.21 parts of cupper (II) dibenzoate was added thereto. The resultant was stirred for 1 hour at 100° C. to obtain the solution. The obtained reacted solution was concentrated. To the obtained residue, 200 parts of chloroform and 50 parts of ion-exchanged water were added, stirred for 30 minutes at 23° C., and separated to obtain an organic layer. To the obtained organic layer, 50 parts of ion-exchanged water were added, stirred for 30 minutes at 23° C., and separated to obtain an organic layer. These operations repeated for five times. The obtained organic layer was concentrated to obtain a concentrate, to this concentrate, 53.51 parts of acetonitrile was added to dissolve, and the obtained mixture was concentrated. To the obtained residue, 113.05 parts of tert-butyl methyl ether was added, stirred, and filtrated to obtain 10.47 parts of the salt represented by the formula (II-3).
MS (ESI(+) Spectrum): M⁺ 237.1
MS (ESI(−) Spectrum): M⁻ 339.1

Synthesis Example 7

Synthesis of Compound Represented by the Formula (III-5)

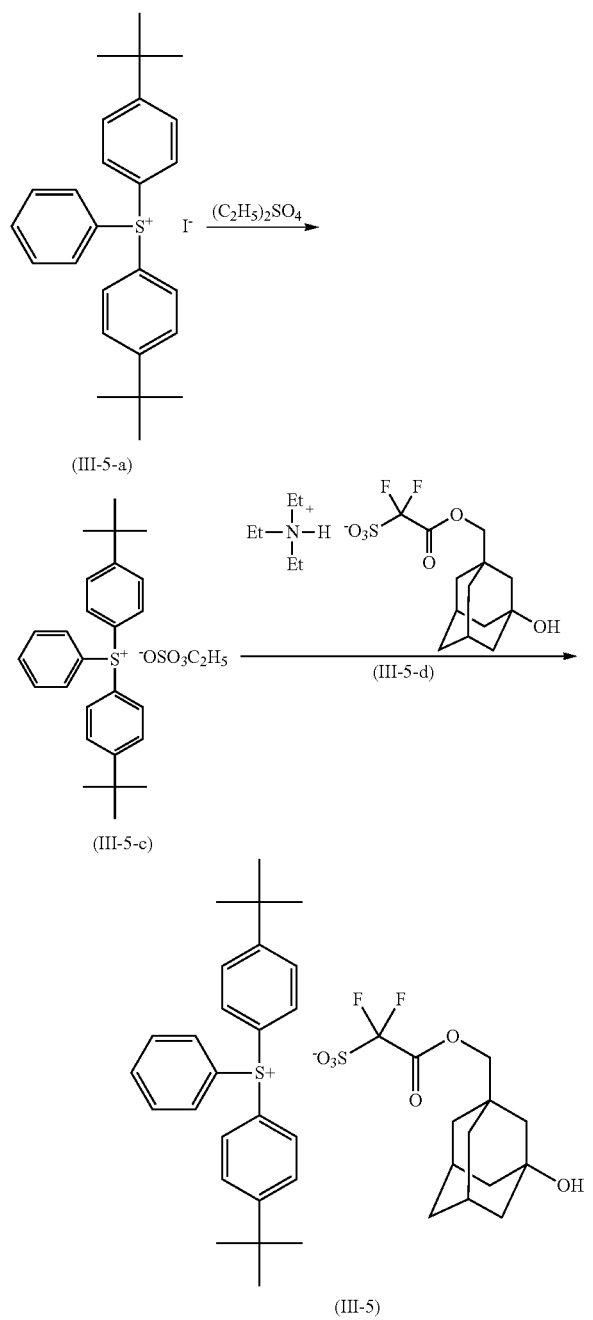

50.49 parts of the compound represented by the formula (III-5-a) and 252.4 parts of chloroform were charged, and stirred for minutes at 23° C. To the obtained reacted solution, 16.27 parts of the compound represented by the formula (III-5-b) was added in the form of drops, and stirred for 1 hour at 23° C. to obtain a solution containing the compound represented by the formula (III-5-c). To the solution, 48.80 parts of the salt represented by the formula (III-5-d) and 84.15 parts of the ion-exchanged water were added, stirred for 12 hours at 23° C. The obtained reacted solution was separated into two layers, and a chloroform layer was isolated. To the obtained chloroform layer, 84.15 parts of ion-exchanged water was added, stirred, and separated to wash an organic layer. These operations were repeated for five times. To the obtained chloroform layer, 3.88 parts of activated carbon was added, and the mixture was stirred and filtrated. The filtrate was concentrated to obtain a concentrate, to this concentrate, 125.87 parts of acetonitrile was added, and the obtained mixture was concentrated. To the obtained residue, 20.6 parts of acetonitrile and 309.30 parts of tert-butyl methyl ether were added, stirred for 30 minutes at 23° C. The supernatant was removed, the obtained solution was concentrated to obtain a concentrate, to this concentrate, 200 parts of n-heptane was added, and the obtained mixture was stirred for 30 minutes at 23° C., and filtrated, resulting in 61.54 parts of the salt represented by the formula (II-5).
MS (ESI(+) Spectrum): M⁺ 375.2
MS (ESI(−) Spectrum): M⁻ 339.1

Synthesis Example 8

Synthesis of Compound Represented by the Formula (III-19)

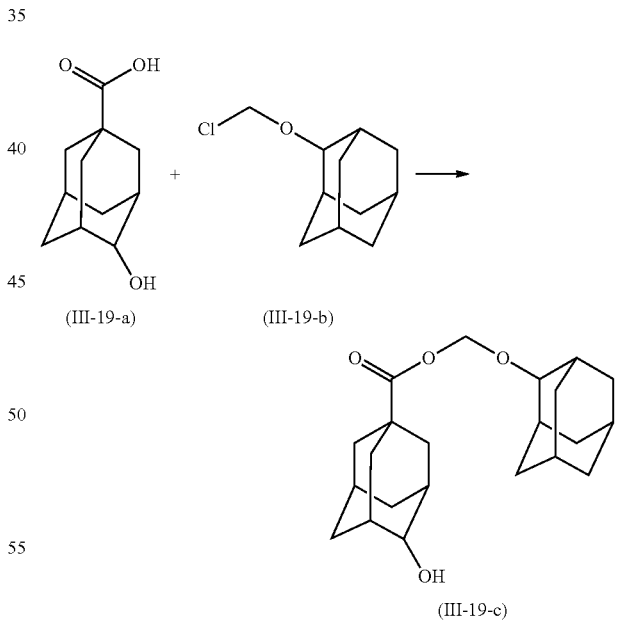

5.00 parts of the compound represented by the formula (III-19-a) and 25 parts of dimethylformamide were charged, and stirred for 30 minutes at 23° C. To the obtained reacted solution, 3.87 parts of trimethylamine was added in the form of drops, and stirred for 30 minutes at 23° C. to obtain a mixture. To the mixture, a solution dissolved 6.14 parts the salt represented by the formula (III-19-b) in 6.14 parts of dimethylformamide was added over 30 minutes, stirred for 2 hours at 23° C. To the obtained reacted solution, 25 parts of ion-exchanged water and 150 parts of ethyl acetate were added, the obtained mixture was stirred for 30 minutes at 23° C., and separated to obtain an organic layer. To the obtained organic layer, 75 parts of ion-exchanged water was added, the obtained mixture was stirred for 30 minutes at 23° C., and separated to obtain an organic layer. These washing operations repeated for five times. The obtained organic layer was concentrated to obtain a concentrate, to this concentrate, 92.20 parts of n-heptane was added, stirred, and filtrated, resulting in 2.69 parts of the salt represented by the formula (III-19-c).

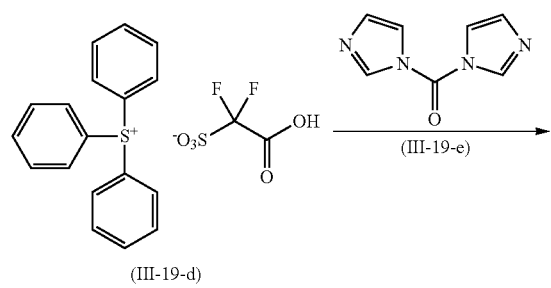

(III-19-d)                (III-19-e)

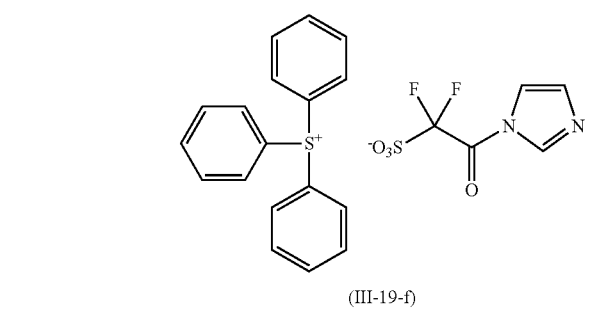

(III-19-f)

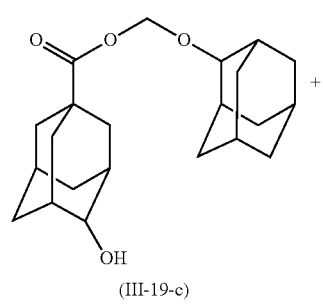

(III-19-c)

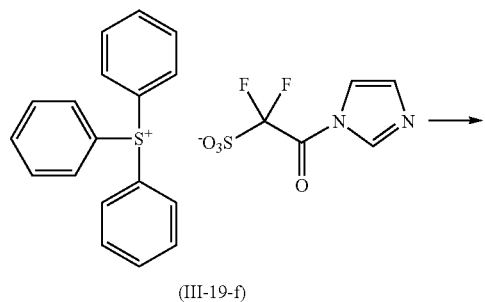

(III-19-f)

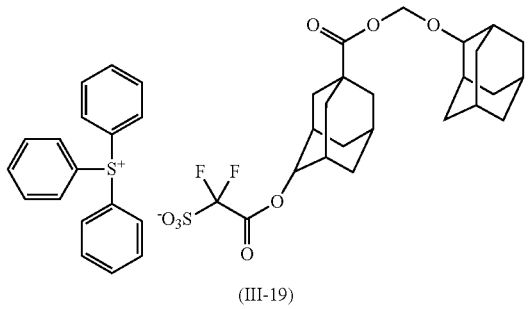

(III-19)

The compound representing by the formula (III-19-d) was synthesized according to the method described in JP 2008-127367A.

2.99 parts of the salt represented by the formula (III-19-d), 15.00 parts of acetonitrile were charged, and stirred for 30 minutes at 23° C. To the obtained reacted solution, 1.30 parts of the compound represented by the formula (III-19-e) was added, and stirred for 2 hours at 70° C. The obtained reactant was cooled to 23° C., and filtrated to obtain a solution containing the compound represented by the formula (III-19-f). To the obtained solution, a solution dissolved 2.12 parts of a compound (III-19-c) in 6.36 parts of chloroform was charged, stirred for 23 hours at 23° C. The obtained reactant was concentrated to obtain concentrate, to this concentrate, 60 parts of chloroform and 30 parts of 2% oxalic acid solution were charged, stirred, and then separated to recover an organic layer. These washing operations were repeated for two times. To the recovered organic layer, 30 parts of ion-exchanged water was added, and the obtained solution was stirred, and then separated to wash the organic layer with water. These washing operations were repeated for five times. The obtained organic layer was concentrated, to this concentrate, 30 parts of acetonitrile was added to dissolve, and concentrated. To this concentrate, 50 parts of tert-butylmethyl ether was added, stirred, and the supernatant was removed. The obtained residue was dissolved in acetonitrile, and the obtained solution was concentrated, resulting in 3.46 parts of the salt represented by the formula (III-19).

MS (ESI(+) Spectrum): M$^+$ 263.1

MS (ESI(−) Spectrum): M$^-$ 517.2

Synthetic Example of the Resin

The monomers used the synthesis of the resin are shown below.

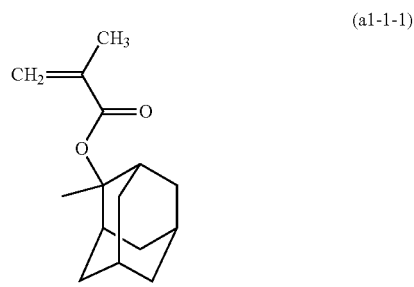

(a1-1-1)

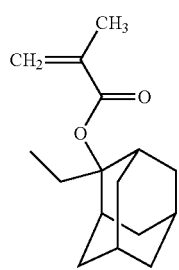 (a1-1-2)
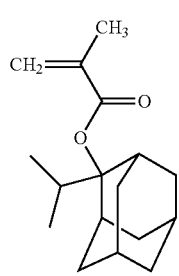 (a1-1-3)
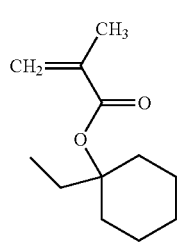 (a1-2-3)
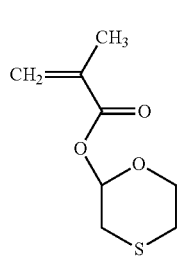 (a1-5-1)
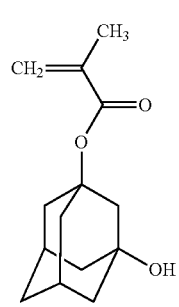 (a2-1-1)
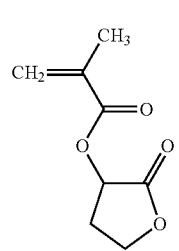 (a3-1-1)
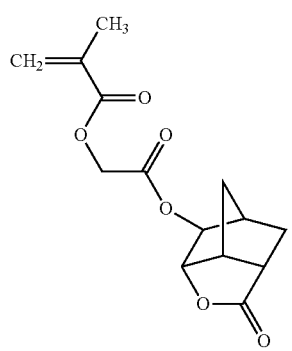 (a3-2-3)
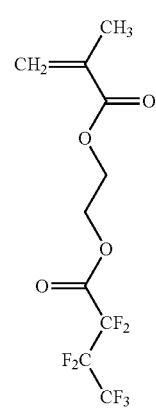 (A)
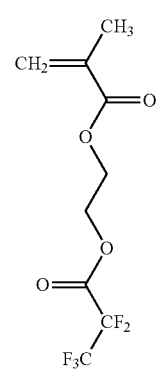 (B)
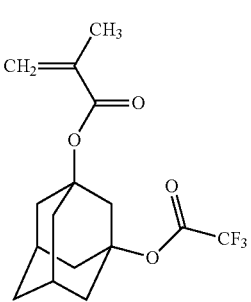 (C)

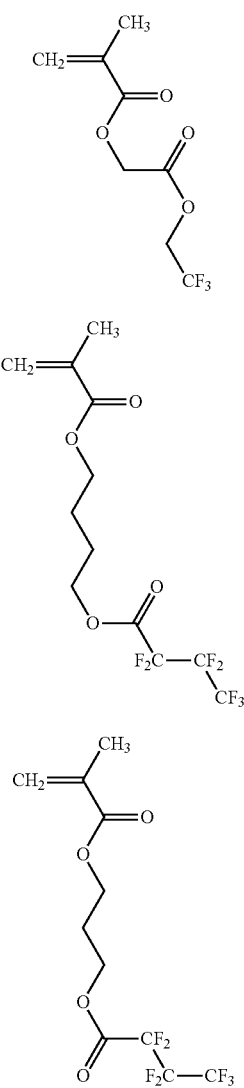

These monomers are referred to as "monomer (a1-1-1)" to "monomer (F)".

Synthetic Example 9

Synthesis of Resin A1-1

Monomer (B) was used, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 0.7 mol % and 2.1 mol % respectively with respect to the entire amount of monomers, and the resultant mixture was heated for about 5 hours at 75° C. After that, the obtained reacted mixture was poured into a large amount of methanol/water mixed solvent to precipitate a resin. Thus obtained resin was dissolved in another dioxane to obtain a solution, and the solution was poured into a mixture of methanol/water mixed solvent to precipitate a resin. The obtained resin was filtrated. These operations were repeated for two times, resulting in a 77% yield of polymer having a weight average molecular weight of about 18000. This polymer, which had the structural units of the following formula, was referred to Resin A1-1.

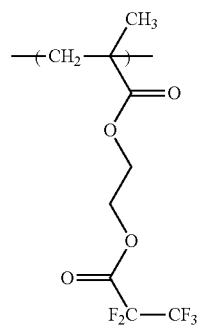

Synthetic Example 10

Synthesis of Resin A1-2

Monomer (A) and monomer (C) were mixed together with a mole ratio of Monomer (A): monomer (C)=90:10, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1 mol % and 3 mol % respectively with respect to the entire amount of monomers, and the resultant mixture was heated for about 5 hours at 72° C. After that, the obtained reacted mixture was poured into a large amount of n-heptane to precipitate a resin. The obtained resin was filtrated, resulting in a 70% yield of copolymer having a weight average molecular weight of about 13000. This copolymer, which had the structural units of the following formula, was referred to Resin A1-2.

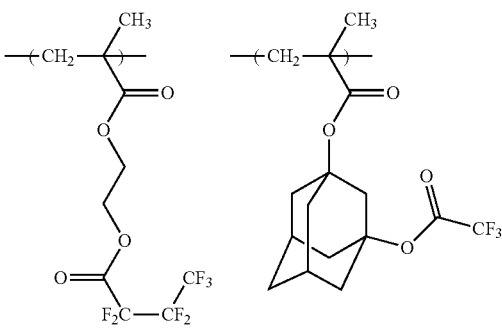

Synthetic Example 11

Synthesis of Resin A1-3

Monomer (E) was used, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 0.7 mol % and 2.1 mol % respectively with respect to the entire amount of monomers, and the resultant mixture was heated for about 5 hours at 75° C. After that, the obtained reacted mixture was poured into a large amount of methanol/water mixed solvent to precipitate a resin. Thus obtained resin was dissolved in another dioxane to obtain a solution, and the solution was poured into a mixture of methanol/water mixed solvent to precipitate a resin.

The obtained resin was filtrated. These operations were repeated for two times, resulting in a 73% yield of copolymer having a weight average molecular weight of about 19000. This copolymer, which had the structural units of the following formula, was referred to Resin A1-3.

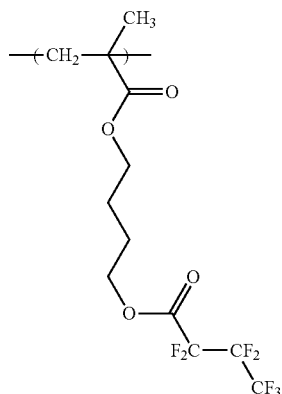

Synthetic Example 12

Synthesis of Resin A1-4

Monomer (F) was used, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 0.7 mol % and 2.1 mol % respectively with respect to the entire amount of monomers, and the resultant mixture was heated for about 5 hours at 75° C. After that, the obtained reacted mixture was poured into a large amount of methanol/water mixed solvent to precipitate a resin. Thus obtained resin was dissolved in another dioxane to obtain a solution, and the solution was poured into a mixture of methanol/water mixed solvent to precipitate a resin. The obtained resin was filtrated. These operations were repeated for two times, resulting in a 76% yield of polymer having a weight average molecular weight of about 18000. This polymer, which had the structural units of the following formula, was referred to Resin A1-4.

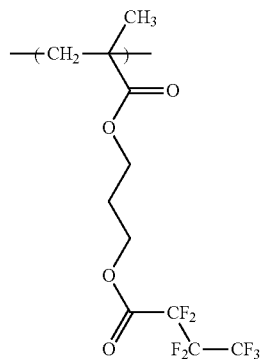

Synthetic Example 13

Synthesis of Resin A2-1

Monomer (a1-1-3), monomer (a1-2-3), monomer (a2-1-1), monomer (a3-1-1) and monomer (a3-2-3) were charged with molar ratio 30:14:6:20:30, and dioxane was added thereto in an amount equal to 1.5 weight times of the total amount of monomers to obtain a solution. Azobisisobutyronitrile and azobis(2,4-dimethylvaleronitrile) was added as an initiator thereto in an amount of 1 mol % and 3 mol % respectively with respect to the entire amount of monomers, and the resultant mixture was heated for about 5 hours at 73° C. After that, the reaction solution was poured into a mixture of methanol and ion-exchanged water (4:1) in large amounts to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times for purification, resulting in 65% yield of copolymer having a weight average molecular weight of about 8100. This copolymer, which had the structural units derived from the monomers of the following formula, was designated Resin A2-1.

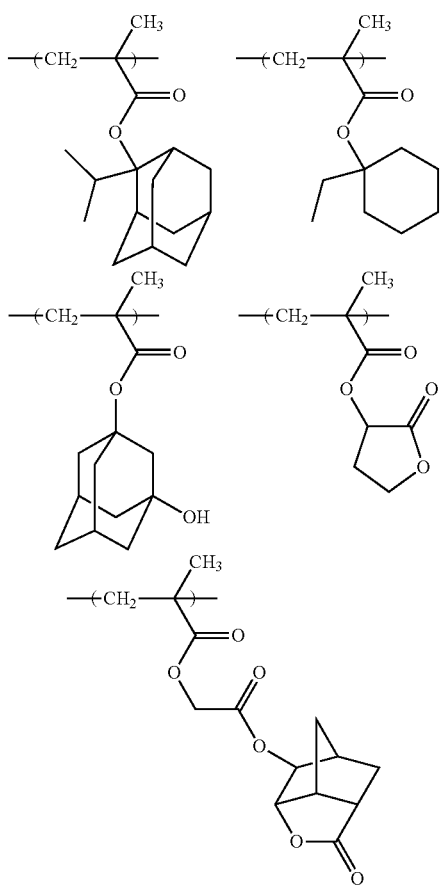

Synthetic Example 14

Synthesis of Resin A2-2

Monomer (a1-1-2), monomer (a1-2-3), monomer (a2-1-1), monomer (a3-1-1) and monomer (a3-2-3) were charged with molar ratio 30:14:6:20:30, and dioxane was added thereto in an amount equal to 1.5 weight times of the total amount of monomers to obtain a solution. Azobisisobutyronitrile and azobis(2,4-dimethylvaleronitrile) was added as an initiator thereto in an amount of 1 mol % and 3 mol % respectively with respect to the entire amount of monomers, and the resultant mixture was heated for about 5 hours at 73° C. After that, the reaction solution was poured into a mixture of methanol and ion-exchanged water (4:1) in large amounts to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times for purification, resulting in 68% yield of copolymer having a weight average molecular weight of about 7800. This copolymer, which had the structural units derived from the monomers of the following formula, was designated Resin A2-2.

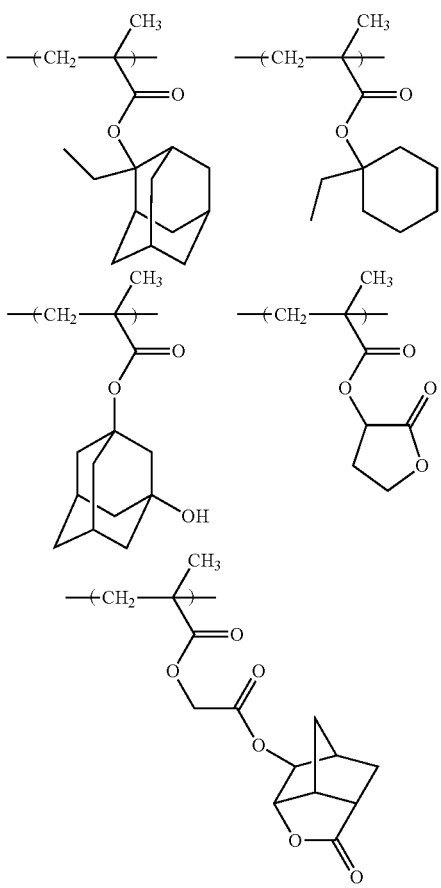

Synthetic Example 15

Synthesis of Resin A2-3

Monomer (a1-1-2), monomer (a2-1-1) and monomer (a3-1-1) were mixed with molar ratio 50:25:25, and dioxane was added thereto in an amount equal to 1.5 weight times of the total amount of monomers. Azobisisobutyronitrile and azobis (2,4-dimethyl valeronitrile) was added as an initiator thereto in an amount of 1 mol % and 3 mol % respectively with respect to the entire amount of monomers, and the resultant mixture was heated for about 8 hours at 80° C. After that, the reaction solution was poured into a mixture of methanol and ion-exchanged water (4:1) in large amounts to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated three times for purification, resulting in 60% yield of copolymer having a weight average molecular weight of about 9200. This copolymer, which had the structural units derived from the monomers of the following formulae, was designated Resin A2-3.

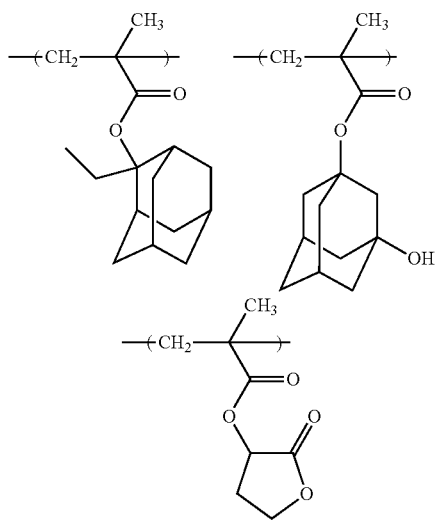

Synthetic Example 16

Synthesis of Resin A2-4

Monomer (a1-1-3), monomer (a1-2-3), monomer (a2-1-1), monomer (a3-2-3) and monomer (a3-1-1) were charged with molar ratio 30:14:6:20:30, and dioxane was added thereto in an amount equal to 1.5 weight times of the total amount of monomers to obtain a solution. Azobisisobutyronitrile and azobis(2,4-dimethylvaleronitrile) was added as an initiator thereto in an amount of 1 mol % and 3 mol % respectively with respect to the entire amount of monomers, and the resultant mixture was heated for about 5 hours at 75° C. After that, the reaction solution was poured into a mixture of methanol and ion-exchanged water (4:1) in large amounts to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times for purification, resulting in 60% yield of copolymer having a weight average molecular weight of about 7000. This copolymer, which had the structural units derived from the monomers of the following formula, was designated Resin A2-4.

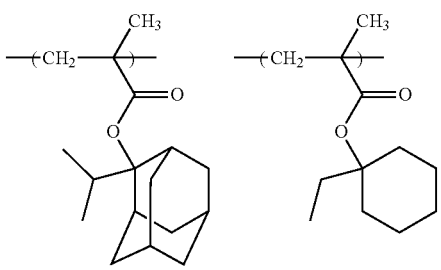

-continued

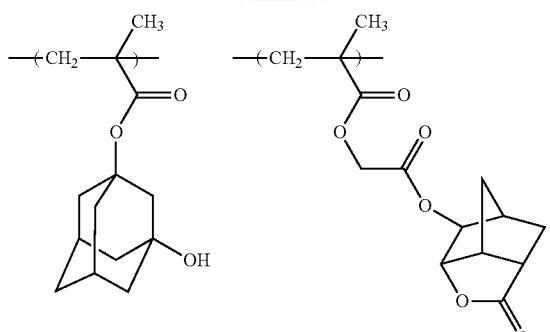

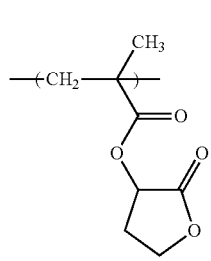

Synthetic Example 17

Synthesis of Resin A2-5

Monomer (a1-1-3), monomer (a1-5-1), monomer (a2-1-1), monomer (a3-2-3) and monomer (a3-1-1) were charged with molar ratio 30:14:6:20:30, and dioxane was added thereto in an amount equal to 1.5 weight times of the total amount of monomers to obtain a solution. Azobisisobutyronitrile and azobis(2,4-dimethylvaleronitrile) was added as an initiator thereto in an amount of 1 mol % and 3 mol % respectively with respect to the entire amount of monomers, and the resultant mixture was heated for about 5 hours at 75° C. After that, the reaction solution was poured into a mixture of methanol and ion-exchanged water in large amounts to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times for purification, resulting in 62% yield of copolymer having a weight average molecular weight of about 7400. This copolymer, which had the structural units derived from the monomers of the following formula, was designated Resin A2-5.

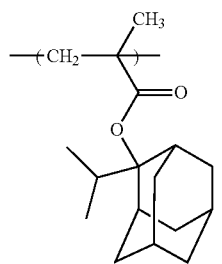 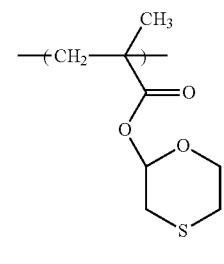

-continued

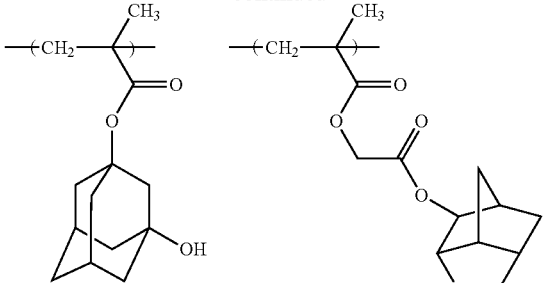

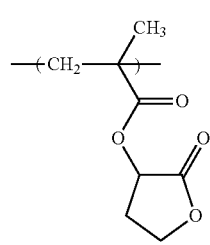

Synthetic Example 18

Synthesis of Resin X1

Monomer (a1-1-1), monomer (a3-1-1) and monomer (a2-1-1) were mixed with molar ratio 35:45:20, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1.0 mol % and 3.0 mol % respectively with respect to the entire amount of monomers, and the resultant mixture was heated for about 5 hours at 75° C. After that, the obtained reacted mixture was poured into a mixture of a large amount of methanol and water to precipitate a resin. The obtained resin was filtrated. Thus obtained resin was dissolved in another dioxane to obtain a solution, and the solution was poured into a mixture of methanol and water to precipitate a resin. The obtained resin was filtrated. These operations were repeated 2 times for purification, resulting in a 75% yield of copolymer having a weight average molecular weight of about 7000. This copolymer, which had the structural units of the following formula, was referred to Resin X1.

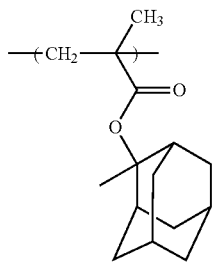 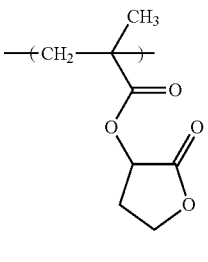

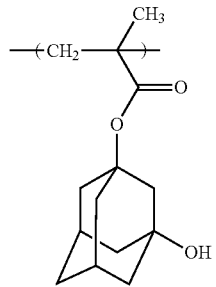

Synthetic Example 16

Synthesis of Resin X2

Monomer (D) and monomer (a1-1-1) were mixed with molar ratio=80:20, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 0.5 mol % and 1.5 mol % respectively with respect to the entire amount of monomers, and the resultant mixture was heated for about 5 hours at 70° C. After that, the obtained reacted mixture was poured into a mixture of a large amount of methanol and water to precipitate a resin. The obtained resin was filtrated. Thus obtained resin was dissolved in another dioxane to obtain a solution, and the solution was poured into a mixture of methanol and ion-exchanged water to precipitate a resin. The obtained resin was filtrated. These operations were repeated 2 times, resulting in a 70% yield of copolymer having a weight average molecular weight of about 28000. This copolymer, which had the structural units of the following formula, was referred to Resin X2.

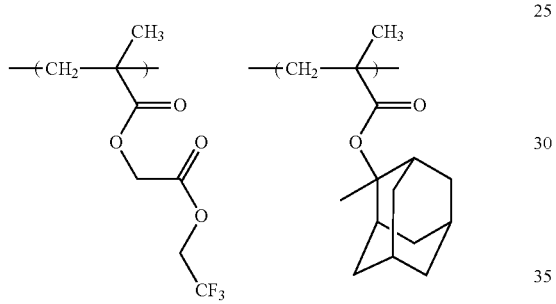

(Preparing Resist Composition)

Resist compositions were prepared by mixing and dissolving each of the components shown in Table 2, and then filtrating through a fluororesin filter having 0.2 μm pore diameter.

<Resin>

Resins Prepared by the Synthetic Examples

<Acid Generator>

B1: this was prepared by a method according to the method described in the Examples of JP2010-152341A B2: this was prepared by a method according to the method described in the Examples of WO2008/99869 and JP2010-26478A

TABLE 2

(Unit: parts)

| | Resin | Acid Generator | Basic Compound | BP/PEB (° C.) |
|---|---|---|---|---|
| Ex. | | | | |
| 1 | A1-1/A2-1 = 0.7/10 | II-2/III-3 = 0.80/0.70 | C1 = 0.07 | 95/85 |
| 2 | A1-1/A2-2 = 0.7/10 | II-2/III-3 = 0.80/0.70 | C1 = 0.07 | 110/105 |
| 3 | A1-1/A2-3 = 0.7/10 | II-2/III-3 = 0.80/0.70 | C1 = 0.07 | 110/105 |
| 4 | A1-2/A2-1 = 0.7/10 | II-2/III-3 = 0.80/0.70 | C1 = 0.07 | 95/85 |
| 5 | A1-2/A2-2 = 0.7/10 | II-2/III-3 = 0.80/0.70 | C1 = 0.07 | 110/105 |
| 6 | A1-2/A2-3 = 0.7/10 | II-2/III-3 = 0.80/0.70 | C1 = 0.07 | 110/105 |
| 7 | A1-2/A2-1 = 0.7/10 | II-3/III-3 = 0.80/0.70 | C1 = 0.07 | 95/85 |
| 8 | A1-2/A2-2 = 0.7/10 | II-3/III-3 = 0.80/0.70 | C1 = 0.07 | 110/105 |
| 9 | A1-2/A2-3 = 0.7/10 | II-3/III-3 = 0.80/0.70 | C1 = 0.07 | 110/105 |
| 10 | A1-2/X1 = 0.3/10 | II-2/B1 = 0.1/1.0 | C1 = 0.07 | 110/105 |
| 11 | A1-1/A2-4 = 0.7/10 | II-3/III-3 = 0.80/0.70 | C1 = 0.07 | 95/85 |
| 12 | A1-1/A2-5 = 0.7/10 | II-3/III-3 = 0.80/0.70 | C1 = 0.07 | 95/85 |
| 13 | A1-3/A2-5 = 0.7/10 | II-3/III-3 = 0.80/0.70 | C1 = 0.07 | 95/85 |
| 14 | A1-4/A2-5 = 0.7/10 | II-3/III-3 = 0.80/0.70 | C1 = 0.07 | 95/85 |
| 15 | A1-1/A2-5 = 0.7/10 | II-3/III-5 = 0.80/0.70 | C1 = 0.07 | 95/85 |
| 16 | A1-1/A2-5 = 0.7/10 | II-3/III-19 = 0.80/0.70 | C1 = 0.07 | 95/85 |
| Comparative Ex. | | | | |
| 1 | X2/X1 = 0.3/10 | B1/B2 = 1.0/0.1 | C1 = 0.07 | 110/105 |

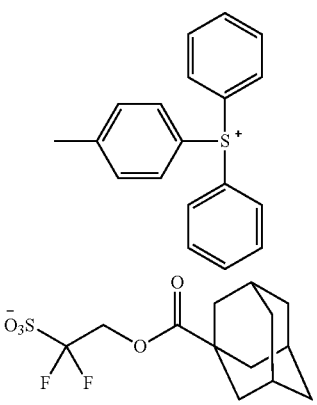

B3: this was prepared by a method according to the method described in the Examples of JP2005-221721A

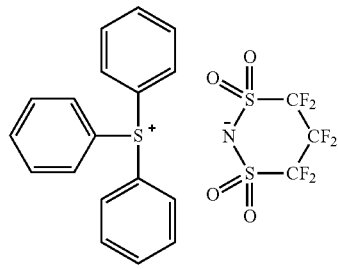 [SMILES: c1ccc([S+](c2ccccc2)c2ccccc2)cc1 ; O=S1(=O)[N-]S(=O)(=O)C(F)(F)C(F)(F)C1(F)F]

<Basic Compound: Qencher>

C1: 2,6-diisopropylaniline (obtained from Tokyo Chemical Industry Co., LTD)

<Solvent of Resist composition>

| | |
|---|---|
| Propylene glycol monomethyl ether acetate | 265 parts |
| Propylene glycol monomethyl ether | 20 parts |
| 2-Heptanone | 20 parts |
| γ-butyrolactone | 3.5 parts |

(Producing Resist Pattern)

A composition for an organic antireflective film ("ARC-29", by Nissan Chemical Co. Ltd.) was applied onto 12-inch silicon wafers and baked for 60 seconds at 205° C. to form a 78 nm thick organic antireflective film.

The above resist compositions were then applied thereon by spin coating so that the thickness of the resulting film became 85 nm after drying.

The obtained wafers were then pre-baked for 60 sec on a direct hot plate at the temperatures given in the "PB" column in Table 2 to obtain a composition layer.

Contact hole patterns were then exposed using a mask pattern (hole pitch: 100 nm, hole diameter: 70 nm) through stepwise changes in exposure quantity using an ArF excimer laser stepper for immersion lithography ("XT:1900Gi" by ASML Ltd.: NA=1.35, 3/42 annular X-Y polarization), on the wafers on which the composition layer had thus been formed. The ultrapure water was used for medium of immersion.

After the exposure, post-exposure baking was carried out by 60 seconds at the temperatures given in the "PEB" column in Table 2.

Then, puddle development was carried out with 2.38 wt % tetramethylammonium hydroxide aqueous solution for 60 seconds to obtain a resist pattern.

Each resist pattern was produced based on the resist composition using the mask pattern (hole pitch: 100 nm, hole diameter: 70 nm) as described above. The exposure amount at which a 55 nm-hole diameter was achieved in the pattern was defined as the effective sensitivity.

(Critical Dimension Uniformity (CDU) Evaluation)

The resist patterns were formed by the same method described above using the musk of 70 nm of hole diameter with the effective sensitivity. The hole diameter was measured 24 times per one hole, and an average of those was an average hole diameter. The standard deviation was obtained from the average hole diameter based on the population which was 400 values of the above average hole diameter within the same wafer.

A "○○" was given when the standard deviation was less than 1.55 nm, a "○" was given when the standard deviation was 1.55 nm or more and less than 2.00 nm, and an "x" was given when the standard deviation was 2.00 nm or more.

A Scanning Electron Microscope (CD SEM Hitachi CG-4000) was used for CDU evaluation.

Table 3 illustrates the results thereof. The parenthetical number means the standard deviation (nm).

(Evaluation of Defects)

The above resist compositions were applied on each of the 12-inch-silicon wafers by spin coating so that the thickness of the resulting film became 150 nm after drying.

The obtained wafers were then pre-baked for 60 seconds on a direct hot plate at the temperatures given in the "PB" column in Table 2 to obtain a composition layer.

The thus obtained wafers with the produced composition layers were rinsed with water for 60 seconds using a developing apparatus (ACT-12, Tokyo electron Co. Ltd.).

Thereafter, the number of defects was counted using a defect inspection apparatus (KLA-2360, KLA-Tencor Co. Ltd.)

Table 3 illustrates the results thereof.

TABLE 3

| Ex. | CDU | Defects |
|---|---|---|
| 1 | ○○ (1.34) | 230 |
| 2 | ○○ (1.48) | 240 |
| 3 | ○ (1.68) | 290 |
| 4 | ○○ (1.31) | 220 |
| 5 | ○○ (1.43) | 260 |
| 6 | ○ (1.58) | 330 |
| 7 | ○○ (1.42) | 200 |
| 8 | ○○ (1.49) | 240 |
| 9 | ○ (1.63) | 290 |
| 10 | ○ (1.84) | 480 |
| 11 | ○○ (1.29) | 200 |
| 12 | ○○ (1.26) | 180 |
| 13 | ○○ (1.41) | 130 |
| 14 | ○○ (1.39) | 160 |
| 15 | ○○ (1.23) | 150 |
| 16 | ○○ (1.24) | 160 |
| Comp. Ex. 1 | x (2.28) | 720 |

According to the resist composition of the present invention, it is possible to produce a resist pattern with excellent CDU and with few defects when producing the resist pattern. Therefore, the present resist composition can be used for semiconductor microfabrication.

What is claimed is:

1. A resist composition comprising
a resin having a structural unit represented by the formula (I),
a resin being insoluble or poorly soluble in alkali aqueous solution, but becoming soluble in an alkali aqueous solution by the action of an acid and not including the structural unit represented by the formula (I), and
an acid generator represented by the formula (II),

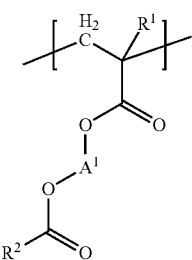

wherein $R^1$ represents a hydrogen atom or a methyl group;
$A^1$ represents a $C_1$ to $C_6$ alkanediyl group;
$R^2$ represents a $C_1$ to $C_6$ fluorinated alkyl group;

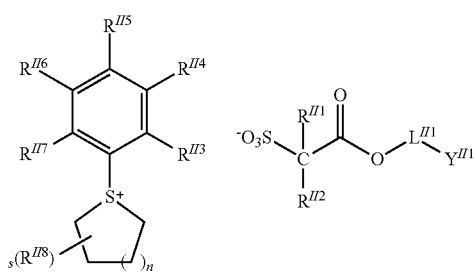

wherein $R^{II1}$ and $R^{II2}$ independently represent a fluorine atom or a $C_1$ to $C_6$ perfluoroalkyl group;
$L^{II1}$ represents a single bond, a $C_1$ to $C_6$ alkanediyl, a $C_4$ to $C_8$ divalent alicyclic hydrocarbon group, $-(CH_2)_t-CO-O-*$ or $-(CH_2)_t-CO-O-CH_2-(CH_2)_u-*$, one or more $-CH_2-$ contained in the alkanediyl, $-(CH_2)_t-CO-O-*$ or $-(CH_2)_t-CO-O-CH_2-(CH_2)_u-*$ may be replaced by $-O-$, t represents an integer of 1 to 12, u represents an integer of 0 to 12, * represents a bond to $Y^{II1}$;
$Y^{II1}$ represents an optionally substituted $C_3$ to $C_{18}$ alicyclic hydrocarbon group, and one or more $-CH_2-$ contained in the alicyclic hydrocarbon group may be replaced by $-O-$, $-CO-$ or $-SO_2-$;
$R^{II3}$, $R^{II4}$, $R^{II5}$, $R^{II6}$ and $R^{II7}$ independently represent a hydrogen atom, a hydroxy group, a $C_1$ to $C_6$ alkyl group, a $C_1$ to $C_6$ alkoxy group, a $C_2$ to $C_7$ alkoxycarbonyl group or a $C_2$ to $C_{12}$ acyloxy group,
one or more $-CH_2-$ contained in sulfur-containing ring of cation may be replaced by $-O-$ or $-CO-$;
n represents an integer of 1 to 3;
s represents an integer of 0 to 3; and
$R^{II8}$ in each occurrence independently represent a $C_1$ to $C_6$ alkyl group.

2. The resist composition according to claim 1, which further comprises an acid generator represented by the formula (III);

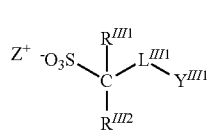

wherein $R^{III1}$ and $R^{III2}$ independently represent a fluorine atom or a $C_1$ to $C_6$ perfluoroalkyl group;
$L^{III1}$ represents a single bond or a $C_1$ to $C_{17}$ divalent saturated hydrocarbon group, one or more hydrogen atom in the saturated hydrocarbon group may be replaced by a fluorine atom or a hydroxy group, and one or more $-CH_2-$ contained in the saturated hydrocarbon group may be replaced by $-O-$ or $-CO-$;
$Y^{III1}$ represents an optionally substituted $C_1$ to $C_{18}$ alkyl group or an optionally substituted $C_3$ to $C_{18}$ alicyclic hydrocarbon group, and one or more $-CH_2-$ contained in the alkyl group and alicyclic hydrocarbon group may be replaced by $-O-$, $-CO-$ or $-SO_2-$; and
$Z^+$ represents an organic cation.

3. The resist composition according to claim 2, wherein $Z^+$ in the formula (III) is a triaryl sulfonium cation.

4. The resist composition according to claim 1, wherein $A^1$ in the formula (I) is an ethylene group.

5. The resist composition according to claim 1, wherein $L^{II1}$ in the formula (II) is a bond or methylene group.

6. The resist composition according to claim 1, which further comprises a solvent.

7. A method for producing a resist pattern comprising steps of;
(1) applying the resist composition of claim 1 onto a substrate;
(2) drying the applied composition to form a composition layer;
(3) exposing the composition layer;
(4) heating the exposed composition layer, and
(5) developing the heated composition layer.

* * * * *